US007300956B2

(12) United States Patent
Gallop et al.

(10) Patent No.: US 7,300,956 B2
(45) Date of Patent: *Nov. 27, 2007

(54) ACYLOXYALKYL CARBAMATE PRODRUGS, METHODS OF SYNTHESIS AND USE

(75) Inventors: Mark A. Gallop, Los Altos, CA (US);
Fenmei Yao, Mountain View, CA (US);
Maria J. Ludwikow, Cupertino, CA (US); Thu Phan, Fremont, CA (US);
Ge Peng, Mountain View, CA (US)

(73) Assignee: Xenoport, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/508,131

(22) Filed: Aug. 21, 2006

(65) Prior Publication Data

US 2007/0054945 A1    Mar. 8, 2007

Related U.S. Application Data

(63) Continuation of application No. 10/932,374, filed on Aug. 20, 2004, now Pat. No. 7,109,239.

(60) Provisional application No. 60/606,637, filed on Aug. 13, 2004, provisional application No. 60/496,938, filed on Aug. 20, 2003.

(51) Int. Cl.
*A61K 31/24* (2006.01)
*C07D 401/04* (2006.01)
*C07D 207/00* (2006.01)
*C07D 333/36* (2006.01)
*C07D 307/02* (2006.01)
*C07D 271/00* (2006.01)

(52) U.S. Cl. .................. 514/534; 546/279.4; 548/530; 549/68; 549/484; 560/24

(58) Field of Classification Search ...................... None
See application file for complete search history.

(56) References Cited

U.S. PATENT DOCUMENTS

| | | | |
|---|---|---|---|
| 2,996,431 A | 8/1961 | Barry |
| 3,139,383 A | 6/1964 | Neville |
| 3,402,240 A | 9/1968 | Cain et al. |
| 3,471,548 A | 10/1969 | Keberle et al. |
| 3,634,428 A | 1/1972 | Keberle et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,036,829 A | 7/1977 | Ferres et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,088,864 A | 5/1978 | Theeuwes et al. |
| 4,093,709 A | 6/1978 | Choi et al. |
| 4,094,992 A | 6/1978 | Kaplan et al. |
| 4,126,684 A | 11/1978 | Robson et al. |
| 4,200,098 A | 4/1980 | Ayer et al. |
| 4,285,987 A | 8/1981 | Ayer et al. |
| 4,421,736 A | 12/1983 | Walters |
| 4,434,153 A | 2/1984 | Urquhart et al. |
| 4,721,613 A | 1/1988 | Urquhart et al. |
| 4,752,470 A | 6/1988 | Mehta |
| 4,760,057 A | 7/1988 | Alexander |
| 4,816,263 A | 3/1989 | Ayer et al. |
| 4,820,523 A | 4/1989 | Shtohryn et al. |
| 4,853,229 A | 8/1989 | Theeuwes |
| 4,916,230 A | 4/1990 | Alexander |
| 4,996,058 A | 2/1991 | Sinnreich et al. |
| 5,006,560 A | 4/1991 | Kreutner |
| 5,091,184 A | 2/1992 | Khanna |
| 5,229,135 A | 7/1993 | Philippon |
| 5,466,811 A | 11/1995 | Alexander |
| 5,684,018 A | 11/1997 | Alexander |

(Continued)

FOREIGN PATENT DOCUMENTS

DE    4224342 A1    1/1994

(Continued)

OTHER PUBLICATIONS

Alderman, "A Review of cellulose Ethers in Hydrophilic Matrices dor Oral controlled-Release Dosage Forms," *Int. J. Pharm. Tech. & Prod. Mfr.* 1984, 5(3) 1-9.
Astudillo et al., "A Very Simple Oxidation of Olefins and Ketones with UHP-Maleic Anhydride," *Heterocycles* 1993, 36, 1075-1080.
Balicki et al., "Mild and Efficient Conversion of Nitriles to Amides with Basic Urea-Hydrogen Peroxide Adduct," *Synth. Commun.* 1993, 23, 3149.
Bamba, et al., "Release Mechanisms in Gelforming Sustained Release Preparations," *Int. J. Pharm.* 1979, 2, 307.

(Continued)

*Primary Examiner*—Paul A. Zucker
(74) *Attorney, Agent, or Firm*—Dorsey & Whitney LLP

(57) ABSTRACT

The disclosures herein relate generally to acyloxyalkyl carbamate prodrugs of (±)-4-amino-3-(4-chlorophenyl)butanoic acid and analogs thereof, pharmaceutical compositions thereof, methods of making prodrugs of (±)-4-amino-3-(4-chlorophenyl)butanoic acid and analogs thereof, methods of using prodrugs of (±)-4-amino-3-(4-chlorophenyl)butanoic acid and analogs thereof, and pharmaceutical compositions thereof for treating or preventing common diseases and/or disorders such as spasticity and/or acid reflux disease. The disclosures herein also relate to acyloxyalkyl carbamate prodrugs of (±)-4-amino-3-(4-chlorophenyl)butanoic acid and analogs thereof which are suitable for oral administration and to sustained release oral dosage forms thereof.

8 Claims, No Drawings

U.S. PATENT DOCUMENTS

| | | | |
|---|---|---|---|
| 5,698,155 | A | 12/1997 | Grosswald et al. |
| 5,719,185 | A | 2/1998 | Bountra et al. |
| 5,773,592 | A | 6/1998 | Mills |
| 6,051,734 | A | 4/2000 | Wildervanck et al. |
| 6,117,908 | A | 9/2000 | Andrews et al. |
| 6,375,987 | B1 | 4/2002 | Farah et al. |
| 6,379,700 | B2 | 4/2002 | Joachim et al. |
| 6,627,223 | B2 | 9/2003 | Percel et al. |
| 7,109,239 | B2* | 9/2006 | Gallop et al. ............... 514/533 |
| 2002/0151529 | A1 | 10/2002 | Cundy et al. |
| 2003/0171303 | A1 | 9/2003 | Gallop et al. |
| 2003/0176398 | A1 | 9/2003 | Gallop et al. |
| 2003/0228644 | A1 | 12/2003 | Mills |
| 2004/0006132 | A1 | 1/2004 | Gallop et al. |
| 2004/0014940 | A1 | 1/2004 | Raillard et al. |

FOREIGN PATENT DOCUMENTS

| | | |
|---|---|---|
| DE | 4424975 A1 | 1/1996 |
| EP | 0130119 A2 | 6/1984 |
| EP | 0463969 B1 | 2/1995 |
| EP | 1178034 A1 | 2/2002 |
| JP | 01319466 A2 | 12/1989 |
| WO | WO 98/22110 A1 | 5/1998 |
| WO | WO 01/08675 A1 | 2/2001 |
| WO | WO 01/26638 A2 | 4/2001 |
| WO | WO 01/26638 A3 | 4/2001 |
| WO | WO 01/90052 A1 | 11/2001 |
| WO | WO 02/096404 A1 | 12/2002 |
| WO | WO 02/100347 A2 | 12/2002 |
| WO | WO 02/100347 A3 | 12/2002 |
| WO | WO 03/011255 A1 | 2/2003 |

OTHER PUBLICATIONS

Berthelot et al., "3-Thienyl- and 3-furylaminobutyric acids. Synthesis and binding GABAB receptor studies," *J. Med. Chem.* 1991, 34, 2557-2560.

Berthelot et al., "Synthesis and pharmacological evaluation of gamma-aminobutyric acid analogues. New ligand for GABAB sites," *J. Med. Chem.* 1987, 30, 743-746.

Bowery, "GABAB receptors and their significance in mammalian pharmacology," *Trends Pharmacol. Sci.* 1989, 10, 401-407.

Butcher "Carbamate Esters: a Simple, Mild Method of Formation," *SynLett*, 1994, 825-826.

Cercos-Fortea et al., "Influence Of Leucine On Intestinal Baclofen Absorption As A Model Compound Of Neutral Alpha-Aminoacids," *Biopharm. Drug. Dis.* 1995, 16, 563-577.

Chenevert et al., "Chemoenzymatic Synthesis of Both Enantiomers of Baclofen," *Tetrahedron Lett.* 1991, 32, 4249-4250.

Ciccaglione et al., "Effect of acute and chronic administration of the $GABA_B$ agonist baclofen on 24 hour pH metry and symptoms in control subjects and in patients with gastro-oesophageal reflux disease," *Gut* 2003, 52, 363-470.

Coleman et al., "Polymer Review: A Practical Guide to Polymer Miscibility," *Polymers* 1990, 31, 1187-1231.

Cooper et al., "Oxidation Reactions Using Urea-Hydrogen Peroxide: A Safe Alternative to Anhydrous Hydrogen Peroxide," *Synlett.* 1990, 533-535.

Deguchi et al., "Study on brain interstitial fluid distribution and blood-brain barrier transport of baclofen in rats by microdialysis," *Pharm. Res.* 1995, 12, 1838-1844.

During et al., "Controlled release of dopamine from a polymeric brain implant: in vivo characterization," 1989, *Ann. Neurol.* 25:351.

Fincher, "Particle Size of Drugs and Its Relationship to Absorption and Activity," *J. Pharm. Sci.* 1968, 57, 1825-1835.

Fromm et al., "Comparison of L-baclofen and racemic baclofen in trigeminal neuralgia," *Neurology* 1987, 37, 1725-1728.

Goodson, "Medical Applications of Controlled Release," vol. 2, pp. 115-138 (1984).

Guillon et al. "Pharmacological Evaluation of New Baclofen Derivatives," *Pharm. Pharmacol. Commun.* 1999, 5, 243-247.

Herdeis et al., "Synthesis of Homochiral R-Baclofen from S-Glutamic Acid," *Tetrahedron Asymmetry* 1992, 3, 1213-1221.

Hoes et al., "The Application of Drug-Polymer Conjugates in Chemotherapy," *Drug Carrier Systems* 1989, 9, 57-110.

Howard et al., "Intracerebral drug delivery in rats with lesion-induced memory deficits," *J. Neurosurg.* 1989 71(1):105-112.

Krach, "Pharmacotherapy Of Spasticity: Oral Medications And Intrathecal Baclofen," *J. Child Neurol.* 2001, 16, 31-36.

Katz, "Management of Spasticity," *Am. J. Phys. Med. Rehabil.* 1988, 2, 108-116.

Kayser et al., "Designer Yeast: an Enantioselective Oxidizing Reagent for Organic Synthesis." *SynLett* ,1999, 1:153.

Krogsgaard-Larsen, "GABA Synaptic Mechanisms: Stereochemical And Conformational Requirements," *Med. Res. Rev.* 1988, 8, 27-56.

Langer et al., , "Chemical and Physical Structure of Polymers as Carriers for Controlled Relaease of Bioactive Agents: A Review," *J Macromol. Sci. Rev. Macromol Chem.* 1983, 23:61.

Langer, "New Method of Drug Delivery," 1990, *Science* 249:1527-1533.

Leisen et al., "Lipophilicities of baclofen ester prodrugs correlate with affinities to the ATP-dependent efflux pump P-glycoprotein: relevance for their permeation across the blood-brain barrier?" *Pharm. Res.* 2003, 20, 772-778.

Leong et al., "Polymeric Controlled Drug Delivery," *Adv. Drug Delivery Rev.* 1987, 1, 199-233.

Levy et al., "Inhibition of Calcification of Bioprosthetic Heart Valves by Local Controlled-Release Diphosphonate," *Science* 1985 228: 190-192.

List, et al., "The proline-catalyzed direct asymmetric three-component Mannich reaction: scope, optimization, and application to the highly enantioselective synthesis of 1,2-amino alcohols," *J. Am. Chem. Soc.* 2002, 124, 827-833.

Lu, "Dimensionless Presentation for Drug Release From a Coated Pure Drug Bead: 2 Experiment," *Int. J. Pharm.*, 1994, 112, 117-124.

Merino et al., "Evidence of a specialized transport mechanism for the intestinal absorption of baclofen," *Biopharm. Drug. Disp.* 1989, 10, 279-297.

Misgeld et al., "A physiological role for GABAB receptors and the effects of baclofen in the mammalian central nervous system," *Prog. Neurobiol.* 1995, 46, 423-462.

Moll-Navarro et al., "Interaction Of Taurine On Baclofen Intestinal Absorption: A Nonlinear Mathematical Treatment Using Differential Equations To Describe Kinetic Inhibition Models," *J. Pharm. Sci.* 1996, 85, 1248-1254.

Ohtsuki et al., "Role of blood-brain barrier organic anion transporter 3 (OAT3) in the efflux of indoxyl sulfate, a uremic toxin: its involvement in neurotransmitter metabolite clearance from the brain," *J. Neurochem.* 2002, 83, 57-66.

Renz et al., "100 years of Baeyer-Villiger Oxidations," *Eur. J. Org. Chem.*, 1999, 737-750.

Linhardt, *Controlled Release of Drugs* Chap. 2, (1989) pp. 53-95.

Sampathkumar et al., "Baclofen withdrawal presenting as multiorgan system failure," *Anesth. Analg.* 1998, 87, 562-563.

Saudek et al., "A Preliminary Trial of the Programmable Implantable Medication System for Insulin Delivery," *N. Engl. J. Med.*, 1989, 321: 574.

Sawynok et al. "D-Baclofen Is An Antagonist At Baclofen Receptors Mediating Antinociception In The Spinal Cord," *Pharmacology* 1985, 31, 248-259.

Sefton, "Implantable Pumps," *CRC Crit Ref Biomed. Eng.* 1987, 14:201.

Stewart, "Cyclohexanone Monooxygenase: A Useful Reagent For Asymmetric Baeyer-Villiger Reactions," *Current Organic Chemistry*,1998, 2:195-216.

Stewart, et al., "Comparison Of Intestinal Permeabilities Determined In Multiple In Vitro And In Situ Models: Relationship To Absorption In Humans," *Pharm. Res.*, 1995, 12, 693-699.

Strukul, "Transition Metal Catalysis in the Baeyer-Villiger Oxidation of Ketones," *Angnew. Chem. Int. Ed.*, 1998, 37:1198-1209.

Terrence et al., "Effect Of Baclofen Enantiomorphs On The Spinal Trigeminal Nucleus And Steric Similarities Of Carbamazepine," *Pharmacology* 1983, 27, 85-94.

Thakur et al., "Enantioselective Synthesis of (R)-(−)-Baclofen Via Ru(II)-BINAP Catalyzed Asymmetric Hydrogenation," *Tetrahedron Asymmetry* 2003, 14, 581-586.

van Bree et al., "Stereoselective Transport Of Baclofen Across The Blood-Brain Barrier In Rats As Determined By The Unit Impulse Response Methodology," *Pharm. Re.* 1991, 8, 259-262.

van Bree et al., "Carrier-mediated Transport Of Baclofen Across Monolayers Of Bovine Brain Endothelial Cells In Primary Culture," *Pharm. Res.* 1988, 5, 369-371.

van Herwaarden et al., "The Effect Of Baclofen On Gastro-Oesophageal Reflux, Lower Oesophageal Sphincter Function And Reflux Symptoms In Patients With Reflux Disease," *Aliment. Pharmacol. Ther.* 2002, 16, 1655-1662.

Varma et al., "The Urea-Hydrogen Peroxide Complex: Solid-State Oxidative Protocols for Hydroxylated Aldehydes and Ketones (Dakin Reactions), Nitriles, Sulfides, and Nitrogen Heterocycles," *Organic Lett.* 1999, 1, 189-191.

Verma et al., "Osmotically Controlled Oral Drug Delivery," *Drug Dev. Ind. Pharm.*, 2000, 26:695-708.

Wall et al., "Metabolism Of 3-(P-Chlorophenyl)Pyrrolidine. Structural Effects In Conversion Of A Prototype Gamma-Aminobutyric Acid Prodrug To Lactam And Gamma-Aminobutyric Acid Type Metabolites," *J. Med. Chem.* 1989, 32, 1340-1348.

Witezuk et al., "3-(p-Chlorophenyl)-4-aminobutanoic acid—resolution into enantiomers and pharmacological activity," *Pol. J. Pharmacol. Pharm.* 1980, 32, 187-196.

Yoshifuji et al., "Stereospecific Synthesis of (R)- and (S)- Baclofen and (R)-and (S)-PCPGABA [4-Amino-2-(4-Chlorophenyl)Butyric Acid] via (R)- and (S)-3-(4-Chlorophenyl)Pyrrolidines," *Chem Pharm. Bull.* 1995, 43, 1302-1306.

* cited by examiner

ACYLOXYALKYL CARBAMATE PRODRUGS, METHODS OF SYNTHESIS AND USE

This is a continuation of U.S. Ser. No. 10/932,374, filed Aug. 20, 2004, now U.S. Pat. No. 7,109,239, which claims the benefit under 35 U.S.C. § 119(e) from U.S. Provisional Application Ser. No. 60/496,938, filed Aug. 20, 2003 and U.S. Provisional Application Ser. No. 60/606,637 filed Aug. 13, 2004 which are herein incorporated by reference in their entirety.

1. TECHNICAL FIELD

The disclosures herein relate generally to acyloxyalkyl carbamate prodrugs of (±)-4-amino-3-(4-chlorophenyl)butanoic acid and analogs thereof, pharmaceutical compositions thereof, methods of making prodrugs of (±)-4-amino-3-(4-chlorophenyl)butanoic acid and analogs thereof and methods of using prodrugs of (±)-4-amino-3-(4-chlorophenyl)butanoic acid and analogs thereof and pharmaceutical compositions thereof to treat various diseases or disorders. The disclosures herein also relate to such prodrugs suitable for oral administration and for oral administration using sustained release dosage forms.

2. BACKGROUND (±)-4-Amino-3-(4-chlorophenyl)butanoic acid (baclofen), (1), is an analog of gamma-aminobutyric acid (i.e., GABA) that selectively activates $GABA_B$ receptors, resulting in neuronal hyperpolarization. $GABA_B$ receptors are located in laminae I-IV of the spinal cord, where primary sensory fibers end. These G-protein coupled receptors activate conductance by $K^+$-selective ion channels and can reduce currents mediated by $Ca^{2+}$ channels in certain neurons. Baclofen has a presynaptic inhibitory effect on the release of excitatory neurotransmitters and also acts postsynaptically to decrease motor neuron firing (see Bowery, *Trends Pharmacol. Sci.* 1989, 10, 401-407; Misgeld et al., *Prog. Neurobiol.* 1995, 46, 423-462).

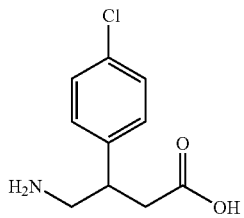

Baclofen (1)

Many examples of compounds having agonistic or partially agonistic affinity to $GABA_B$ receptors exist and include certain amino acids, aminophosphonic acids, aminophosphinic acids, aminophosphonous acids and aminosulfinic acids such as, for example,
4-amino-3-(2-chlorophenyl)butanoic acid;
4-amino-3-(4-fluorophenyl)butanoic acid;
4-amino-3-hydroxybutanoic acid;
4-amino-3-(4-chlorophenyl)-3-hydroxyphenylbutanoic acid;
4-amino-3-(thien-2-yl)butanoic acid;
4-amino-3-(5-chlorothien-2-yl)butanoic acid;
4-amino-3-(5-bromothien-2-yl)butanoic acid;
4-amino-3-(5-methylthien-2-yl)butanoic acid;
4-amino-3-(2-imidazolyl)butanoic acid;
4-guanidino-3-(4-chlorophenyl)butanoic acid;
(3-aminopropyl)phosphonous acid;
(4-aminobut-2-yl)phosphonous acid;
(3-amino-2-methylpropyl)phosphonous acid;
(3-aminobutyl)phosphonous acid;
(3-amino-2-(4-chlorophenyl)propyl)phosphonous acid;
(3-amino-2-(4-chlorophenyl)-2-hydroxypropyl)phosphonous acid;
(3-amino-2-(4-fluorophenyl)propyl)phosphonous acid;
(3-amino-2-phenylpropyl)phosphonous acid;
(3-amino-2-hydroxypropyl)phosphonous acid;
(E)-(3-aminopropen-1-yl)phosphonous acid;
(3-amino-2-cyclohexylpropyl)phosphonous acid;
(3-amino-2-benzylpropyl)phosphonous acid;
[3-amino-2-(4-methylphenyl)propyl]phosphonous acid;
[3-amino-2-(4-trifluoromethylphenyl)propyl]phosphonous acid;
[3-amino-2-(4-methoxyphenyl)propyl]phosphonous acid;
[3-amino-2-(4-chlorophenyl)-2-hydroxypropyl]phosphonous acid;
(3-aminopropyl)methylphosphinic acid;
(3-amino-2-hydroxypropyl)methylphosphinic acid;
(3-aminopropyl)(difluoromethyl)phosphinic acid;
(4-aminobut-2-yl)methylphosphinic acid;
(3-amino-1-hydroxypropyl)methylphosphinic acid;
(3-amino-2-hydroxypropyl)(difluoromethyl)phosphinic acid;
(E)-(3-aminopropen-1-yl)methylphosphinic acid;
(3-amino-2-oxo-propyl)methyl phosphinic acid;
(3-aminopropyl)hydroxymethylphosphinic acid;
(5-aminopent-3-yl)methylphosphinic acid;
(4-amino-1,1,1-trifluorobut-2-yl)methylphosphinic acid;
3-aminopropylsulfinic acid;
(3-amino-2-(4-chlorophenyl)propyl)sulfinic acid;
(3-amino-2-hydroxypropyl)sulfinic acid;
(2S)-(3-amino-2-hydroxypropyl)sulfinic acid;
(2R)-(3-amino-2-hydroxypropyl)sulfinic acid;
(3-amino-2-fluoropropyl)sulfinic acid;
(2S)-(3-amino-2-fluoropropyl)sulfinic acid;
(2R)-(3-amino-2-fluoropropyl)sulfinic acid; and
(3-amino-2-oxopropyl)sulfinic acid.

A principal pharmacological effect of baclofen in mammals is reduction of muscle tone and the drug is frequently used in the treatment of spasticity. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia and neurodegenerative diseases. Patients with spasticity complain of stiffness, involuntary spasm and pain. These painful spasms may be spontaneous or triggered by a minor sensory stimulus, such as touching the patient.

Baclofen is useful in controlling gastro-esophageal reflux disease (van Herwaarden et al., *Aliment. Pharmacol. Ther.* 2002, 16, 1655-1662, Ciccaglione et al., *Gut* 2003, 52, 464-470; Andrews et al., U.S. Pat. No. 6,117,908; Fara et al., International Publication No. WO02/096404); in promoting alcohol abstinence in alcoholics (Gessa et al., International Publication No. WO01/26638); in promoting smoking cessation (Gessa et al., International Publication No. WO01/08675); in reducing addiction liability of narcotic agents (Robson et al., U.S. Pat. No. 4,126,684); in the treatment of emesis (Bountra et al., U.S. Pat. No. 5,719,185) and as an anti-tussive for the treatment of cough (Kreutner et al., U.S. Pat. No. 5,006,560).

Baclofen may be administered orally or by intrathecal delivery through a surgically implanted programmable pump. The drug is rapidly absorbed from the gastrointestinal tract and has an elimination half-life of approximately 3-4 hours. Baclofen is partially metabolized in the liver but is largely excreted by the kidneys unchanged. The short half-life of baclofen necessitates frequent administration with typical oral dosing regimens ranging from about 10 to about 80 mg of three or four divided doses daily. Plasma baclofen concentrations of about 80 to about 400 ng/mL result from these therapeutically effective doses in patients (Katz, *Am. J. Phys. Med. Rehabil.* 1988, 2, 108-116; Krach, *J. Child Neurol.* 2001, 16, 31-36). When baclofen is given orally, sedation is a side effect, particularly at elevated doses. Impairment of cognitive function, confusion, memory loss, dizziness, weakness, ataxia and orthostatic hypotension are other commonly encountered baclofen side-effects.

Intrathecal administration is often recommended for patients who find the adverse effects of oral baclofen intolerable. The intrathecal use of baclofen permits effective treatment of spasticity with doses less than $1/100^{th}$ of those required orally, since administration directly into the spinal subarachnoid space permits immediate access to the $GABA_B$ receptor sites in the dorsal horn of the spinal cord. Surgical implantation of a pump is, however, inconvenient and a variety of mechanical and medical complications can arise (e.g., catheter displacement, kinking or blockage, pump failure, sepsis and deep vein thrombosis). Acute discontinuation of baclofen therapy (e.g., in cases of mechanical failure) may cause serious withdrawal symptoms such as hallucinations, confusion, agitation and seizures (Sampathkumar et al., *Anesth. Analg.* 1998, 87, 562-563).

While the clinically-prescribed baclofen product (Lioresal™) is available only as a racemate, the $GABA_B$ receptor agonist activity resides entirely in one enantiomer. R-(-)-baclofen (2) (also termed L-baclofen).

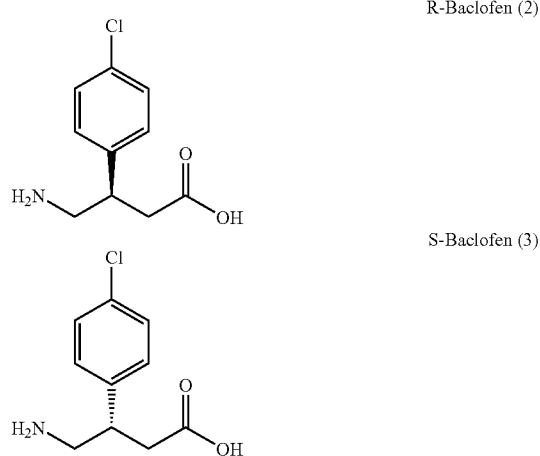

R-Baclofen (2)

S-Baclofen (3)

The other isomer, S-baclofen, actually antagonizes the action of R-baclofen at $GABA_B$ receptors and its antinociceptive activity in the rat spinal cord (Terrence et al., *Pharmacology* 1983, 27, 85-94; Sawynok et al. *Pharmacology* 1985, 31, 248-259). Orally administered R-baclofen is reported to be about 5-fold more potent than orally administered racemic baclofen, with an R-baclofen regimen of 2 mg t.i.d being equivalent to racemic baclofen at 10 mg t.i.d. (Fromm et al., *Neurology* 1987, 37, 1725-1728). Moreover, the side effect profile, following administration of R-baclofen, has been shown to be significantly reduced, relative to equally efficacious dose of racemic baclofen.

Baclofen, a zwitterionic amino acid, lacks the requisite physicochemical characteristics for effective passive permeability across cellular membranes. Passage of the drug across the gastrointestinal tract and the blood-brain barrier (BBB) are mediated primarily by active transport processes, rather than by passive diffusion. Accordingly, baclofen is a substrate for active transport mechanisms shared by neutral α-amino acids like leucine, and β-amino acids like β-alanine and taurine (van Bree et al., *Pharm. Res.* 1988, 5, 369-371; Cercos-Fortea et al, *Biopharm. Drug. Disp.* 1995, 16, 563-577; Deguchi et al., *Pharm. Res.* 1995, 12, 1838-1844; Moll-Navarro et al., *J. Pharm. Sci.* 1996, 85, 1248-1254). Transport across the BBB is stereoselective, with preferential uptake of the active R-enantiomer (2) being reported (van Bree et al., *Pharm. Res.* 1991, 8, 259-262). In addition, organic anion transporters localized in capillary endothelial cells of the blood-brain barrier have been implicated in efflux of baclofen from the brain (Deguchi et al., supra; Ohtsuki et al., *J. Neurochem.* 2002, 83, 57-66). 3-(p-Chlorophenyl)pyrrolidine has been described as a CNS-penetrable prodrug of baclofen (Wall et al., *J. Med. Chem.* 1989, 32, 1340-1348). Prodrugs of other GABA analogs are described in Bryans et al., International Publication No. WO01/90052; Bryans et al., EP1178034; Cundy et al., U.S. Patent Application Publication No. 2002/0151529, Gallop et al., U.S. Patent Application Publication No. 2003/0176398; Gallop et al., U.S. Patent Application Publication No. 2003/0171303; Gallop et al., U.S. Patent Application Publication No. 2004/0006132; and Raillard et al., U.S. Patent Application Publication No. 2004/0014940.

Sustained released oral dosage formulations are a conventional solution to the problem of rapid systemic drug clearance, as is well known in the art (see, e.g., "Remington's Pharmaceutical Sciences," Philadelphia College of Pharmacy and Science, 19th Edition, 1995). Osmotic delivery systems are also recognized methods for sustained drug delivery (See, e.g., Verma et al., *Drug Dev. Ind. Pharm.* 2000, 26, 695-708). Successful application of these technologies depends on the drug of interest having an effective level of absorption from the large intestine (also referred to herein as the colon), where the dosage form spends a majority of its time during its passage down the gastrointestinal tract. Baclofen is poorly absorbed following administration into the colon in animal models (Merino et al., *Biopharm. Drug. Disp.* 1989, 10, 279-297), presumably, since the transporter proteins mediating baclofen absorption in the upper region of the small intestine are not expressed in the large intestine. Development of an oral controlled release formulation for baclofen should considerably improve the convenience, efficacy and side effect profile of baclofen therapy. However, the rapid passage of conventional dosage forms through the proximal absorptive region of the small intestine has thus far prevented the successful application of sustained release technologies to this drug. A number of exploratory delivery technologies that rely on either mucoadhesion or gastric retention have been suggested to achieve sustained delivery of baclofen (Sinnreich, U.S. Pat. No. 4,996,058; Khanna, U.S. Pat. No. 5,091,184; Fara et al., supra; Dudhara et al., International Publication No. WO03/011255) though to date none of these appear to be able to achieve sustain blood levels of baclofen in human subjects.

Thus, there is a significant need for new prodrugs of baclofen and baclofen analogs which are well absorbed in the large intestine/colon and hence suitable for oral sustained release formulations, thus improving the convenience, efficacy and side effect profile of baclofen therapy.

3. SUMMARY

These and other needs are satisfied by the disclosure herein of acyloxyalkyl carbamate prodrugs of baclofen and baclofen analogs, pharmaceutical compositions of acyloxyalkyl carbamate prodrugs of baclofen and baclofen analogs, methods of making acyloxyalkyl carbamate prodrugs of baclofen and baclofen analogs and methods of using acyloxyalkyl carbamate prodrugs of baclofen and baclofen analogs and/or pharmaceutical compositions thereof to treat various medical disorders.

In a first aspect, a compound of Formula (I) is provided,

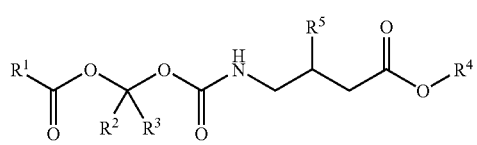

or pharmaceutically acceptable salts, hydrates or solvates thereof, wherein:

$R^1$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl and substituted heteroarylalkyl or optionally, $R^2$ and $R^3$ together with the carbon atom to which they are bonded form a cycloalkyl, substituted cycloalkyl, cycloheteroalkyl or substituted cycloheteroalkyl ring;

$R^4$ is selected from the group consisting of hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl; and $R^5$ is selected from the group consisting of substituted aryl, heteroaryl and substituted heteroaryl.

In a second aspect, a compound of Formula (II) is provided,

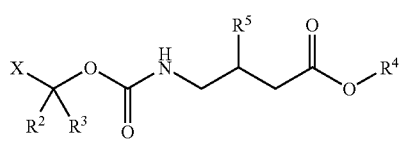

wherein:
X is fluoro, chloro, bromo or iodo; and
$R^2$, $R^3$, $R^4$ and $R^5$ are as defined, supra.

In a third aspect, a method of synthesizing a compound of Formula (I) is provided, comprising:

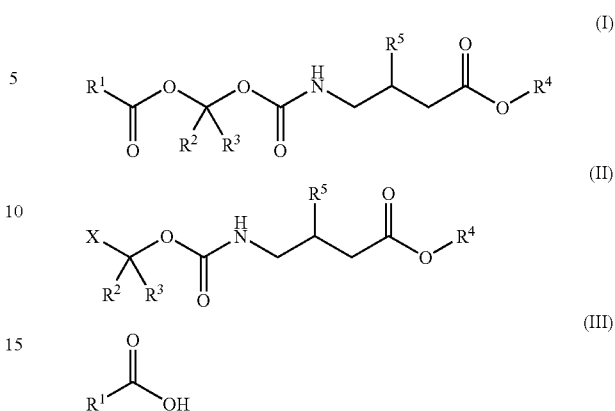

contacting a compound of Formula (II), a compound of Formula (III) and at least one equivalent of a metal salt or an organic base or a combination thereof wherein:
X is fluoro, chloro, bromo or iodo; and
$R^1$, $R^2$, $R^3$, $R^4$, and $R^5$ are as defined, supra.

In a fourth aspect, a method of synthesizing a compound of Formula (I) is provided, comprising contacting a compound of Formula (XVIII) with an oxidant, wherein:

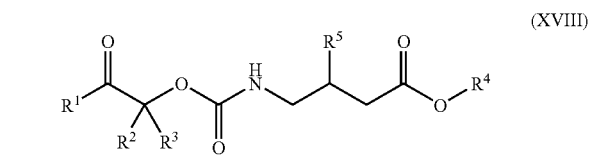

and $R^1$, $R^2$, $R^3$, $R^4$, and $R^5$ are as defined, supra.

In a fifth aspect, pharmaceutical compositions comprising a compound of Formula (I), or pharmaceutically acceptable salts, hydrates or solvates thereof, and a pharmaceutically acceptable vehicle such as a diluent, carrier, excipient or adjuvant are provided. The choice of diluent, carrier, excipient and adjuvant will depend upon, among other factors, the desired mode of administration.

In a sixth aspect, a sustained release oral dosage form, comprising a baclofen prodrug or a baclofen analog prodrug of Formula (I) is provided, the dosage form being adapted to be swallowed by a patient in order to introduce the dosage form into an intestinal lumen of the patient, the dosage form further being adapted to release the baclofen prodrug or a baclofen analog prodrug of Formula (I) gradually into the intestinal lumen of the patient over a period of hours after said swallowing, said gradual release causing baclofen or the baclofen analog to be cleaved from the promoiety after said swallowing and providing a therapeutic concentration of baclofen or the baclofen analog in the plasma of the patient.

In a seventh aspect, a method of orally administering a baclofen prodrug or a baclofen analog prodrug of Formula (I) is provided, said method comprising:
placing a compound of Formula (I) in a sustained release oral dosage form;
introducing the dosage form into the intestinal lumen of a patient by having the patient swallow the dosage form;
releasing the prodrug gradually from the swallowed dosage form into the intestinal lumen of the patient over a period of hours; and allowing baclofen or the baclofen analog to be cleaved from the promoiety after said swallowing to provide a therapeutic concentration of the baclofen or baclofen analog in the plasma of the patient.

In an eighth aspect, methods are provided for treating or preventing stiffness, involuntary movements and pain associated with spasticity. Methods are also provided for treating or preventing gastro-esophageal reflux disease, alcohol abuse or addiction, nicotine abuse or addiction, narcotics abuse or addiction, emesis and cough. The methods generally involve administering to a patient in need of such treatment or prevention a therapeutically effective amount of a compound of Formula (I) and/or a pharmaceutical composition thereof.

4. DETAILED DESCRIPTION

4.1 Definitions

"1-Acyloxy-Alkyl Carbamate" refers to an N-1-acyloxyalkoxycarbonyl derivative of baclofen or a baclofen analog as encompassed by compounds of Formulae (I), (V) and (VI) disclosed herein.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, most preferably, from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (secbutyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Alkoxy" by itself or as part of another substituent refers to a radical —O$R^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)O$R^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, from 6 to 12 carbon atoms.

"Arylalkyl" by itself or as part of another substituent refers to an acyclic alkyl radical in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryldialkylsilyl" by itself or as part of another substituent refers to the radical —Si$R^{32}R^{33}R^{34}$ where one of $R^{32}$, $R^{33}$ or $R^{34}$ is aryl as defined herein and the other two of $R^{32}$, $R^{33}$ or $R^{34}$ are alkyl as defined herein.

"AUC" is the area under the plasma drug concentration-versus-time curve extrapolated from zero time to infinity.

"$C_{max}$" is the highest drug concentration observed in plasma following an extravascular dose of drug.

"Compounds" refers to compounds encompassed by structural formulae (I)-(XXIII) disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e. geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Cycloalkoxycarbonyl" by itself or as part of another substituent refers to a radical —C(O)OR$^{36}$ where R$^{36}$ represents an cycloalkyl group as defined herein. Representative examples include, but are not limited to, cyclobutyloxycarbonyl, cyclohexyloxycarbonyl and the like.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$-$C_{10}$) cycloalkyl, more preferably ($C_3$-$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"1-Haloalkyl Carbamate" refers to an N-1-haloalkoxycarbonyl derivative of baclofen or a baclofen analog as encompassed by compounds of Formulae (II), (VII) and (VIII) disclosed herein.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine; phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl, more preferably, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Parent Aromatic Ring System" refers to an unsaturated cyclic or polycyclic ring system having a conjugated 71 electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring-systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound and a pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound sis administered.

"Patient" includes humans. The terms "human" and "patient" are used interchangeably herein.

"Preventing" or "prevention," refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and ally ethers.

"Substantially one diastereomer" refers to a compound containing 2 or more stereogenic centers such that the diastereomeric excess (d.e.) of the compound is greater than or at least 90%. In some embodiments, the d.e. is, for example, greater than or at least 91%, 92%, 93%, 94%, 95%, 96%, 97%, 98% or 99%.

"Substituted" refers to a group in which one or more hydrogen atoms are independently replaced with the same or different substituent(s). Typical substituents include, but are not limited to, -M, —$R^{60}$, —O—, =O$^-$, —O$R^{60}$, —S$R^{60}$, —S$^-$, =S, —N$R^{60}R^{61}$, =N$R^{60}$, —CF$_3$, —CN, —OCN, —SCN, —NO, —NO$_2$, =N$_2$, —N$_3$, —S(O)$_2$O$^-$, —S(O)$_2$OH, —S(O)$_2R^{60}$, —OS(O)$_2$O$^-$, —OS(O)$_2R^{60}$, —P(O)(O)$_2$, —P(O)(O$R^{60}$)(O$^-$), —OP(O)($R^{60}$)(O$R^{61}$), —C(O)$R^{60}$, —C(S)$R^{60}$, —C(O)O$R^{60}$, —C(O)N$R^{60}R^{61}$, —C(O)O$^{31}$, —C(S)O$R^{60}$, —N$R^{62}$C(O)N$R^{60}R^{61}$, —N$R^{62}$C(S)N$R^{60}R^{61}$, —N$R^{62}$C(N$R^{63}$)N$R^{60}R^{61}$ and —C(N$R^{62}$)N$R^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, —$R^{60}$, =O, —O$R^{60}$, —S$R^{60}$, —S$^-$, =S, —N$R^{60}R^{61}$, =N$R^{60}$, —CF$_3$, —CN, —OCN, —SCN, —NO, —NO$_2$, =N$_2$, —N$_3$, —S(O)$_2R^{60}$, —OS(O)$_2$O$^-$, —OS(O)$_2R^{60}$, —P(O)(O$^-$)$_2$, —P(O)(O$R^{60}$)(O$^-$), —OP(O)(O$R^{60}$)(O$R^{61}$), —C(O)$R^{60}$, —C(S)$R^{60}$, —C(O)O$R^{60}$, —C(O)N$R^{60}R^{61}$, —C(O)O—, —NR$^{62}$C(O)NR$^{60}$R$^{61}$, more preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O—, most preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Trialkylsilyl" by itself or as part of another substituent refers to a radical —SiR$^{50}$R$^{51}$R$^{52}$ where R$^{50}$, R$^{51}$ and R$^{52}$ are alkyl as defined herein.

Reference will now be made in detail to particular embodiments of compounds and methods. The disclosed embodiments are not intended to be limiting of the claims. To the contrary, is the claims are intended to cover all alternatives, modifications and equivalents.

4.2 Compounds

In a first aspect, a compound of Formula (I) is provided,

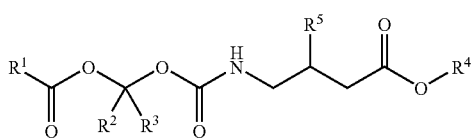

(I)

or pharmaceutically acceptable salts, hydrates or solvates thereof, wherein:

R$^1$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

R$^2$ and R$^3$ are independently selected from the group consisting of hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl and substituted heteroarylalkyl or optionally, R$^2$ and R$^3$ together with the carbon atom to which they are bonded form a cycloalkyl, substituted cycloalkyl, cycloheteroalkyl or substituted cycloheteroalkyl ring;

R$^4$ is selected from the group consisting of hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl; and R$^5$ is selected from the group consisting of substituted aryl, heteroaryl and substituted heteroaryl.

In some embodiments, R$^5$ is selected from the group consisting of 4-chlorophenyl, (3R)-4-chlorophenyl, 2-chlorophenyl, 4-fluorophenyl, thien-2-yl; 5-chlorothien-2-yl, 5-bromothien-2-yl, 5-methylthien-2-yl and 2-imidazolyl. In other embodiments, R$^5$ is selected from the group consisting of -chlorophenyl, (3R)-4-chlorophenyl, 2-chlorophenyl, 4-fluorophenyl.

In still other embodiments, the compound of Formula (I) has the structure of Formula (V):

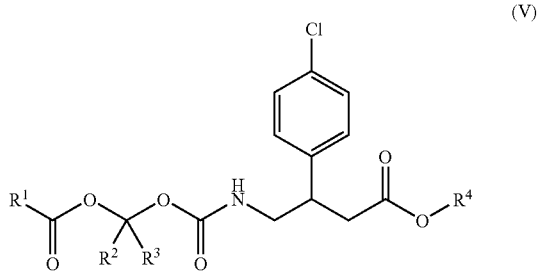

(V)

or pharmaceutically acceptable salts, hydrates or solvates thereof;

wherein:

R$^1$, R$^2$, R$^3$ and R$^4$ are as defined, supra.

In still other embodiments, a compound of Formula (I), has the structure of Formula (VI):

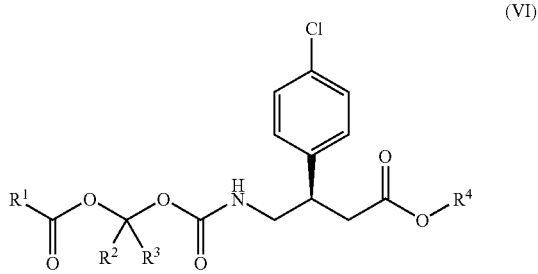

(VI)

or pharmaceutically acceptable salts, hydrates or solvates thereof;

wherein R$^1$, R$^2$, R$^3$ and R$^4$ are as defined, supra.

In some embodiments of compounds of Formulae (I), (V) or (VI), R$^1$ is selected from the group consisting of C$_{1-6}$ alkyl, substituted C$_{1-6}$ alkyl, C$_{3-6}$ cycloalkyl, phenyl, substituted phenyl, C$_{7-9}$ phenylalkyl and pyridyl. In other embodiments of compounds of Formulae (I), (V) or (VI), R$^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl. In still other embodiments of compounds of Formulae (I), (V) or (VI), R$^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl.

In still other embodiments of compounds of Formulae (I), (V) or (VI), $R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl. In still other embodiments of compounds of Formulae (I), (V) or (VI), $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl. In still other embodiments of compounds of Formulae (I), (V) or (VI), $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl. In still other embodiments of compounds of Formulae (I), (V) or (VI), $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl or 4-pyridyl and $R^3$ is hydrogen. In still other embodiments of compounds of Formulae (I), (V) or (VI), $R^2$ is hydrogen, methyl, ethyl, n-propyl, isopropyl, n-butyl, isobutyl, sec-butyl, phenyl or cyclohexyl and $R^3$ is hydrogen. In still other embodiments of a compound of Formulae (I), (V) or (VI), $R^2$ is methyl, methoxycarbonyl, ethoxycarbonyl, isopropoxycarbonyl or cyclohexyloxycarbonyl, and $R^3$ is methyl.

In still other embodiments of a compound of Formulae (I), (V) or (VI), $R^2$ and $R^3$ together with the carbon atom to which they are attached form a cycloalkyl, substituted cycloalkyl, cycloheteroalkyl or substituted cycloheteroalkyl ring. In still other embodiments of compounds of Formulae (I), (V) or (VI), $R^2$ and $R^3$ together with the carbon atom to which they are attached form a cyclobutyl, cyclopentyl or cyclohexyl ring.

In still other embodiments of a compound of Formulae (I), (V) or (VI), $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl. In still other embodiments of a compound of Formulae (I), (V) or (VI), $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl. In still other embodiments of a compound of Formulae (I), (V) or (VI), $R^4$ is hydrogen, allyl, benzyl or trimethylsilyl. In still other embodiments of a compound of Formulae (I), (V) or (VI), $R^4$ is hydrogen.

In some embodiments of a compound of Formula (I), $R^5$ is substituted aryl. In other embodiments of a compound of Formula (I), $R^5$ is substituted phenyl. In still other embodiments, $R^5$ is phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is hydrogen, methyl, ethyl, n-propyl, isopropyl, n-butyl, isobutyl, sec-butyl, phenyl or cyclohexyl, $R^3$ is hydrogen and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is methyl, methoxycarbonyl, ethoxycarbonyl, isopropoxy carbonyl or cyclohexyloxycarbonyl, $R^3$ is methyl and $R^4$ is selected from the group consisting of hydrogen, $C_{1-6}$ alkyl, substituted $C_{1-6}$ alkyl, $C_{3-9}$ cycloalkyl, phenyl, substituted phenyl, $C_{7-9}$ phenylalkyl, substituted $C_{7-9}$ phenylalkyl, trialkylsilyl and aryldialkylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen, methyl, ethyl, tert-butyl, allyl, benzyl, 4-methoxybenzyl, diphenylmethyl, triphenylmethyl, trimethylsilyl, triisopropylsilyl, tert-butyldimethylsilyl or phenyldimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl and $R^4$ is hydrogen, methyl, ethyl, tert-butyl, allyl, benzyl, 4-methoxybenzyl, diphenylmethyl, triphenylmethyl, trimethylsilyl, triisopropylsilyl, tert-butyldimethylsilyl or phenyldimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is hydrogen, methyl, ethyl, n-propyl, isopropyl, n-butyl, isobutyl, sec-butyl, phenyl or cyclohexyl, $R^3$ is hydrogen and $R^4$ is hydrogen, methyl, ethyl, tert-butyl, allyl, benzyl, 4-methoxybenzyl, diphenylmethyl, triphenylmethyl, trimethylsilyl, triisopropylsilyl, tert-butyldimethylsilyl or phenyldimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is methyl, methoxycarbonyl, ethoxycarbonyl, isopropoxycarbonyl or cyclohexyloxycarbonyl, $R^3$ is methyl and $R^4$ is hydrogen, methyl, ethyl, tert-butyl, allyl, benzyl, 4-methoxybenzyl, diphenylmethyl, triphenylmethyl, trimethylsilyl, triisopropylsilyl, tert-butyldimethylsilyl or phenyldimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen, allyl, benzyl or trimethylsilyl. Preferably, in the above embodiments, $R^1$ is methyl, ethyl, n-propyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl and $R^4$ is hydrogen, allyl, benzyl or trimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is hydrogen, methyl, ethyl, n-propyl, isopropyl, n-butyl, isobutyl, sec-butyl, phenyl or cyclohexyl, $R^3$ is hydrogen and $R^4$ is hydrogen, allyl, benzyl or trimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is methyl, methoxycarbonyl, ethoxycarbonyl, isopropoxycarbonyl or cyclohexyloxycarbonyl, $R^3$ is methyl and $R^4$ is hydrogen, allyl, benzyl or trimethylsilyl. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl and $R^4$ is hydrogen. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is hydrogen, methyl, ethyl, n-propyl, isopropyl, n-butyl, isobutyl, sec-butyl, phenyl or cyclohexyl, $R^3$ is hydrogen and $R^4$ is hydrogen. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl and pyridyl, $R^2$ is methyl, methoxycarbonyl, ethoxycarbonyl, isopropoxycarbonyl or cyclohexyloxycarbonyl, $R^3$ is methyl and $R^4$ is hydrogen. Preferably, in the above embodiments, $R^1$ is methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl or 4-pyridyl, more preferably, $R^1$ is methyl, ethyl, n-propyl, isopropyl, n-butyl, isobutyl, sec-butyl, tert-butyl, n-pentyl; isopentyl, sec-pentyl, neopentyl, 1,1-diethoxyethyl, phenyl, cyclohexyl or 3-pyridyl. In the above embodiments of a compound of Formula (I), $R^5$ is preferably substituted aryl, more preferably, substituted phenyl, most preferably, phenyl substituted with one or more halogen atoms.

In some embodiments of a compound of Formulae (I), (V) or (VI), $R^1$ is methyl, ethyl, n-propyl, isopropyl, n-butyl, isobutyl, sec-butyl, tert-butyl, n-pentyl, isopentyl, sec-pentyl, neopentyl, 1,1-dietlhoxyethyl, phenyl, cyclohexyl, 2-pyridyl, 3-pyridyl or 4-pyridyl, $R^2$ is hydrogen, methyl, ethyl, n-propyl, isopropyl, n-butyl, isobutyl, sec-butyl, phenyl or cyclohexyl, $R^3$ is hydrogen and $R^4$ is hydrogen. In other embodiments of compounds of Formulae (I), (V) or (VI), $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl or 4-pyridyl, $R^2$ is hydrogen, methyl, n-propyl, or isopropyl, $R^3$ is hydrogen and $R^4$ is hydrogen. In still other embodiments of compounds of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is hydrogen, methyl, n-propyl, or isopropyl, $R^3$ is hydrogen and $R^4$ is hydrogen.

In still other embodiments of compounds of Formulae (I), (V) or (VI), $R^1$ is methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl or 4-pyridyl, $R^2$ is methyl, methoxycarbonyl, ethoxycarbonyl, isopropoxycarbonyl or cyclohexyloxycarbonyl, $R^3$ is methyl and $R^4$ is hydrogen.

In some embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is hydrogen, $R^3$ is hydrogen and $R^4$ is hydrogen. In other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is methyl, $R^3$ is hydrogen and $R^4$ is hydrogen. In yet other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^1$ is n-propyl, $R^3$ is hydrogen and $R^4$ is hydrogen. In still other embodiments of a compound of Formulae (I), (V) or (VI), $R^1$ is methyl, ethyl, n-propyl, n-butyl, isobutyl, sec-butyl, tert-butyl, phenyl, cyclohexyl or 3-pyridyl, $R^2$ is isopropyl, $R^3$ is hydrogen and $R^4$ is hydrogen.

In some embodiments of a compound of Formula (I), $R^2$ and $R^3$ are different and the compound of Formula (I) is substantially one diastereomer. In other embodiments of a compound of Formula (I), the stereochemistry at the carbon to which $R^2$ and $R^3$ are attached is of the S-configuration and the compound of Formula (I) is substantially one diastereomer. In still other embodiments of a compound of Formula (I), the stereochemistry at the carbon to which $R^2$ and $R^3$ are attached is of the R-configuration, and the compound of Formula (I) is substantially one diastereomer. In some embodiments of a compound of Formula (I), $R^2$ is $C_{1-4}$ alkyl, $R^3$ is hydrogen and the compound of Formula (I) is substantially one diastereomer. In other embodiments of a compound of Formula (I), $R^2$ is $C_{1-4}$ alkyl, $R^3$ is hydrogen, the stereochemistry at the carbon to which $R^2$ and $R^3$ are attached is of the S-configuration and the compound of Formula (I) is substantially one diastereomer. In other embodiments of a compound of Formula (I), $R^2$ is $C_{1-4}$ alkyl, $R^3$ is hydrogen, the stereochemistry at the carbon to which $R^2$ and $R^3$ are attached is of the R-configuration, and the compound of Formula (I) is substantially one diastereomer.

In some embodiments of a compound of Formula (VI), $R^2$ and $R^3$ in the compound of Formula (VI) are different and the compound of Formula (VI) is substantially one diastereomer. In other embodiments of a compound of Formula (VI), the stereochemistry at the carbon to which $R^2$ and $R^3$ are attached is of the S-configuration and the compound of Formula (VI) is substantially one diastereomer. In other embodiments of a compound of Formula (VI), the stereochemistry at the carbon to which $R^2$ and $R^3$ are attached is of the R-configuration and the compound of Formula (VI) is substantially one diastereomer. In still other embodiments of a compound of Formula (VI), $R^2$ is $C_{1-4}$ alkyl, $R^3$ is hydrogen, and the compound of Formula (VI) is substantially one diastereomer. In still other embodiments of a compound of Formula (VI), $R^2$ is $C_{1-4}$ alkyl, $R^3$ is hydrogen, the stereochemistry at the carbon to which $R^2$ and $R^3$ are attached is of the S-configuration, and the compound of Formula (VI) is substantially one diastereomer. In still other embodiments of a compound of Formula (VI), $R^2$ is $C_{1-4}$ alkyl, $R^3$ is hydrogen, the stereochemistry at the carbon to which $R^2$ and $R^3$ are attached is of the R-configuration, and the compound of Formula (VI) is substantially one diastereomer.

In some embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is methyl, $R^3$ is hydrogen, $R^4$ is hydrogen, the stereochemistry at the carbon to which $R^2$ and $R^3$ are attached is of the S-configuration and the compound of Formulae (I), (V) or (VI) is substantially one diastereomer. In other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is methyl, $R^3$ is hydrogen, $R^4$ is hydrogen, the stereochemistry at the carbon to which $R^2$ and $R^3$ are attached is of the R-configuration and the compound of Formulae (I), (V) or (VI), is substantially one diastereomer. In still other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is n-propyl, $R^3$ is hydrogen, $R^4$ is hydrogen, the stereochemistry at the carbon to which $R^2$ and $R^3$ are attached is of the S-configuration, and the compound of Formulae (I), (V) or (VI), is substantially one diastereomer. In still other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is n-propyl, $R^3$ is hydrogen, $R^4$ is hydrogen, the stereochemistry at the carbon to which $R^2$ and $R^3$ are attached is of the R-configuration, and the compound of Formulae (I), (V) or (VI) is substantially one diastereomer. In still other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is isopropyl, $R^3$ is hydrogen, $R^4$ is hydrogen, the stereochemistry at the carbon to which $R^2$ and $R^3$ are attached is of the S-configuration and the compound of Formulae (I), (V) or (VI) is substantially one diastereomer. In other embodiments of a compound of Formulae (I), (V) or (VI), $R^1$ is methyl, ethyl, n-propyl, isopropyl, n-butyl, isobutyl, sec-butyl, tert-butyl, phenyl, cyclohexyl or 3-pyridyl, $R^2$ is isopropyl, $R^3$ is hydrogen, $R^4$ is hydrogen, the stereochemistry at the carbon to which $R^2$ and $R^3$ are attached is of the R-configuration and the compound of Formulae (I), (V) or (VI), is substantially one diastereomer. In still other embodiments of a compound of Formulae (I), (V) or (VI), $R^1$ is isopropyl, $R^2$ is isopropyl, $R^3$ is hydrogen, $R^4$ is hydrogen, the stereochemistry at the carbon to which $R^2$ and $R^3$ are attached is of the S-configuration, and the compound of Formulae (I), (V) or (VI) is substantially one diastereomer. In still other embodiments of a compound of Formulae (I), (V) or (VI), $R^1$ is isopropyl, $R^2$ is isopropyl, $R^3$ is hydrogen, $R^4$ is hydrogen, the stereochemistry at the carbon to which $R^2$ and $R^3$ are attached is of the R-configuration, and the compound of Formulae (I), (V) or (VI) is substantially one diastereomer.

In another aspect, a compound of Formula (II) is provided,

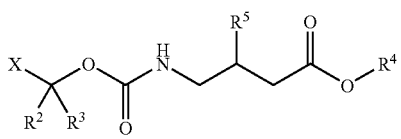

(II)

wherein:

X is fluoro, chloro, bromo or iodo;

$R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl and substituted heteroarylalkyl or optionally, $R^2$ and $R^3$ together with the carbon atom to which they are bonded form a cycloalkyl, substituted cycloalkyl, cycloheteroalkyl or substituted cycloheteroalkyl ring;

$R^4$ is selected from the group consisting of hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl; and $R^5$ is selected from the group consisting of substituted aryl, heteroaryl and substituted heteroaryl.

In some embodiments, $R^5$ is selected from the group consisting of 4-chlorophenyl;

R-(4-chlorophenyl), 2-chlorophenyl), 4-fluorophenyl, thien-2-yl, 5-chlorothien-2-yl, 5-bromothien-2-yl and 5-methylthien-2-yl.

In other embodiments, the compound of Formula (II) has the structure of Formula (VI):

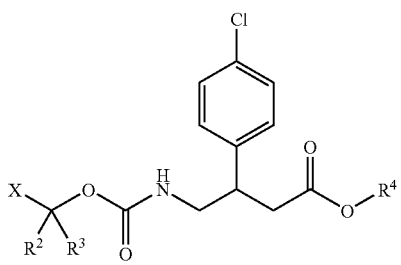

(VII)

or pharmaceutically acceptable salts, hydrates or solvates thereof;

wherein:

X, $R^2$, $R^3$ and $R^4$ are as previously defined, supra.

In still other embodiments, the compound of Formula (II) has the structure of Formula (VIII):

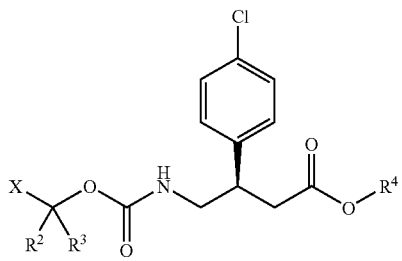

(VIII)

or pharmaceutically acceptable salts, hydrates or solvates thereof;

wherein:

X, $R^2$, $R^3$ and $R^4$ are as previously defined, supra.

In some embodiments of a compound of Formulae (II), (VII) or (VIII), X is chloro, bromo or iodo. In other embodiments of a compound of Formulae (II), (VII) or (VIII), X is chloro.

In still other embodiments of a compound of Formulae (II), (VII) or (VIII), $R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl. In still other embodiments of a compound of Formulae (II), (VII) or (VIII), $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl. In still other embodiments of a compound of Formulae (II), (VII) or (VIII), $R^2$ and $R^3$ are independently selected from the group consisting of hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl and 4-pyridyl. In still other embodiments of a compound of Formulae (II), (VII) or (VIII), $R^2$ is hydrogen, methyl, ethyl, n-propyl, isopropyl, n-butyl, isobutyl, sec-butyl, phenyl or cyclohexyl and $R^3$ is hydrogen. In still other embodiments of a compound of Formulae (II), (VII) or (VIII), $R^2$ is methyl, methoxycarbonyl, ethoxycarbonyl, isopropoxycarbonyl or cyclohexyloxycarbonyl and $R^3$ is methyl In still other embodiments of a compound of Formulae (II), (VII) or (VIII), $R^2$ and $R^3$ together with the carbon atom to which they are attached form a cycloalkyl, substituted cycloalkyl, cycloheteroalkyl or substituted cycloheteroalkyl ring. In still other embodiments of a compound of Formulae (II), (VII) or (VIII), $R^2$ and $R^3$ together with the carbon atom to which they are attached form a cyclobutyl, cyclopentyl or cyclohexyl ring.

In still other embodiments of a compound of Formulae (II), (VII) or (VIII), $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl. In still other embodiments of a compound of Formulae (II), (VII) or (VIII), $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl. In still other embodiments of a compound of Formulae (II), (VII) or (VIII), $R^4$ is hydrogen, allyl, benzyl or trimethylsilyl.

In still other embodiments, of a compound of Formulae (II), (VII) or (VIII), X is chloro, bromo or iodo, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl or 4-pyridyl, $R^3$ is hydrogen and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, cyclohexyl or phenyl, $R^3$ is hydrogen and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl.

In still other embodiments, of a compound of Formulae (II), (VII) or (VIII), X is chloro, bromo or iodo, $R^2$ is methyl, methoxycarbonyl, ethoxycarbonyl, isopropoxycarbonyl, or cyclohexyloxycarbonyl, $R^3$ is methyl and $R^4$ is selected from the group consisting of hydrogen, $C_{1-6}$ alkyl, substituted $C_{1-6}$ alkyl, $C_{3-6}$ cycloalkyl, phenyl, substituted phenyl, $C_{7-9}$ phenylalkyl, substituted $C_{7-9}$ phenylalkyl, trialkylsilyl and aryldialkylsilyl.

In still other embodiments, of a compound of Formulae (II), (VII) or (VIII), X is chloro, bromo or iodo, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl or 4-pyridyl, $R^3$ is hydrogen and $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, cyclohexyl or phenyl, $R^3$ is hydrogen and $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl.

In still other embodiments, of a compound of Formulae (II), (VII) or (VIII), X is chloro, bromo or iodo, $R^2$ is methyl, methoxycarbonyl, ethoxycarbonyl, isopropoxycarbonyl, or cyclohexyloxycarbonyl, $R^3$ is methyl and $R^4$ is hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl or phenyldimethylsilyl.

In still other embodiments, of a compound of Formulae (II), (VII) or (VIII), X is chloro, bromo or iodo, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen, allyl, benzyl or trimethylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl or 4-pyridyl, $R^3$ is hydrogen and $R^4$ is hydrogen, allyl, benzyl or trimethylsilyl.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, cyclohexyl or phenyl, $R^3$ is hydrogen and $R^4$ is hydrogen, allyl, benzyl or trimethylsilyl.

In still other embodiments, of a compound of Formulae (I), (VII) or (VIII), X is chloro, bromo or iodo, $R^2$ is methyl, methoxycarbonyl, ethoxycarbonyl, isopropoxycarbonyl, or cyclohexyloxycarbonyl, $R^3$ is methyl and $R^4$ is hydrogen, allyl, benzyl or trimethylsilyl.

In still other embodiments, of a compound of Formulae (II), (VII) or (VIII), X is chloro, bromo or iodo, $R^2$ and $R^3$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl and $R^4$ is hydrogen.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl or 4-pyridyl, $R^3$ is hydrogen and $R^4$ is hydrogen.

In still other embodiments, of a compound of Formulae (II), (VII) or (VIII), X is chloro, bromo or iodo, $R^2$ is hydrogen, methyl, ethyl, n-propyl, isopropyl, n-butyl, isobutyl, sec-butyl, cyclohexyl or phenyl, $R^3$ is hydrogen and $R^4$ is hydrogen.

In still other embodiments, of a compound of Formulae (II), (VII) or (VIII), X is chloro, bromo or iodo, $R^2$ is methyl, methoxycarbonyl, ethoxycarbonyl, isopropoxycarbonyl, or cyclohexyloxycarbonyl, $R^3$ is methyl and $R^4$ is hydrogen.

In still other embodiments of a compound of Formulae (II), (VII) or (VIII), X is chloro, bromo or iodo, $R^2$ is hydrogen, methyl, ethyl, n-propyl, isopropyl, n-butyl, isobutyl, sec-butyl, phenyl or cyclohexyl, $R^3$ is hydrogen and $R^4$ is hydrogen, allyl, benzyl or trimethylsilyl. In other embodiments of a compound of Formulae (II), (VII) or (VIII), X is chloro, bromo or iodo, $R^2$ is hydrogen, methyl, n-propyl, or isopropyl, $R^3$ is hydrogen and $R^4$ is hydrogen, allyl, benzyl or trimethylsilyl. In still other embodiments of a compound of Formulae (II), (VII) or (VIII), X is chloro, $R^2$ is hydrogen, methyl, n-propyl, or isopropyl, $R^3$ is hydrogen and $R^4$ is hydrogen, allyl, benzyl or trimethylsilyl.

In still other embodiments of a compound of Formulae (II), (VII) or (VIII), X is chloro, bromo or iodo, $R^2$ is methyl, methoxycarbonyl, ethoxycarbonyl, isopropoxycarbonyl or cyclohexyloxycarbonyl $R^3$ is methyl and $R^4$ is hydrogen, allyl, benzyl or trimethylsilyl.

Compounds of Formulae (II), (VII) and (VIII) are useful intermediates in the synthesis of compounds of Formulae (I), (VI) and (VII), as described in detail in Section 4.3 below.

4.3 Synthesis

The compounds disclosed herein may be obtained via the synthetic methods illustrated in Schemes 1-10. Those of ordinary skill in the art will appreciate that a preferred synthetic route to the disclosed compounds consists of attaching promoieties to baclofen or baclofen analogs. Numerous methods have been described in the art for the synthesis of baclofen and baclofen analogs (e.g., Keberle et al., U.S. Pat. No. 3,471,548; Keberle et al., U.S. Pat. No. 3,634,428; Krogsgaard-Larsen, *Med. Res. Rev.* 1988, 8, 27-56; Berthelot et al., *J. Med. Chem.* 1987, 30, 743-746; Berthelot et al., *J. Med. Chem.* 1991, 34, 2557-2560; Debaert et al., European Patent No. EP 0463969 B1). Methods for preparation of R-baclofen have also been described in the art (e.g., Witczuk et al., *Pol. J. Pharmacol. Pharm.* 1980, 32, 187-196; Chenevert et al., *Tetrahedron Lett.* 1991, 32, 4249-4250; Herdeis et al., *Tetrahedron Asymmetry* 1992, 3, 1213-1221; Hubmann et al., German Patent Application No. DE 4224342 A1; Yoshifuji et al., *Chem. Pharm. Bull.* 1995, 43, 1302-1306; Wildervanck et al., U.S. Pat. No. 6,051,734; Thakur et al., *Tetrahedron Asymmetry* 2003, 14, 581-586). Other prodrug (or related) derivatives of baclofen have been described in the art (e.g., Kaplan et al., U.S. Pat. No. 4,094,992; Mazaki et al., Jpn. Kokai Tokkyo Koho JP 01319466 A2; Castagnoli et al., International Publication No. WO98/22110; Guillon et al. *Pharm. Pharmacol. Commun.* 1999, 5, 243-247; Leisen et al., *Pharm. Res.* 2003, 20, 772-778; Mills, U.S. Pat. No. 5,773,592; Mills, U.S. Patent Appl. Publ. 2003/0228644). General synthetic methods useful in the synthesis of the compounds described herein are available in the art (e.g., Green et al., "Protective Groups in Organic Chemistry", (Wiley, $2^{nd}$ ed. 1991); Harrison et al., "Compendium of Synthetic Organic Methods", Vols. 1-8 (John Wiley and Sons, 1971-1996; Larock "Comprehensive Organic Transformations," VCH Publishers, 1989; and Paquette, "Encyclopedia of Reagents for Organic Synthesis," John Wiley & Sons, 1995).

Accordingly, starting materials useful for preparing compounds and intermediates thereof, and/or practicing methods described herein are commercially available or can be prepared by well-known synthetic methods. Other methods for synthesis of the prodrugs described herein are either described in the art or will be readily apparent to the skilled artisan in view of the references provided above and may be used to synthesize the compounds described herein. Accordingly, the methods presented in the Schemes herein are illustrative rather than comprehensive.

Intermediate (XI) useful in the preparation of 1-haloalkyl carbamates of Formula (II) may be generated according to reactions detailed in Scheme 1.

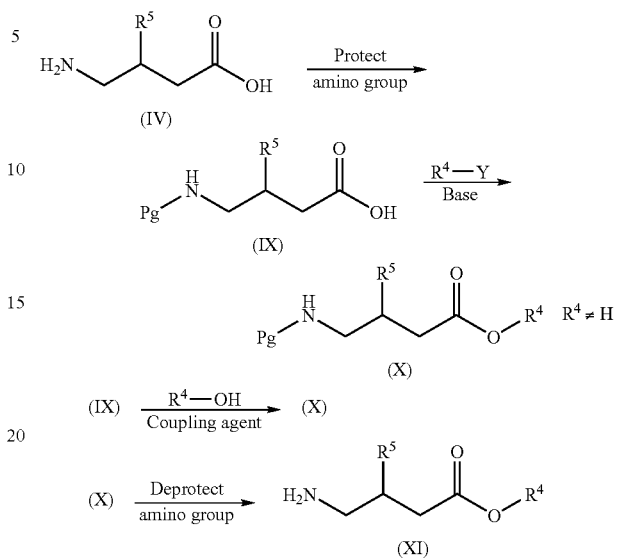

The amino group of (IV) is protected under standard conditions with a protecting group (Pg) to afford compound (IX). The carboxylic acid moiety in (IX) is esterified to yield compound (X), either via alkylation with $R^4$—Y, where Y is halide, —$OSO_2R'$ ($R'$ is alkyl, substituted alkyl, aryl or substituted aryl) or any other suitable leaving group or via condensation with alcohol $R^4$—OH under standard acylation conditions (e.g., in the presence of a coupling agent such as a carbodiimide, via an acyl halide, acid anhydride or other activated ester intermediate). Removal of the protecting group from (X) under standard deprotection conditions affords compound (XI). Preferably, the protecting group Pg is removable under acidic conditions and compound (XI) is isolated as a salt, which is stabilized against lactam formation relative to the corresponding free base. tert-Butoxycarbonyl (i.e., Boc) is one preferred protecting group, and may be removed with HCl to afford (XI) as a hydrochloride salt.

In some embodiments, the hydrochloride salt of (XI) is prepared directly from (IV) by treatment with an excess of thionyl chloride or hydrogen chloride gas and alcohol $R^4$—OH (Scheme 2). Typical ratios of (IV) to thionyl chloride from between about 1:1 and about 1:20, and ratios of (IV) to alcohol from between about 1:1 and about 1:20 may be used. The reaction may be performed at temperatures between about −20° C. and about 25° C. The alcohol may be used as a solvent for the reaction under conditions where $R^4$—OH is a liquid. Alternatively, the reaction may be performed in a suitable solvent, such as dichloromethane, dichloroethane, chloroform, toluene, dimethylformamide, dimethylacetamide, N-methylpyrrolidinone, pyridine or combinations thereof. Preferred alcohols $R^4$—OH for this reaction include arylalkyl, substituted arylalkyl and allylic alcohols. Allyl alcohol and benzyl alcohol are particularly preferred.

Scheme 2

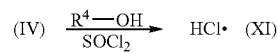

In some embodiments, a compound of Formula (II) is prepared by acylation of (XI) with compound (XII) (see Scheme 3), where X is halide and Z is a leaving group (e.g., halide, p-nitrophenolate, imidazolyl, etc.). In other embodiments, X is Cl, Br or I and Z is Cl. In yet other embodiments, X and Z are both Cl. The acylation reaction may be performed in the presence of a inorganic base or an organic base (e.g., tertiary amine bases, such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo[5.4.0]undec-7-ene or 1,5-diazabicyclo [4.3.0]undec-7-ene or combinations thereof) or combinations thereof. Suitable solvents for acylation include, but are not limited to, dichloromethane, dichloroethane, chloroform, toluene, dimethylformamide, dimethylacetamide, N-methylpyrrolidinone, dimethyl sulfoxide, pyridine, ethyl acetate, isopropyl acetate, acetonitrile, acetone, 2-butanone, methyl tert-butyl ether or combinations thereof. Alternatively, biphasic solvent mixtures comprising water and including one or more of dichloromethane, dichloroethane, chloroform, toluene, ethyl acetate, isopropyl acetate or methyl tert-butyl ether, may be utilized. Typical temperatures for performing this reaction are between about −20° C. and about 50° C., more preferably between about −20° C. and about 25° C.

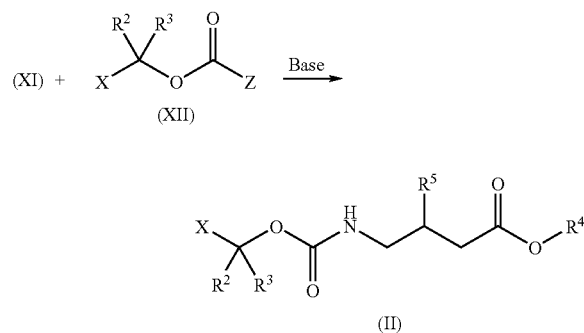

Scheme 3

In other embodiments, a compound of Formula (II), where $R^4$ is trialkylsilyl or aryldialkylsilyl, may be prepared directly from compound (IV) by silylation (e.g., using a silyl halide or silylamide reagent) followed by acylation of the resulting intermediate with compound (XII) (see Scheme 4). Suitable solvents for performing this reaction include, but are not limited to, dichloromethane, dichloroethane, chloroform, toluene, pyridine, acetonitrile or combinations thereof. Suitable bases for performing this reaction include but are not limited to, triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo [5.4.0]undec-7-ene, 1,5-diazabicyclo[4.3.0]undec-7-ene or combinations thereof. Typical temperatures for performing this reaction are between about −78° C. and about 50° C., more preferably between about −20° C. and about 25° C.

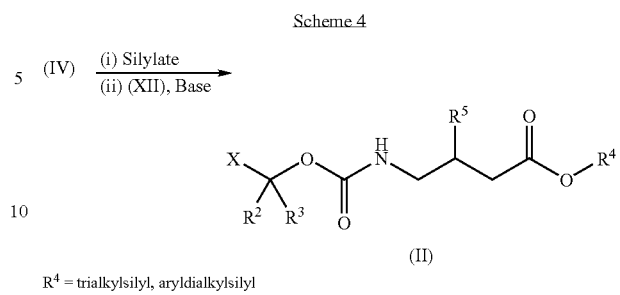

Scheme 4

$R^4$ = trialkylsilyl, aryldialkylsilyl

In still other embodiments, 1-acyloxylalkyl carbamates of Formula (I) are prepared from compounds of Formula (II) by treatment with carboxylic acids of Formula (III) in the presence of an organic or inorganic base, or other metal salt, as illustrated in Scheme 5.

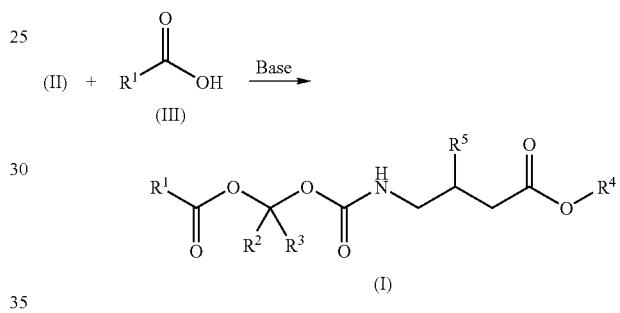

Scheme 5

Those of skill in the art will appreciate that the following embodiments, infra, refer to compounds of Formulae (I), (II) and (III). In some embodiments, the ratio of the compound of Formula (II) to the compound of Formula (III) is between about 1:1 and 1:20. In other embodiments, the ratio of the compound of Formula (II) to the compound of Formula (III) is between about 1:1 and 1:5. In still other embodiments, the ratio of the compound of Formula (II) to the compound of Formula (III) is about 1:1.

In some embodiments, the compounds of Formulae (II) and (III) and the metal salt are contacted with a solvent. In other embodiments, the ratio of the compound of Formula (II) to the compound of Formula (III) is between about 1:1 and 1:20. In still other embodiments, the ratio of the compound of Formula (II) to the compound of Formula (III) is between about 1:1 and 1:5. In still other embodiments, the ratio of the compound of Formula (II) to the compound of Formula (III) is about 1:1. In some embodiments, the solvent is dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide or combinations thereof. In other embodiments, the metal is Ag, Hg, Na, K, Li, Cs, Ca, Mg or Zn.

In some embodiments, the compounds of Formulae (II) and (III) and the organic base are contacted with a solvent. In other embodiments, the ratio of the compound of Formula (II) to the compound of Formula (III) is between about 1:1 and 1:20. In still other embodiments, the ratio of the compound of Formula (II) to the compound of Formula (III) is between about 1:15 and 1:20. In still other embodiments, the ratio of the compound of Formula (II) to the compound of Formula (III) is about 1:10. In still other embodiments, the ratio of the compound of Formula (II) to the compound of Formula (III) is between about 1:1 and 1:5. In still other embodiments, the ratio of the compound of Formula (II) to the compound of Formula II) is about 1:1. In some embodiments, the solvent is dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide or combinations thereof. In other embodiments, the organic base is triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo [5.4.0]undec-7-ene, 1,5-diazabicyclo[4.3.0]undec-7-ene or combinations thereof.

In some embodiments, the compound of Formula (III) is a liquid under the conditions of said contacting, the compound of Formula (III) further serving as a solvent for the reaction with the compound of Formula (II). In other embodiments, the compound of Formula (III) is acetic acid, methoxyacetic acid, ethoxyacetic acid, propionic acid, butyric acid, isobutyric acid, pivalic acid, valeric acid, isovaleric acid, 2-methylbutyric acid, cyclobutanecarboxylic acid, cyclopentanecarboxylic acid or cyclohexanecarboxylic acid.

In some embodiments, the compound of Formula (II), the compound of Formula (III) and the metal salt are contacted at a temperature between about −25° C. and about 120° C. In other embodiments, the temperature is between about 0° C. and about 25° C.

In still some other embodiments, the compound of Formula (II), the compound of Formula (III) and the organic base are contacted at a temperature between about −25° C. and about 120° C. In other embodiments, the temperature is between about 0° C. and about 25° C.

In some embodiments, the compound of Formula (II), the compound of Formula (III) and the organic base are contacted with a catalytic amount of an iodide salt. In still other embodiments, the iodide salt is sodium iodide, potassium iodide, tetramethylammonium iodide, tetraethylammonium iodide or tetrabutylammonium iodide.

In some embodiments, $R^4$ is a carboxylic acid protecting group that can be removed under mild conditions to provide a compound of Formula (I) where $R^4$ is hydrogen. Carboxylic acid protecting groups removable via mild acidic hydrolysis, fluoride ion-promoted hydrolysis, catalytic hydrogenolysis, transfer hydrogenolysis, or other transition metal-mediated deprotection reactions are preferred. In some embodiments, $R^4$ is trimethylsilyl, allyl or benzyl.

In still other embodiments compounds of Formula (I) are prepared as illustrated in Scheme 6.

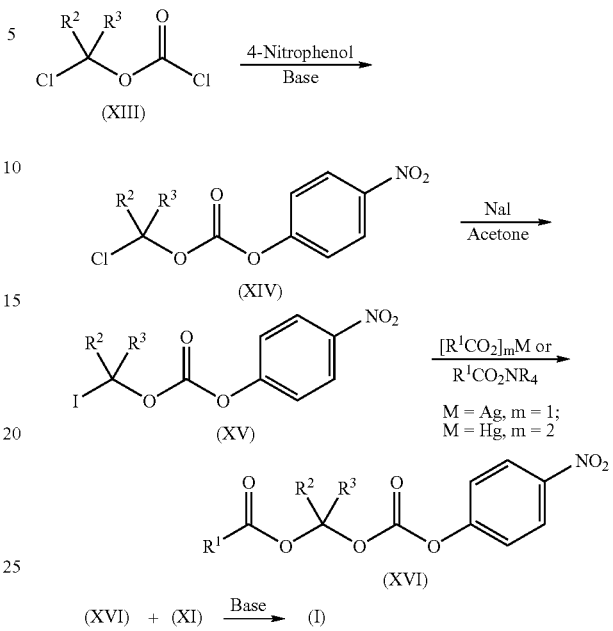

Chloroformate (XIII) is treated with an aromatic leaving group such as p-nitrophenol in the presence of base to provide p-nitrophenylcarbonate (XIV). Halide interchange provides iodide (XV), which is reacted with a metal or tetraalkylammonium salt of a carboxylic acid to afford compound (XVI). Treatment of (XVI) with baclofen analog derivative (XI), optionally, in the presence of trimethylsilyl chloride, affords a compound of Formula (I). Methods for making related acyloxyalkyl carbamate compounds have been described in the art (Alexander, U.S. Pat. No. 4,760, 057; Alexander, U.S. Pat. No. 4,916,230; Alexander, U.S. Pat. No. 5,466,811; Alexander, U.S. Pat. No. 5,684,018).

Another method for synthesis of compounds of Formula (I) proceeds via carbonylation of baclofen analog derivative (XI) to an intermediate carbamic acid species, which is captured by an in situ alkylation reaction in an adaptation of methods disclosed in the art (Butcher, *Synlett* 1994, 825-6; Ferres et al., U.S. Pat. No. 4,036,829). Carbon dioxide gas is bubbled into a solution containing (XI) and a base (e.g., $Cs_2CO_3$, $Ag_2CO_3$ or AgO) in a solvent such as DMF or NMP. The activated halide is added, optionally, in the presence of iodide ion as a catalyst, and the carbonylation continued until the reaction is completed. This method is illustrated in Scheme 7 for the preparation of compounds of Formula (I) from halide (XVII).

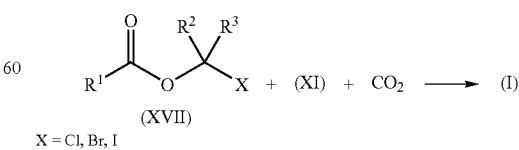

Yet another method for synthesis of compounds of Formula (I) relies upon oxidation of ketocarbamate derivatives of baclofen and baclofen analogs (e.g., Gallop et al., U.S. Patent Appl. Publ. 2003/0171303; and Bhat et al., U.S. patent application Ser. No. 10/893,130 entitled "Methods for Synthesis of Acyloxyalkyl Compounds"). As illustrated in Scheme 8, oxidation of ketocarbamate (XVIII) affords a compound of Formula (I). Methods for synthesis of compounds of Formula (XVIII) are disclosed in the pending applications, supra. Typical oxidants include those, which have been successfully used in Baeyer-Villager oxidations of ketones to esters or lactones (Strukul, *Angnew. Chem. Int. Ed.* 1998, 37, 1198; Renz et al., *Eur. J. Org. Cheer.* 1999, 737; Beller et al., in "Transition Metals in Organic Synthesis" Chapter 2, Wiley VCH; Stewart, *Current Organic Chemistry*, 1998, 2, 195; Kayser et al., *Synlett* 1999, 1, 153). The use of anhydrous oxidants may be beneficial since prodrugs (I) may be labile. Thus, performing the oxidation under anhydrous reaction conditions may avoid hydrolysis of the reactive products.

Scheme 8

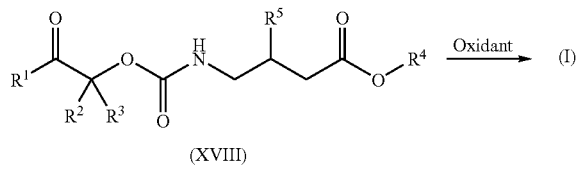

(XVIII)

Preferably, the oxidation is performed in the liquid phase, more preferably, in the presence of a solvent. Choosing a solvent for oxidation of a compound of Formula (XVIII) is well within the ambit of one of skill in the art. Generally, a useful solvent will dissolve, at least partially, both the oxidant and the compound of Formula (XVIII) and will be inert to the reaction conditions. Preferred solvents are anhydrous and include, but are not limited to, dichloromethane, dichloroethane, chloroform, ethyl acetate, isopropyl acetate, toluene, chlorobenzene, xylene, acetonitrile, diethyl ether, methyl tert-butyl ether, acetic acid, cyclohexane and hexanes. Mixtures of the above solvents may also be used in the oxidation of a compound of Formula (XVIII) to a compound of Formula (I).

In some embodiments, the anhydrous oxidant is an anhydrous peroxyacid generated in situ by reaction of the urea-hydrogen peroxide complex (4) ("UHP") with a carboxylic acid anhydride. In other embodiments, the anhydrous oxidant is an anhydrous peroxysulfonic acid generated in situ by reaction of the urea-hydrogen peroxide complex (4) with a sulfonic acid anhydride. The UHP complex serves as a source of anhydrous hydrogen peroxide and has been used in a variety of oxidative transformations in anhydrous organic solvents (Cooper et al., *Synlett.* 1990, 533-535; Balicki et al., *Synth. Commun.* 1993, 23, 3149; Astudillo et al., *Heterocycles* 1993, 36, 1075-1080; Varma et al., *Organic Lett.* 1999, 1, 189-191). However, other suitable sources of anhydrous hydrogen peroxide may also be used in the reaction instead of the UHP-complex (e.g., the 1,4-diazabicyclo[2.2.2]octane-hydrogen peroxide complex).

A useful oxidant is anhydrous peroxytrifluoroacetic acid, generated in situ by reacting the UHP-complex with trifluoroacetic anhydride (Cooper et al., *Synlett.* 1990, 533-535; Benjamin, et al., *J. Am. Chem. Soc.* 2002, 124, 827-833). Anhydrous peroxycarboxylic acids (XX) may generally be prepared by treating carboxylic acid anhydrides with anhydrous hydrogen peroxide, more preferably, with the UHP-complex (4). Similarly, anhydrous peroxysulfonic acids (XXII) may be prepared by reacting sulfonic acid anhydrides (XXI) with anhydrous hydrogen peroxide, preferably, with the UHP-complex (4). The preparation of anhydrous peroxycarboxylic acids (XX) and the peroxysulfonic acids (XXII) is illustrated in Scheme 9.

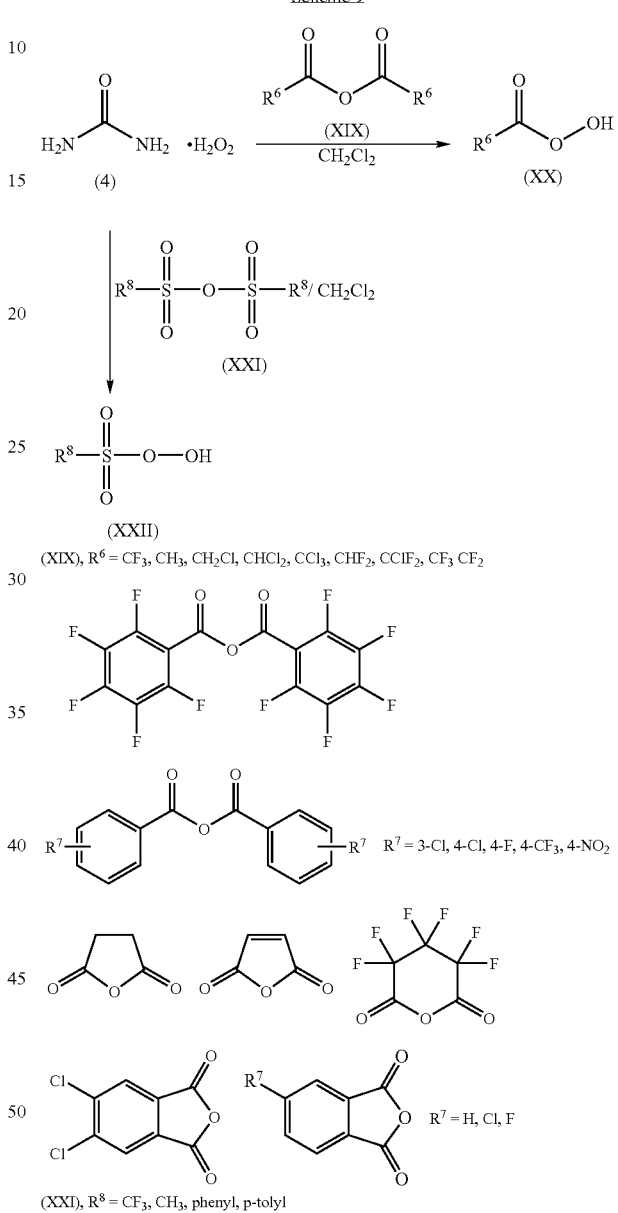

The UHP-complex (4) and a carboxylic acid anhydride (XIX) or a sulfonic acid anhydride (XXI) are reacted in dichloromethane or other suitable solvent at temperatures ranging from about −25° C. to about 100° C. to generate the anhydrous peroxyacids. The peroxyacids may be generated first and subsequently reacted with the ketocarbamate (XVIII). In some embodiments, a carboxylic acid anhydride is added to a stirred suspension or solution containing the UHP-complex and (XVIII) to generate the peroxycarboxylic acid, which reacts in situ with (XVIII) to give compound (I). In other embodiments, the molar ratio of UHP-complex and the acid anhydride is about 6:1. In still other embodiments, the molar ratio of UHP-complex and acid anhydride (XIX) is between about 5:1 and about 1:1. In yet other embodiments, the molar ratio of UHP-complex and acid anhydride (XIX) is between about 2:1 and about 1:1.

In some embodiments, the molar ratio of the peroxyacid oxidant to the compound of Formula (XVIII) is between about 8:1 and about 1:1. In other embodiments, the molar ratio of the peroxyacid oxidant to the compound of Formula (XVIII) is between about 4:1 and about 1:1: In yet other embodiments, the molar ratio of the peroxyacid oxidant to the compound of Formula (XVIII) is between about 2:1 and about 1:1. Preferably, when the oxidant is peroxytrifluoroacetic acid or another substituted peroxyacetic acid, the molar ratio of the peroxyacid oxidant to the compound of Formula (XVIII) is about 2:1.

Further, the use of additives in the oxidation of a compound of Formula (XVIII) to a compound of Formula (I) is also contemplated. While not wishing to be bound by theory, additives may either catalyze the reaction or stabilize the final product or both. In some embodiments, a Lewis acid or a protic acid or any combination of Lewis acid or protic acid may be used in the oxidation of a compound of Formula (XVIII) (preferably, in the presence of a solvent). Lewis acids include, but are not limited to, $BF_3$, $SeO_2$, $MeReO_3$, $MnO_2$, $SnCl_4$, $Sc(OTf)_3$, $Ti(O-iPr)_4$, $Al_2O_3$ and $Fe_2O_3$. Protic acids include, but are not limited to, trifluoroacetic acid, acetic acid, p-toluenesulfonic acid, methanesulfonic acid, trifluoromethanesulfonic acid, hydrochloric acid and sulfuric acid. While not wishing to be bound by theory, the Lewis acid and/or protic acid may catalyze oxidation by increasing the electrophilicity of the carbonyl group in Formula (XVIII).

In other embodiments, the oxidation may be conducted in the presence of an anhydrous base. While not wishing to be bound by theory, the base may stabilize acid sensitive products by reacting with acidic by products formed during oxidation.

Generally, the temperature of the reaction may be readily optimized by methods known to those of ordinary skill in the art. Preferably, the oxidation of a compound of Formula (XVIII) is carried out at a temperature between about −25° C. and about 100° C. (more preferably, between about 0° C. and about 25° C.).

An advantageous feature of this method of synthesis of compounds of Formula (I) is that oxidation of ketocarbamate derivatives (XVIII) proceeds stereospecifically, with retention of configuration at the carbon atom initially adjacent to the carbonyl group in ketone (XVIII). This may be exploited in a stereoselective synthesis of prodrug derivatives. For example, the chiral R-baclofen prodrug 4-{[(1S)-isobutanoyloxyethoxy]carbonylamino}-(3R)-(4-chlorophenyl)-butanoic acid (34) may be synthesized as a single diastereomer by stereoselective oxidation of 4-{[(1S)-isobutanoylethoxy]carbonylamino}-(3R)-(4-chlorophenyl)-butanoic acid (35) as described in Example 30 of Section 5 below. Acyloxyalkyl prodrugs of other baclofen analogs may be amenable to synthesis from the appropriate ketocarbamate derivatives via Baeyer-Villiger type oxidation, provided that they do not contain chemical functionality susceptible to decomposition or other transformation under conditions of the reaction.

Another method for synthesis of compounds of Formula (I), illustrated in Scheme 10, relies upon reaction of compounds of Formulae (IV) or (XI) with a 1-(acyloxy)-alkyl N-hydroxysuccinimidyl carbonate compound of Formula (XXIII), as described in the co-pending application Gallop et al., U.S. Provisional Patent Application Ser. No. 60/606,637 entitled "Methods for Synthesis of Acyloxyalkyl Carbamate Prodrugs," filed Aug. 13, 2004).

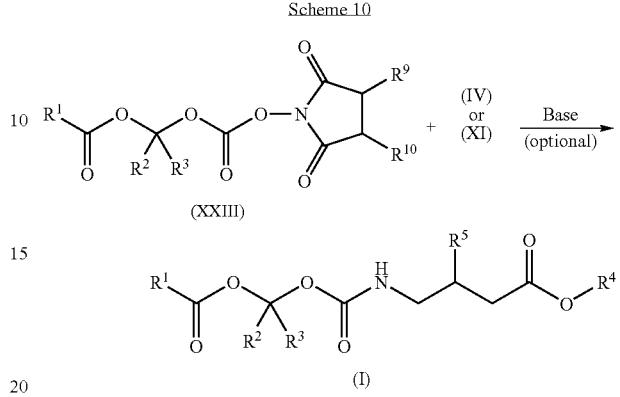

wherein $R^9$ and $R^{10}$ are independently hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, sulfonamido, or optionally, $R^9$ and $R^{10}$ together with the atoms to which they are attached form a substituted cycloalkyl, substituted cycloheteroalkyl or substituted aryl ring and $R^1$ to $R^5$ are as described in Section 4.2.

In some embodiments of the method described in Scheme 10 for synthesizing a compound of Formula (I), $R^2$ and $R^3$ in the compound of Formula (XXIII) are different, such that the carbon atom to which these substituents are attached is a stereogenic center.

In some embodiments of the method described in Scheme 10 for synthesizing a compound of Formula (I), $R^9$ and $R^{10}$ in the compound of Formula (XXIII) are each benzoyloxy, the stereochemistry at the carbon to which $R^9$ is attached is of the R-configuration, and the stereochemistry at the carbon to which $R^{10}$ is attached is of the R-configuration. In other embodiments of the method described in Scheme 10 for synthesizing a compound of Formula (I), $R^9$ and $R^{10}$ in the compound of Formula (XXIII) are each benzoyloxy, the stereochemistry at the carbon to which $R^9$ is attached is of the S-configuration and the stereochemistry at the carbon to which $R^{10}$ is attached is of the S-configuration.

In some embodiments of the methods for synthesizing a compound of Formula (I), $R^2$ and $R^3$ in the compound of Formula (I) are different and the compound of Formula (I) is substantially one diastereomer. In some embodiments of the method described in Scheme 10 for synthesizing a compound of Formula (I), $R^1$ is isopropyl, $R^2$ is isopropyl, $R^3$ is hydrogen, the stereochemistry at the carbon to which $R^2$ and $R^3$ are attached is of the S-configuration and the compound of Formula (I) is substantially one diastereomer. In still other embodiments of the method of Scheme 10 for synthesizing a compound of Formula (I), $R^1$ is isopropyl, $R^2$ is isopropyl, $R^3$ is hydrogen, the stereochemistry at the carbon to which $R^2$ and $R^3$ are attached is of the R-configuration, and the compound of Formula (I) is substantially one diastereomer.

In some embodiments of the method of Scheme 10 for synthesizing a compound of Formula (I), $R^1$ is $C_{1-6}$ alkyl, $R^2$ is hydrogen or $C_{1-4}$ alkyl, $R^3$ is hydrogen, $R^4$ is hydrogen, $R^5$ is 4-chlorophenyl, $R^9$ and $R^{10}$ are each benzoyloxy, and the stereochemistry at the carbon to which $R^5$ is attached is of the R-configuration. In still other embodiments of the method of Scheme 10 for synthesizing a compound of Formula (I), $R^1$ is isopropyl, $R^2$ is isopropyl, $R^3$ is hydrogen, $R^4$ is hydrogen, $R^5$ is 4-chlorophenyl, $R^9$ and $R^{10}$ are each benzoyloxy, and the stereochemistry at the carbon to which $R^5$ is attached is of the R-configuration.

In still other embodiments of the method of Scheme 10 for synthesizing a compound of Formula (I), $R^1$ is isopropyl, $R^2$ is isopropyl, $R^3$ is hydrogen, $R^4$ is hydrogen, $R^5$ is 4-chlorophenyl, $R^9$ and $R^{10}$ are each benzoyloxy, the stereochemistry at the carbon to which $R^2$ and $R^3$ are attached is of the S-configuration, the stereochemistry at the carbon to which $R^5$ is attached is of the R-configuration, the stereochemistry at the carbon to which $R^9$ is attached is of the R-configuration, and the stereochemistry at the carbon to which $R^{10}$ is attached is of the R-configuration. In still other embodiments of the method of Scheme 10 for synthesizing a compound of Formula (I), $R^1$ is isopropyl, $R^2$ is isopropyl, $R^3$ is hydrogen, $R^4$ is hydrogen, $R^5$ is 4-chlorophenyl, $R^9$ and $R^{10}$ are each benzoyloxy, the stereochemistry at the carbon to which $R^2$ and $R^3$ are attached is of the R-configuration, the stereochemistry at the carbon to which $R^5$ is attached is of the R-configuration, the stereochemistry at the carbon to which $R^9$ is attached is of the S-configuration and the stereochemistry at the carbon to which $R^{10}$ is attached is of the S-configuration.

In some embodiments, the method of Scheme 10 is carried out in a solvent. Useful solvent include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water or combinations thereof. Preferably, the solvent is acetone, acetonitrile, dichloromethane, toluene, tetrahydrofuran, pyridine, methyl tert-butyl ether, methanol, ethanol, isopropanol, water, or combinations thereof. In some embodiments, the solvent is a mixture of acetonitrile and water. In other embodiments, the solvent is a mixture of acetonitrile and water, with a volume ratio of acetonitrile to water from about 1:5 to about 5:1. In still other embodiments, the solvent is a mixture of methyl tert-butyl ether and water. In still other embodiments, the solvent is a mixture of methyl tert-butyl ether and water, with a volume ratio of methyl tert-butyl ether to water from about 20:1 to about 2:1. In still other embodiments, the solvent is a mixture of methyl tert-butyl ether and water, wherein the methyl tert-butyl ether contains from about 10% to about 50% acetone by volume. In still other embodiments, the solvent is dichloromethane, water or a combination thereof. In still other embodiments, the solvent is a biphasic mixture of dichloromethane and water. In still other embodiments, the solvent is a biphasic mixture of dichloromethane and water containing from about 0.001 equivalents to about 0.1 equivalents of a phase transfer catalyst. Preferably, the phase transfer catalyst is a tetraalkylammonium salt, more preferably, the phase transfer catalyst is a tetrabutylammonium salt.

The method of Scheme 10 is preferably carried out a temperature between about −20° C. and about 40° C. In some embodiments, the temperature is between about −20° C. and about 25° C. In other embodiments, the temperature is between about 0° C. and about 25° C. In still other embodiments, the temperature is between about 25° C. and about 40° C.

In some embodiments of the method of Scheme 10, the reaction is performed in the absence of a base.

In other embodiments of the method of Scheme 10, the reaction is performed in the presence of an inorganic base. In some embodiments, the reaction is performed in the presence of an alkali metal bicarbonate or alkali metal carbonate salt. In other embodiments, the reaction is performed in the presence of sodium bicarbonate.

In still other embodiments of the method of Scheme 10, the reaction is performed in the presence of an organic base. Preferably, the reaction is performed in the presence of triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo[5.4.0]undec-7-ene or 1,5-diazabicyclo[4.3.0]undec-7-ene, more preferably, the reaction is performed in the presence of triethylamine, diisopropylethylamine, N-methylmorpholine, or pyridine.

4.4 Pharmaceutical Compositions

Pharmaceutical compositions comprising a therapeutically effective amount of one or more baclofen or baclofen analog prodrug compounds of Formulae (I), (V) or (VI), preferably in purified form, together with a suitable amount of a pharmaceutically acceptable vehicle, so as to provide a form for proper administration to a patient are provided herein. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In some embodiments, compositions are formulated for oral delivery, particularly for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

When a compound of Formulae (I), (V) or (VI) is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases, and tend to be more soluble in aqueous and other protic solvents than the corresponding free acid form. In some embodiments, sodium salts of a compound of Formulae (I), (V) or (VI) are used in the above described formulations.

4.5 Sustained Release Oral Dosage Forms

The disclosed compounds can be used with a number of different dosage forms, which may be adapted to provide sustained release of a compound of Formulae (I), (V) or (VI) upon oral administration.

In some embodiments, the dosage form comprises beads that on dissolution or diffusion release a compound disclosed herein over an extended period of hours, preferably, over a period of at least 6 hours, more preferably, over a period of at least 8 hours and most preferably, over a period of at least 12 hours. The beads may have a central composition or core comprising a compound disclosed herein and pharmaceutically acceptable vehicles, including an optional lubricant, antioxidant and buffer. The beads may be medical preparations with a diameter of about 0.05 mm to about 2 mm. Individual beads may comprise doses of a compound disclosed herein, for example, doses of up to about 40 mg of compound. The beads, in some embodiments, are formed of non-cross-linked materials to enhance their discharge from the gastrointestinal tract. The beads may be coated with a release rate-controlling polymer that gives a timed release profile.

The time-release beads may be manufactured into a tablet for therapeutically effective administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, *Int. J. Pharm.*, 1994, 112, 117-124; Pharmaceutical Sciences by Remington, $14^{th}$ ed, pp 1626-1628 (1970); Fincher, *J. Pharm. Sci.* 1968, 57, 1825-1835; and U.S. Pat. No. 4,083,949) as has the manufacture of tablets (Pharmaceutical Sciences, by Remington, $17^{th}$ Ed, Ch. 90, pp 1603-1625 (1985).

One type of sustained release oral dosage formulation that may be used with the disclosed compounds comprises an inert core, such as a sugar sphere, coated with an inner drug-containing layer and an outer membrane layer controlling drug release from the inner layer. A "sealcoat" may be provided between the inert core and the layer containing the active ingredient. When the core is of a water-soluble or water-swellable inert material, the sealcoat is preferably in the form of a relatively thick layer of a water-insoluble polymer. Such a controlled release bead may thus comprise: (i) a core unit of a substantially water-soluble or water-swellable inert material; (ii) a first layer on the core unit of a substantially water-insoluble polymer; (iii) a second layer covering the first layer and containing an active ingredient; and (iv) a third layer on the second layer of polymer effective for controlled release of the active ingredient, wherein the first layer is adapted to control water penetration into the core.

Usually, the first layer (ii) above constitutes more than about 2% (w/w) of the final bead composition, preferably, more than about 3% (w/w), e.g., from about 3% to about 80% (w/w). The amount of the second layer (ii) above usually constitutes from about 0.05% to about 60% (w/w), preferably from about 0.1% to about 30% (w/w) of the final bead composition. The amount of the third layer (iv) above usually constitutes from about 1% to about 50% (w/w), preferably, from about 2% to about 25% (w/w) of the final bead composition. The core unit typically has a size in the range of from about 0.05 to about 2 mm. The controlled release beads may be provided in a multiple unit formulation, such as a capsule or a tablet.

The cores are preferably of a water-soluble or swellable material and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose. The substantially water-insoluble material in the first, or sealcoat layer is generally a "GI insoluble" or "GI partially insoluble" film forming polymer (dispersed or dissolved in a solvent). Examples include, but are not limited to, ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D) and silicone elastomers. Usually, a plasticizer is used together with the polymer. Exemplary plasticizers include, but are not limited to, dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides). The second layer containing the active ingredient may be comprised of the active ingredient with or without a polymer as a binder. The binder, when used, is usually hydrophilic but may be water-soluble or water-insoluble. Exemplary polymers that may be used in the second layer containing the active drug are hydrophilic polymers such as, for example, polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w). Suitable polymers for use in the third layer, or membrane, for controlling the drug release may be selected from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above. Optionally, the controlled release layer comprises, in addition to the polymers above, other substance(s) with different solubility characteristics, to adjust the permeability and thereby the release rate, of the controlled release layer. Exemplary polymers that may be used as a modifier together with, for example, ethyl cellulose include, but are not limited to, HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

The preparation of the multiple unit formulation comprises the additional step of transforming the prepared beads into a pharmaceutical formulation, such as by filling a predetermined amount of the beads into a capsule, or compressing the beads into tablets. Examples of multi-particulate sustained release oral dosage forms are described in, for example, U.S. Pat. Nos. 6,627,223 and 5,229,135.

In other embodiments, an oral sustained release pump may be used (see Langer, supra; Sefton, 1987, *CRC Crit Ref Biomed. Eug.* 14:201; Saudek et al., 1989, *N. Engl. J. Med.* 321:574).

In still other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25.351; Howard et al., 1989, *J. Neurosurg.* 71:105). In some embodiments, polymeric materials are used for oral sustained release delivery. Polymers include, but are not limited to, sodium carboxymethylcellulose, hydroxypropylcellulose, hydroxypropylmethylcellulose and hydroxyethylcellulose (especially, hydroxypropylmethylcellulose). Other cellulose ethers have been described (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2, 307).

In other embodiments, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. An example is when solid microparticles of a compound disclosed herein are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained compound-releasing waxes are disclosed in Cain et al., U.S. Pat. No. 3,402,240 (caranuba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., *Drug Dev. Ind. Pharm.*, 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In other embodiments, a controlled-release system can be placed in proximity of the target of a compound disclosed herein (e.g., within the spinal cord), thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

In other embodiments, the dosage form comprises a compound disclosed herein coated on a polymer substrate. The polymer can be an erodible, or a nonerodible polymer. The coated substrate may be folded onto itself to provide a bilayer polymer drug dosage form. For example, a compound disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense a compound disclosed herein over a sustained release period. Representative biodegradable polymers comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly (dihydropyrans), and poly(dioxinones) which are known in the art (Rosoff, *Controlled Release of Drugs* Chap. 2, pp. 53-95 (1989); and in U.S. Pat. Nos. 3,811,444; 3,962,414; 4,066,747, 4,070,347; 4,079,038; and 4,093,709).

In other embodiments, the dosage form comprises a compound disclosed herein loaded into a polymer that releases the compound by diffusion through a polymer, or by flux through pores or by rupture of a polymer matrix. The drug delivery polymeric dosage form comprises between about 10 mg to 500 mg of compound homogenously contained in or on a polymer. The dosage form comprises at least one exposed surface at the beginning of dose delivery. The non-exposed surface, when present, is coated with a pharmaceutically acceptable material impermeable to the passage of a compound. The dosage form may be manufactured by procedures known in the art. An example of providing a dosage form comprises blending a pharmaceutically acceptable carrier like polyethylene glycol, with a known dose of a compound at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form are selected from the group consisting of olefinic polymers, vinyl polymers, addition polymers, condensation polymers, carbohydrate polymer and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., *Polymers* 1990, 31, 1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; and U.S. Pat. No. 3,992,518).

In other embodiments, the dosage from comprises a plurality of tiny pills. The tiny time-release pills provide a number of individual doses for providing various time doses for achieving a sustained-release prodrug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matrix comprises a plurality of 4 to 50 tiny pills, each tiny pill comprise a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of a compound. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in U.S. Pat. Nos. 4,434,153; 4,721,613; 4,853,229; 2,996,431; 3,139,383 and 4,752,470.

In still other embodiments, the dosage form comprises an osmotic dosage form, which comprises a semipermeable wall that surrounds a therapeutic composition comprising the compound. In use within a patient, the osmotic dosage form comprising a homogeneous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained compound release. These delivery platforms can provide an essentially zero order delivery profile as opposed to the spiked profiles of immediate release formulations.

In still other embodiments, the dosage form comprises another osmotic dosage form comprising a wall surrounding a compartment, the wall comprising a semipermeable polymeric composition permeable to the passage of fluid and substantially impermeable to the passage of compound present in the compartment, a compound-containing layer composition in the compartment, a hydrogel push layer composition in the compartment comprising an osmotic formulation for imbibing and absorbing fluid for expanding in size for pushing the compound composition layer from the dosage form, and at least one passageway in the wall for releasing the prodrug composition. The method delivers the compound by imbibing fluid through the semipermeable wall at a fluid imbibing rate determined by the permeability of the semipermeable wall and the osmotic pressure across the semipermeable wall causing the push layer to expand, thereby delivering the compound from the dosage form through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight, which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxyethylcellulose) in present manufacture; 1 mg to 50 mg of an agent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall comprises a composition that is permeable to the passage of fluid and impermeable to the passage of prodrug. The wall is nontoxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkycellulose such as hydroxypropylmethylcellulose. The total weight percent of all components comprising the wall is equal to 100 wt %. The internal compartment comprises the compound-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form can be made to deliver prodrug from the dosage form to the patient at a zero order rate of release over a period of up to about 24 hours.

The expression "passageway" as used herein comprises means and methods suitable for the metered release of the compound from the compartment of the dosage form. The exit means comprises at least one passageway, including orifice, bore, aperture, pore, porous element, hollow fiber, capillary tube, channel, porous overlay, or porous element that provides for the osmotic controlled release of compound. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leachable polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Regardless of the specific form of sustained release oral dosage form used, compounds are preferably released from the dosage form over a period of at least about 6 hours, more preferably, over a period of at least about 8 hours, and most preferably, over a period of at least about 12 hours. Further, the dosage form preferably releases from 0 to 30% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours. The sustained release oral dosage form further provides a concentration of baclofen or baclofen analog in the blood plasma of the patient over time, which curve has an area under the curve (AUC) that is proportional to the dose of the prodrug of baclofen or baclofen analog administered, and a maximum concentration $C_{max}$. The $C_{max}$ is less than 75%, and is preferably, less than 60%, of the $C_{max}$ obtained from administering an equivalent dose of the compound from an immediate release oral dosage form and the AUC is substantially the same as the AUC obtained from administering an equivalent dose of the prodrug from an immediate release oral dosage form.

Preferred dosage forms are administered once or twice per day, more preferably, once per day.

4.6 Therapeutic Uses of Compounds, Compositions and Dosage Forms

In some embodiments, a therapeutically effective amount of one or more compounds of Formulae (I), (V) or (VI) is administered to a patient, preferably a human, suffering from stiffness, involuntary movements and/or pain associated with spasticity. The underlying etiology of the spasticity being so treated may have a multiplicity of origins, including, e.g., cerebral palsy, multiple sclerosis, stroke and head and spinal cord injuries. In other embodiments, a therapeutically effective amount of one or more compounds of Formulae (I), (V) or (VI) is administered to a patient, preferably a human, suffering from gastro-esophageal reflux disease. In still other embodiments, a therapeutically effective amount of one or more compounds of Formulae (I), (V) or (VI) is administered to a patient, preferably a human, suffering from emesis. In still other embodiments, a therapeutically effective amount of one or more compounds of Formulae (I), (V) or (VI) is administered to a patient, preferably, a human, suffering from cough. In still other embodiments, a therapeutically effective amount of one or more compounds of Formulae (I), (V) or (VI) is administered to a patient, preferably a human, suffering from drug addiction. Addiction to stimulants such as cocaine or amphetamines, or narcotics such as morphine or heroin may be effectively treated by administration of one or more compounds of Formulae (I), (V) or (VI). In yet other embodiments, a therapeutically effective amount of one or more compounds of Formulae (I), (V) or (VI) is administered to a patient, preferably a human, suffering from alcohol abuse or addiction and nicotine abuse or addiction. In some of the above embodiments, sustained release oral dosage forms are administered to the patients.

Further, in certain embodiments, a therapeutically effective amount of one or more compounds of Formulae (I), (V) or (VI) are administered to a patient, preferably a human, as a preventative measure against various diseases or disorders. Thus, the therapeutically effective amount of one or more compounds of Formulae (I), (V) or (VI) may be administered as a preventative measure to a patient having a predisposition for spasticity, gastro-esophageal reflux disease, emesis, cough, alcohol addiction or abuse, nicotine abuse or addiction or other drug addiction or abuse.

When used to treat or prevent the above diseases or disorders the therapeutically effective amount of one or more compounds of Formulae (I), (V) or (VI) may be administered or applied singly, or in combination with other agents. The therapeutically effective amount of one or more compounds of Formulae (I), (V) or (VI) may also deliver a compound disclosed herein in combination with another pharmaceutically active agent, including another compound disclosed herein. For example, in the treatment of a patient suffering from gastro-esophageal reflux disease, a dosage form comprising a compound of Formulae (I), (V) or (VI) may be administered in conjunction with a proton pump inhibitor, such as omeprazole, esomeprazole, pantoprazole, lansoprazole or rabeprazole sodium, or with an $H_2$ antagonist such as rantidine, cimetidine or famotidine.

Dosage forms, upon releasing the baclofen or baclofen analog prodrug, preferably provide baclofen or baclofen analogs upon in vivo administration to a patient. While not wishing to bound by theory, the promoiety or promoieties of the prodrug may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the prodrug. If the promoiety or promoieties are cleaved after absorption by the gastrointestinal tract, these baclofen or baclofen analog prodrugs may have the opportunity to be absorbed into the systemic circulation from the large intestine. It is preferred that the promoiety or promoieties are cleaved after absorption by the gastrointestinal tract.

4.7 Doses

Baclofen and baclofen analog prodrugs are administered to treat or prevent diseases or disorders such as spasticity, gastro-esophageal reflux disease, emesis, cough, alcohol, nicotine or other drug addiction.

The amount of baclofen or baclofen analog prodrug that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of a compound administered will, of course, be dependent on, among other factors, the subject being treated, the weight of the subject, the severity of the affliction, the manner of administration and the judgment of the prescribing physician.

Preferably, the dosage forms are adapted to be administered to a patient no more than twice per day, more preferably, only once per day. Dosing may be provided alone or in combination with other drugs and may continue as long as required for effective treatment of the disease state or disorder.

Suitable dosage ranges for oral administration are dependent on the potency of the parent baclofen analog. For baclofen doses are generally between about 0.15 mg to about 2.5 mg per kilogram body weight. Other baclofen analogs may be more potent and lower doses may be appropriate for both the parent drug and any prodrug (measured on an equivalent molar basis). For example, doses of R-baclofen prodrugs that are equivalent (on a molar basis) to R-baclofen doses of between about 0.03 mg to about 1 mg per kilogram body weight are appropriate. Dosage ranges may be readily determined by methods known to the skilled artisan.

5. EXAMPLES

The following examples describe in detail preparation of compounds and compositions disclosed herein and assays for using compounds and compositions disclosed herein. It will be apparent to those of ordinary skill in the art that many modifications, both to materials and methods, may be practiced.

In the examples below, the following abbreviations have the following meanings. If an abbreviation is not defined, it has its generally accepted meaning.

Boc=tert-butyloxycarbonyl
Cbz=carbobenzyloxy
DCC=dicyclohexylcarbodiimide
DMAP=4-N,N-dimethylaminopyridine
DMF=N,N-dimethylformamide
DMSO=dimethylsulfoxide
Fmoc=9-fluorenylmethyloxycarbonyl
g=gram
h=hour
HPLC=high pressure liquid chromatography
L=liter
LC/MS=liquid chromatography/mass spectroscopy
M=molar
min=minute
mL=milliliter
mmol=millimoles
THF=tetrahydrofuran
TFA=trifluoroacetic acid
TLC=thin layer chromatography
TMS=trimethylsilyl
μL=microliter
μM=micromolar
v/v=volume to volume

Example 1

4-tert-Butoxycarbonylamino-(3R)-(4-chlorophenyl)-butanoic Acid (5)

To a stirred solution containing (R)-baclofen hydrochloride (2.34 g, 9.36 mmol) and NaOH (0.97 g, 24.34 mmol) in a mixture of dioxane and water (1:1) was added a solution of di-tert-butyl dicarbonate (2.65 g, 12.16 mmol) in dioxane (10 mL). The resulting solution was stirred at ambient temperature for 40 min. Then the reaction mixture was concentrated on a rotary evaporator to remove most of dioxane, the residue was extracted with ether to remove excess di-tert-butyl dicarbonate and the aqueous phase was acidified to pH ~3 with saturated citric acid solution to precipitate a white solid. The precipitate was filtered, washed with water, dried in a desiccator in vacuo to afford the title compound (5) as a white fluffy powder (2.4 g, 82%). $^1$H NMR (CDCl$_3$, 400 MHz): δ 1.40 (s, 9H), 2.56 (dd, 1H), 2.68 (dd, 1H), 3.26 (m, 2H), 3.40 (m, 1H), 7.14 (d, 2H), 7.27 (d, 2H).

Example 2

Benzyl 4-tert-Butoxycarbonylamino-(3R)-(4-chlorophenyl)-butanoate (6)

To a stirred solution of compound (5) (1.41 g, 4.49 mmol) and benzyl bromide (0.769 g, 4.49 mmol) in DMF was added Cs$_2$CO$_3$ (1.46 g, 4.49 mmol) at ambient temperature. The resulting suspension was stirred for 3 h, with the reaction progress monitored by TLC and/or LC/MS. The reaction mixture was poured into ice-water, extracted with ethyl acetate and the combined organic phase was washed with water and brine, dried over anhydrous Na$_2$SO$_4$ and concentrated in vacuo to afford the title compound (6) as a white solid (1.69 g, 94%). $^1$H NMR (CDCl$_3$, 400 MHz): δ 1.39 (s, 9H), 2.61 (dd, 1H), 2.74 (dd, 1H), 3.30 (m, 2H), 3.40 (m, 1H), 4.46 (br s, 1H), 4.99 (s, 2H), 7.07-7.35 (m, 9H).

Example 3

Benzyl 4-Amino-(3R)-(4-chlorophenyl)-butanoate Hydrochloride (7)

Compound (6) (1.69 g, 4.19 mmol) was dissolved in a 4N solution of HCl in dioxane and the resulting reaction mixture stirred at room temperature for 40 min. The reaction mixture was diluted with ether, the resulting precipitate was filtered off, washed with ether and hexane, and dried in vacuo to afford the title compound (7) (1.39 g, 98%). $^1$H NMR (CD$_3$OD, 400 MHz): δ 2.72 (dd, 1H), 2.86 (dd, 1H), 3.12 (m, 1H), 3.27 (m, 1H), 3.47 (m, 1H), 5.01 (s, 2H), 7.06-7.30 (m, 9H). MS (ESI) m/z 304.19 (M+H)$^+$.

Example 4

Benzyl 4-(Chloromethoxy)carbonylamino-(3R)-(4-chlorophenyl)-butanoate (8)

To a stirred suspension of compound (7) (500 mg, 1.47 mmol) in CH$_2$Cl$_2$ (20 mL) at 0° C. was added N-methylmorpholine (0.404 mL, 3.67 mmol). The resulting mixture was stirred at 0° C. until a clear solution was obtained. Then 1-chloromethyl chloroformate (199 mg, 1.544 mmol) in CH$_2$Cl$_2$ (1 mL) was added and the reaction mixture was stirred at 0° C. with TLC monitoring. After 40 minutes, the reaction was diluted with CH$_2$Cl$_2$, washed with citric acid solution and brine and dried over anhydrous Na$_2$SO$_4$. The solvent was removed in vacuo to afford the title compound (8) (430 mg, 74%). $^1$H NMR (CDCl$_3$, 400 MHz): δ 2.64 (dd, 1H), 2.74 (dd, 1H), 3.49 (m, 2H), 3.53 (m, 1H), 4.92 (br, s, 1H), 5.01 (s, 2H), 5.66 (AB q, 2H), 7.07-7.30 (m, 9H).

Example 5

Benzyl 4-[(Acetoxymethoxy)carbonylamino]-(3R)-(4-chlorophenyl)-butanoate (9)

To a suspension of Ag$_2$CO$_3$ (417 mg, 1.514 mmol) and acetic acid (0.170 mL, 3.028 mmol) in CHCl$_3$ (2 mL) was added a solution of compound (8) (300 mg, 0.757 mmol) in CHCl$_3$ (1 mL). The resulting suspension was stirred at room temperature for 24 h. The reaction mixture was then diluted with CH$_2$Cl$_2$, filtered through a pad of Celite, and the filtrate washed with 10% aqueous NaHCO$_3$ solution and brine, then dried over anhydrous Na$_2$SO$_4$. After removal of the solvent in vacuo, the residue was purified by flash chromatography on silica gel, eluting with a gradient of 15%-30% ethyl acetate in hexane to afford the title compound (9) (280 mg, 88%). $^1$H NMR (CDCl$_3$, 400 MHz): δ 2.05 (s, 3H), 2.62 (m, 1H), 2.70 (m, 1H), 3.33 (m, 2H), 3.47 (m, 1H), 4.99 (m, 3H), 5.62 (s, 2H), 7.08-7.28 (m, 9H).

Example 6

Sodium 4-[(Acetoxymethoxy)carbonylamino]-(3R)-(4-chlorophenyl)-butanoate (10)

A solution of compound (9) (80 mg, 0.190 mmol) in ethanol (20 mL) was stirred with 10% Pd on carbon (8 mg) in a 50 mL round-bottomed flask under an atmosphere of hydrogen gas (balloon). The reaction was judged complete in 30 min. (monitoring by LC/MS). The mixture was filtered through a pad of Celite, and the solvent removed in vacuo to afford the crude product, which was purified by preparatory LC/MS to give the product in its protonated acid form (46 mg, 73%). $^1$H NMR (CD$_3$OD, 400 MHz): δ 2.04 (s, 3H), 2.57 (m, 1H), 2.72 (m, 1H), 3.31 (m, 3H), 5.61 (s, 2H), 7.22-7.28 (m, 4H). MS (ESI) m/z 328.13 (M−H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (10).

Example 7

Benzyl 4-[(Benzoyloxymethoxy)carbonylamino]-(3R)-(4-chlorophenyl)-butanoate (11)

Following the procedure of Example 5 and replacing acetic acid with benzoic acid, compound (11) was obtained in 72% yield. $^1$H NMR (CDCl$_3$, 400 MHz): δ 2.62 (dd, 1H), 2.72 (dd, 1H), 3.33 (m, 2H), 3.50 (m, 1H), 4.98 (br. s, 3H), 5.90 (s, 2H), 7.05 (d, 2H), 7.12-7.28 (m, 7H), 7.56 (t, 1H), 7.41 (t, 2H), 8.03 (d, 2H).

Example 8

Sodium 4-[(Benzoyloxymethoxy)carbonylamino]-(3R)-(4-chlorophenyl)-butanoate (12)

Following the procedure of Example 6 and replacing compound (9) with compound (11) afforded the product in its protonated acid form in 69% yield. $^1$H NMR (CD$_3$OD, 400 MHz): δ 2.57 (m, 1H), 2.71 (m, 1H), 3.33 (m, 3H), 5.89 (AB q, 2H), 7.20 (m, 4H), 7.50 (t, 2H), 7.63 (t, 1H), 8.00 (d, 2H). MS (ESI) m/z 390.15 (M−H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (12).

Example 9

Benzyl 4-[(Cyclohexanecarboxymethoxy)carbonylamino]-(3R)-(4-chlorophenyl)-butanoate (13)

Following the procedure of Example 5 and replacing acetic acid with cyclohexane carboxylic acid, compound (13) was obtained in 38% yield. $^1$H NMR (CDCl$_3$, 400 MHz): δ 1.20-1.42 (m, 5H), 1.62-1.87 (m, 5H), 2.29 (m, 1H), 2.61 (m, 1H), 2.71 (m, 1H), 3.32 (m, 2H), 3.48 (m, 1H), 4.99 (s, 2H), 5.12 (br. s, 1H), 5.64 (m, 2H), 7.06-7.28 (m, 9H).

Example 10

Sodium 4-[(Cyclohexanecarboxymethoxy)carbonylamino]-(3R)-(4-chlorophenyl)-butanoate (14)

Following the procedure of Example 6 and replacing compound (9) with compound (13) afforded the product in its protonated acid forms in 40% yield. $^1$H NMR (CDCl$_3$, 400 MHz): δ 1.20-1.40 (m, 5H), 1.63-1.93 (m, 5H), 2.35 (m, 1H), 2.70 (m, 2H), 3.36 (m, 2H), 3.54 (m, 1H), 5.02 (br. m, 1H), 5.69 (m, 2H), 7.15 (d, 2H), 7.28 (d, 2H). MS (ESI) m/z 396.18 (M−H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (14).

Example 11

Benzyl 4-[(Butanoyloxymethoxy)carbonylamino]-(3R)-(4-chlorophenyl)-butanoate (15)

Following the procedure of Example 5 and replacing acetic acid with n-butyric acid, compound (15) was obtained. $^1$H NMR (CDCl$_3$, 400 MHz): δ 0.93 (t, 3H), 1.63 (m, 2H), 2.30 (t, 2H), 2.64 (m, 1H), 2.74 (m, 1H), 3.33 (m, 2H), 3.49 (m, 1H), 4.91 (br. s, 1H), 5.00 (s, 2H), 5.65 (m, 2H), 7.06-7.30 (m, 9H).

Example 12

Sodium 4-[(Butanoyloxymethoxy)carbonylamino]-(3R)-(4-chlorophenyl)-butanoate (16)

Following the procedure of Example 6 and replacing compound (9) with compound (15) afforded the product in its protonated acid form in 40% yield. $^1$H NMR (CDCl$_3$, 400 MHz): δ 0.94 (t, 3H), 1.64 (m, 2H), 2.32 (t, 2H), 2.65 (m, 2H), 3.35 (m, 2H), 3.52 (m, 1H), 5.00 (br. s, 1H), 5.67 (s, 21), 7.11-7.29 (m, 4H). MS (ESI) m/z 356.19 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (16).

Example 13

Benzyl 4-[(Isobutanoyloxymethoxy)carbonylamino]-(3R)-(4-chlorophenyl)-butanoate (17)

Following the procedure of Example 5 and replacing acetic acid with isobutyric acid, compound (17) was obtained in 22% yield. $^1$H NMR (CDCl$_3$, 400 MHz): δ 1.15 (m, 6H), 2.55 (m, 1H), 2.62 (dd, 1H), 2.72 (dd, J=1H), 3.33 (n, 2H), 3.48 (m, 1H), 4.83 (br. s, 1H), 4.99 (s, 2H), 5.65 (s, 2H), 7.06-7.30 (m, 9H).

Example 14

Sodium 4-[(Isobutanoyloxymethoxy)carbonylamino]-(3R)-(4-chlorophenyl)-butanoate (18)

Following the procedure of Example 6 and replacing compound (9) with compound (17) afforded the product in its protonated acid form in 80% yield. $^1$H NMR (CDCl$_3$, 400 MHz): δ 1.16 (m, 6H), 2.60 (m, 1H), 2.71 (m, 1H), 3.35 (m, 2H), 3.51 (m, 1H), 5.03 (br. t, 1H), 5.67 (s, 2H), 7.12 (d, 2H), 7.26 (d, 2H). MS (ESI) m/z 356.15 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (18).

Example 15

Benzyl 4-[(Pivaloyloxymethoxy)carbonylamino]-(3R)-(4-chlorophenyl)-butanoate (19)

Following the procedure of Example 5 and replacing acetic acid with pivalic acid, compound (19) was obtained in 36% yield. $^1$H NMR (CDCl$_3$, 400 MHz): δ 1.17 (s, 9H), 2.62 (dd, 1H), 2.72 (dd, 1H), 3.33 (m, 2H), 3.48 (m, 1H), 4.84 (br. t, 1H), 5.00 (s, 2H), 5.65 (s, 2H), 7.06-7.30 (m, 9H).

Example 16

Sodium 4-[(Pivaloyloxymethoxy)carbonylamino]-(3R)-(4-chlorophenyl)-butanoate (20)

Following the procedure of Example 6 and replacing compound (9) with compound (19) afforded the product in its protonated acid form in 75% yield. $^1$H NMR (CDCl$_3$, 400 MHz): δ 1.19 (s, 9H), 2.60 (dd, 1H), 2.68 (dd, 1H), 3.34 (m, 2H), 3.51 (m, 1H), 5.01 (br. t, 1H), 5.66 (s, 2H), 7.11 (m, 2H), 7.26 (m, 2H). MS (ESI) m/z 370.22 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (20).

Example 17

Benzyl 4-[(1-Chloroisobutoxy)carbonylamino]-(3R)-(4-chlorophenyl)-butanoate (21)

To a stirred suspension of compound (7) (900 mg, 2.64 mmol) in CH$_2$Cl$_2$ (50 mL) at 0° C. was added N-methylmorpholine (0.97 mL, 8.82 mmol). The resulting mixture was stirred at 0° C. until a clear solution was obtained. Then 1-chloro-2-methylpropyl chloroformate (474 mg, 2.77 mmol) in CH$_2$Cl$_2$ (1 mL) was added and the solution stirred at 0° C. for 3 h (TLC monitoring). The reaction mixture was diluted with CH$_2$Cl$_2$, washed with citric acid solution and brine, then dried over anhydrous Na$_2$SO$_4$. Removal of the solvent in vacuo afforded the title compound (21) as a pair of diastereomers (932 mg, 80%). $^1$H NMR (CDCl$_3$, 400 MHz): δ 0399 (d, 3H), 1.02 (d, 3H), 2.10 (m, 1H), 2.64 (dd, 1H), 2.74 (dd, 1H), 3.33 (m, 2H), 3.53 (m, 1H), 4.80 (br. s, 1H), 5.01 (s, 2H), 6.24 (d, 1H), 7.07-7.30 (m, 9H).

Example 18

Benzyl 4-[(1-Acetoxyisobutoxy)carbonylamino]-(3R)-(4-chlorophenyl)-butanoate (22)

To a solution of compound (21) (246 mg, 0.561 mmol) in CH$_2$Cl$_2$ (0.5 mL) was added acetic acid (0.32 mL, 5.61 mmol) and N-methylmorpholine (0.31 mL, 2.8 mmol). The resulting mixture was stirred for 48 h at room temperature. The reaction then was diluted with CH$_2$Cl$_2$, washed successively with water, 10% aqueous NaHCO$_3$ solution, dilute citric acid solution and brine, then dried over anhydrous Na$_2$SO$_4$. After removal of the solvent in vacuo, the residue was purified by flash chromatography on silica gel, eluting with a gradient of 10%-20% ethyl acetate in hexane to afford the title compound (22) as a pair of diastereomers (120 mg, 46%). $^1$H NMR (CDCl$_3$, 400 MHz): δ 0.92 (m, 6H), 2.10 (m, 4H), 2.75 (m, 2H), 3.45 (m, 3H), 4.68 (br. s, 1H), 5.00 (s, 2H), 6.44 (m, 1H), 7.02-7.33 (m, 9H).

Example 19

Sodium 4-[(1-Acetoxyisobutoxy)carbonylamino]-(3R)-(4-chlorophenyl)-butanoate (23)

Following the procedure of Example 6 and replacing compound (9) with compound (22), the product in protonated acid form was obtained as a pair of diastereomers. $^1$H NMR (CDCl$_3$, 400 MHz): δ 0.92 (m, 6H), 1.93 (m, 1H), 2.05 (s, 3H), 2.65 (m, 2H), 3.33 (m, 2H), 3.49 (m, 1H), 4.70 (br. s., 1H), 6.50 (m, 1H), 7.10 (m, 2H), 7.26 (m, 2H). MS (ESI) m/z 370.20 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (23).

Example 20

Benzyl 4-[(1-Isobutanoyloxyisobutoxy)carbonylamino]-(3R)-(4-chlorophenyl)-butanoate (24)

To a solution of compound (21) (50 mg, 0.114 mmol) in isobutyric acid (0.5 mL, 5.39 mmol) was added N-methylmorpholine (0.57 mmol). After stirring the mixture overnight at 50° C., the reaction mixture was diluted with CH$_2$Cl$_2$, washed successively with water, 10% aqueous NaHCO$_3$ solution and brine and then dried over anhydrous Na$_2$SO$_4$. After removal of the solvent in vacuo, the title compound (24) was obtained as a pair of diastereomers (40 mg, 72%). $^1$H NMR (CDCl$_3$, 400 MHz): δ 0.91 (m, 6H), 1.17 (m, 6H), 1.96 (m, 1H), 2.54 (m, 1H), 2.63 (m, 1H), 2.73 (m, 1H), 3.31 (m, 2H), 3.48 (m, 1H), 4.68 (br. s, 1H), 6.52 (m, 1H), 7.07-7.29 (m, 9H).

Example 21

Sodium 4-[(1-Isobutanoyloxyisobutoxy)carbonylamino]-(3R)-(4-chlorophenyl)-butanoate (25)

Following the procedure of Example 6 and replacing compound (9) with compound (24), the product in protonated acid form was obtained as a pair of diastereomers in 50% yield. $^1$H NMR (CDCl$_3$, 400 MHz): δ 0.92 (m, 6H), 1.16 (m, 6H), 1.97 (m, 1H), 2.51-2.74 (m, 3H), 3.33 (m, 3H), 6.50 (d, 1H), 7.10 (d, 2H), 7.27 (d, 2H). MS (ESI) m/z 398.18 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (25).

Example 22

Benzyl 4-[(1-Butanoyloxyisobutoxy)carbonylamino]-(3R)-(4-chlorophenyl)-butanoate (26)

Following the procedure of Example 20 and replacing isobutyric acid with n-butyric acid, the title compound (26) was obtained as a pair of diastereomers (90 mg, 80%). $^1$H NMR (CDCl$_3$, 400 MHz): δ 0.92 (m, 9H), 1.64 (m, 2H), 1.96 (m, 1H), 2.27 (m, 2H), 2.61 (m, 1H), 2.74 (m, 1H), 3.32 (m, 2H), 3.48 (m, 1H), 4.76 (br. s, 1H), 6.53 (m, 1H), 7.06-7.28 (m, 9H).

Example 23

Sodium 4-[(1-Butanoyloxyisobutoxy)carbonylamino]-(3R)-(4-chlorophenyl)-butanoate (27)

Following the procedure of Example 6 and replacing compound (9) with compound (26), the product in protonated acid form was obtained as a pair of diastereomers in 75% yield. $^1$H NMR (CDCl$_3$, 400 MHz): δ 0.92 (m, 9H), 1.65 (m, 2H), 1.96 (m, 1H), 2.29 (t, 2H), 2.66 (m, 2H), 3.25-3.59 (m, 3H), 4.72 (br. d, 1H), 6.52 (d, 1H), 7.11 (d, 2H), 7.26 (d, 2H). MS (ESI) m/z 398.24 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (27).

Example 24

Benzyl 4-[(1-Chloroethoxy)carbonylamino]-(3R)-(4-chlorophenyl)-butanoate (28)

Following the procedure of Example 17 and replacing 1-chloro-2-methylpropyl chloroformate with 1-chloroethyl chloroformate, the title compound (28) was obtained as a pair of diastereomers in 67% yield. $^1$H NMR (CDCl$_3$, 400 MHz): δ 1.71 (d, 3H), 2.63 (dd, 1H), 2.73 (dd, 1H), 3.32 (m, 2H), 3.49 (m, 1H), 5.00 (m, 3H), 6.48 (q, 1H), 7.07 (d, 2H), 7.14-7.28 (m, 7H).

Example 25

Benzyl 4-[(1-Acetoxyethoxy)carbonylamino]-(3R)-(4-chlorophenyl)-butanoate (29)

To a stirred solution of compound (28) (183 mg, 0.446 mmol) in CH$_2$Cl$_2$ (5 mL) was added acetic acid (0.26 mL, 4.46 mmol) and N-methylmorpholine (0.25 mL, 2.23 mmol), and the resulting reaction mixture was stirred at room temperature for 48 h. The mixture was diluted with CH$_2$Cl$_2$, washed successively with water, 10% aqueous NaHCO$_3$ solution and brine, then dried over anhydrous Na$_2$SO$_4$. After removal of the solvent in vacuo, the residue was purified by flash chromatography on silica gel, eluting with a gradient of 10%-20% ethyl acetate in hexane to afford the title compound (29) as a pair of diastereomers (110 mg, 57%). $^1$H NMR (CDCl$_3$, 400 MHz): δ 1.41 (m, 3H), 2.03° (m, 3H), 2.61 (m, 1H), 2.72 (m, 1H), 3.33 (m, 2H), 3.49 (m, 1H), 4.82 (br. s, 1H), 5.00 (s, 2H), 6.74 (m, 1H), 7.13 (m, 2H), 7.17-7.28 (m, 7H).

Example 26

Sodium 4-[(1-Acetoxyethoxy)carbonylamino]-(3R)-(4-chlorophenyl)-butanoate (30)

Following the procedure of Example 6 and replacing compound (9) with compound (29), the product in its protonated acid form was obtained as a pair of diastereomers in 57% yield. $^1$H NMR (CDCl$_3$, 400 MHz): δ 1.42 (m, 3H), 2.02 (m, 3H), 2.62 (m, 1H), 2.71 (m, 1H), 3.32 (m, 2H), 3.49 (m, 1H), 4.80 (br. s, 1H), 6.74 (m, 1H), 7.13 (m, 2H), 7.27 (m, 2H). MS (ESI) m/z 342.24 (M–H)$^-$.

The carboxylic acid was converted to the sodium salt by dissolution in MeCN (0.5 mL) and then addition of aqueous NaHCO$_3$ (1 equiv.) with sonication for 10 min. The solvent was removed by lyophilization to afford the title compound (30).

Example 27

Benzyl 4-[(1-Butanoyloxyethoxy)carbonylamino]-(3R)-(4-chlorophenyl)-butanoate (31)

Following the procedure of Example 25 and replacing acetic acid with n-butyric acid, the title compound (31) was obtained as a pair of diastereomers (109 mg, 68%). $^1$H NMR (CDCl$_3$, 400 MHz): δ 0.94 (m, 3H), 1.42 (m, 3H), 1.64 (m, 2H), 2.27 (m, 2H), 2.60 (m, 1H), 2.71 (m, 1H), 3.31 (m, 2H), 3.50 (m, 1H), 4.80 (br. s, 1H), 5.00 (s, 2H), 6.75 (m, 1H), 7.11 (d, 2H), 7.15-7.28 (m, 7H).

Example 28

Sodium 4-[(1-Butanoyloxyethoxy)carbonylamino]-(3R)-(4-chlorophenyl)-butanoate (32)

Following the procedure of Example 6 and replacing compound (9) with compound (31), the product in its protonated acid form was obtained as a pair of diastereomers in 75% yield. $^1$H NMR (CDCl$_3$, 400 MHz): δ 0.94 (m, 3H), 1.42 (m, 3H), 1.64 (m, 2H), 2.27 (m, 2H), 2.60 (m, 1H), 2.71

(m, 1H), 3.31 (m, 2H), 3.50 (m, 1H), 4.82 (br. s, 1H), 6.75 (m, 1H), 7.11 (d, 2H), 7.27 (d, 2H). MS (ESI) m/z 370.27 (M−H)⁻.

The carboxylic acid was converted to the sodium salt by dissolution in MeCN (0.5 mL) and then addition of aqueous NaHCO₃ (1 equiv.) with sonication for 10 min. The solvent was removed by lyophilization to afford the title compound (32).

Example 29

Sodium 4-[(1-Isobutanoyloxyethoxy)carbonylamino]-(3R)-(4-chlorophenyl)-butanoate (33)

To a suspension of R-baclofen hydrochloride (500 mg, 1.47 mmol) in CH₂Cl₂ at 0° C. was added triethylamine (0.9 mL, 6.4 mmol) and a 1N solution of chlorotrimethylsilane in CH₂Cl₂ (3.23 mL, 3.23 mmol). The resulting reaction mixture was stirred at 0° C. for 10 min, then was added 1-isobutanoyloxyethyl-p-nitrophenyl carbonate (577 mg, 1.94 mmol, prepared as described in Gallop et al., U.S. Patent Appl. Publ. 2003/0176398, in CH₂Cl₂. The reaction mixture was stirred at room temperature for 3 h (monitoring by LC/MS) and then diluted with CH₂Cl₂, washed with citric acid solution and brine, and dried over anhydrous Na₂SO₄. After removal of solvent in vacuo, the residue was purified by flash chromatography on silica gel, eluting first with CH₂Cl₂ to remove p-nitrophenol, then with 20% ethyl acetate in hexane to afford the product in its protonated acid form as a pair of diastereomers (400 mg, 73%). ¹H NMR (CDCl₃, 400 MHz): δ 1.13 (m, 6H), 1.40 (m, 3H), 2.51 (m, 1H), 2.57 (dd, 1H), 2.71 (dd, 1H), 3.32 (m, 2H), 3.47 (m, 1H), 4.89 (br. s, 1H), 6.72 (q, 1H), 7.11 (d, 2H), 7.26 (d, 2H). MS (ESI) m/z 370.15 (M−H)⁻.

The carboxylic acid was converted to the sodium salt by dissolution in MeCN (0.5 mL) and then addition of aqueous NaHCO₃ (1 equiv.) with sonication for 10 min. The solvent was removed by lyophilization to afford the title compound (33).

Example 30

Asymmetric Synthesis of Sodium 4-{[(1S)-Isobutanoyloxyethoxy]-carbonylamino}-(3R)-(4-chlorophenyl) -butanoate (34)

Step A: Synthesis of 4-{[(1S)-Isobutanoylethoxy]carbonylamino}-(3R)-(4-chlorophenyl)-butanoic Acid (35)

To a solution of (4S)-hydroxy-2-methylpentan-3-one (200 mg, 1.67 mmol) in CH₂Cl₂ (10 mL) at 0° C. was added p-nitrophenyl chloroformate (336 mg 1.67 mmol), pyridine (0.135 mL, 1.67 mmol) and 4-dimethylaminopyridine (61 mg, 0.5 mmol). The resulting mixture was stirred at 0° C. for 1 h, then allowed to warm to room temperature overnight. The reaction mixture was then added to a suspension containing R-baclofen hydrochloride (500 mg, 1.47 mmol), chlorotrimethylsilane (2.94 mmol) and triethylamine (5.99 mmol) in CH₂Cl₂ at 0° C. The reaction was stirred at room temperature for 5 h, then diluted with CH₂Cl₂, washed successively with water, 10% aqueous NaHCO₃ solution, dilute citric acid solution and brine, then dried over anhydrous Na₂SO₄. After filtration and removal of the solvent in vacuo, the crude product was purified by preparatory LC/MS to afford compound (35) (230 mg, 44%). ¹H NMR (CDCl₃, 400 MHz): δ 1.06 (d, 3H), 1.12 (d, 3H), 1.32 (d, 3H), 2.60 (m, 1H), 2.75 (m, 2H), 3.29 (m, 2H), 3.44 (m, 1H), 5.13 (q, 1H), 7.13 (m, 2H), 7.26 (m, 2H). MS (ESI) m/z 354.10 (M−H)⁻.

Step B: Synthesis of Sodium 4-{[(1S)-Isobutanoyloxyethoxy]carbonylamino}-(3R)-(4-chlorophenyl)-butanoate (34)

To a solution of compound (35) (179 mg, 0.503 mmol) in CH₂Cl₂ (5 mL) at 0° C. was added NaHCO₃ (42 mg, 0.503 mmol) and m-chloroperbenzoic acid (174 mg, 1.00 mmol). The resulting suspension was stirred at 0° C. to room temperature for 24 h, then an additional aliquot of m-chloroperbenzoic acid (174 mg, 1.00 mmol) was added to the reaction. The mixture was allowed to stir at room temperature for a further 24 h, then diluted with CH₂Cl₂, filtered through a pad of Celite, and the filtrate washed with water and brine, then dried over anhydrous Na₂SO₄. After filtration and removal of the solvent in vacuo, the crude product was purified by preparatory LC/MS to afford the product in its protonated acid form as a single diastereomer (24 mg, 14%). ¹H NMR (CDCl₃, 400 MHz): δ 1.15 (d, 6H), 1.40 (d, 3H), 2.51 (hept, 1H), 2.59 (dd, 1H), 2.70 (dd, 1H), 3.30 (m, 2H), 3.50 (m, 1H), 4.94 (br. s, 1H), 6.72 (q, 1H), 7.12 (d, 2H), 7.26 (d, 2H). MS (ESI) m/z 370.15 (M−H)⁻.

The carboxylic acid was converted to the sodium salt by dissolution in MeCN (0.5 mL) and then addition of aqueous NaHCO₃ (1 equiv.) with sonication for 10 min. The solvent was removed by lyophilization to afford the title compound (34).

Example 31

Benzyl 4-[(1-Pivaloylethoxy)carbonylamino]-(3R)-(4-chlorophenyl)-butanoate (35)

To a stirred solution of compound (28) (500 mg, 1.22 mmol) in THF (5 mL) was added pivalic acid (1.24 g, 12.1 mmol) and N-methylmorpholine (0.7 mL, 6.05 mmol), and the resulting reaction mixture was stirred at 50° C. for 48 hours. The reaction mixture was diluted with ethyl acetate, washed successively with water, 10% aqueous NaHCO₃ solution and brine, then dried over anhydrous Na₂SO₄. After removal of solvent in vacuo, the residue was purified by flash chromatography on silica gel, eluting with a gradient of 5-10% ethyl acetate in hexane to afford the title compound (35) as a pair of diastereomers (252 mg, 44%). ¹H NMR (CDCl₃, 400 MHz): δ 1.15 (s, 3H), 1.17 (s, 6H), 1.40 (q, 3H), 2.62 (dd, 1H), 2.74 (dd, 1H), 3.25 (m, 2H), 3.46 (m, 1H), 4.82 (br.t, 1H), 4.99 (s, 2H), 6.71 (m, 1H), 7.29-7.07 (m. 9H).

Example 32

Sodium 4-[(1-Pivaloylethoxy)carbonylamino]-(3R)-(4-chlorophenyl)-butanoate (36)

Following the procedure of Example 6 and replacing compound (9) with compound (35), the product in its protonated acid form was obtained as a pair of diastereomers in 76% yield. ¹H NMR (CDCl₃, 400 MHz): δ 1.16 (s, 3H), 1.18 (s, 6H), 1.40 (d, 3H), 2.59 (dd, 1H), 3.31 (m, 2H), 3.48 (m, 1H), 3.70 (dd, 1H), 4.82 (m, 1H), 6.70 (m, 1H), 7.12 (d, 2H), 7.26 (d, 2H). MS (ESI) m/z 384.18 (M−H)⁻.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (36).

Example 33

Benzyl 4-[(1-Cyclohexylcarbonyloxyethoxy)carbonylamino]-(3R)-(4-chlorophenyl)-butanoate (37)

To a stirred solution of compound (28) (500 mg, 1.22 mmol) in THF (5 mL) was added cyclohexanecarboxylic acid (1.56 g, 12.14 mmol) and N-methylmorpholine (0.7 mL, 6.05 mmol), and the resulting reaction mixture was stirred at 45° C. for 48 hours. The reaction mixture was diluted with ethyl acetate, washed successively with water, 10% aqueous NaHCO$_3$ solution and brine, then dried over anhydrous Na$_2$SO$_4$. After removal of solvent in vacuo, the residue was purified by flash chromatography on silica gel, eluting with a gradient of 5-10% ethyl acetate in hexane to afford the title compound (37) as a pair of diastereomers (348 mg, 57%). $^1$H NMR (CDCl$_3$, 400 MHz): δ 1.22 (m, 3H), 1.39 (m, 5H), 1.61 (m, 1H), 1.72 (m, 2H), 1.85 (m, 2H), 2.24 (m, 1H), 2.62 (dd, 1H), 2.73 (dd, 1H), 3.30 (m, 2H), 3.46 (m, 1H), 4.90 (br. m, 1H), 4.98 (s, 2H), 6.73 (m, 1H), 7.07-7.28 (m, 9H).

Example 34

Sodium 4-[(1-Cyclohexylcarbonyloxyethoxy)carbonylamino]-(3R)-(4-chlorophenyl)-butanoate (38)

Following the procedure of Example 6 and replacing compound (9) with compound (37), the product in its protonated acid form was obtained as a pair of diastereomers in 38% yield. $^1$H NMR (CDCl$_3$, 400 MHz): δ 1.24 (m, 3H), 1.40 (m, 5H), 1.63 (m, 1H), 1.74 (m, 2H), 1.86 (m, 2H), 2.27 (m, 1H), 2.59 (dd, 1H), 2.70 (dd, 1H), 3.31 (m, 2H), 3.48 (m, 1H), 4.79 (br. d, 1H), 6.72 (q, 1H), 7.11 (d, 2H), 7.25 (d, 2H). MS (ESI) m/z 410.21 (M-H)$^-$.

The carboxylic acid was converted to the sodium salt by dissolution in MeCN (0.5 mL) and then addition of aqueous NaHCO3 (1 eq.) with sonication for 10 min. The solvent was removed by lyophilization to afford the title compound (38).

Example 35

Benzyl 4-[(1-Benzoyloxyethoxy)carbonylamino]-(3R)-(4-chlorophenyl)-butanoate (39)

Following the synthesis procedure for compound (37) and replacing cyclohexanecarboxylic acid with benzoic acid, the title compound (39) was obtained as a pair of diastereomers in 69% yield. $^1$H NMR (CDCl$_3$, 400 MHz): δ 1.54 (q, 3H), 2.62 (m, 1H), 2.74 (dd, 1H), 3.31 (m, 2H), 3.48 (m, 1H), 4.92 (br. s, 1H), 4.97 (s, 2H), 7.01 (q, 1H), 7.27-7.05 (m, 10H), 7.39 (m, 2H), 7.52 (m, 1H), 7.98 (m, 2H).

Example 36

Sodium 4-[(1-Benzoyloxyethoxy)carbonylamino]-(3R)-(4-chlorophenyl)-butanoate (40)

Following the procedure of Example 6 and replacing compound (9) with compound (39), the product in its protonated acid form was obtained as a pair of diastereomers in 74% yield. $^1$H NMR (CDCl$_3$, 400 MHz): δ 1.56 (t, 3H), 2.59 (m, 1H), 2.71 (m, 1H), 3.33 (m, 2H), 3.49 (m, 1H), 7.01 (q, 1H), 7.10 (d, 2H), 7.25 (dd, 2H), 7.42 (t, 2H), 7.55 (t, 1H), 8.02 (t, 2H). MS (ESI) m/z 404.17 (M-H)$^-$.

The carboxylic acid was converted to the sodium salt by dissolution in MeCN (0.5 mL) and then addition of aqueous NaHCO3 (1 eq.) with sonication for 10 min. The solvent was removed by lyophilization to afford the title compound (40).

Example 37

Benzyl 4-[(1-Benzoyloxyisobutoxy)carbonylamino]-(3R)-(4-chlorophenyl)-butanoate (41)

To a stirred solution of compound (21) (0.634 g, 1.45 mmol) in THF (5 mL) was added benzoic acid (1.76 g, 14.5 mmol) and N-methylmorpholine (0.73 g, 7.23 mmol), and the resulting reaction mixture was stirred at 50° C. for 48 hours. The reaction mixture was diluted with ethyl acetate, washed successively with water, 10% aqueous NaHCO$_3$ solution and brine, then dried over anhydrous Na$_2$SO$_4$. After removal of solvent in vacuo, the residue was purified by flash chromatography on silica gel, eluting with a gradient of 5%-10 ethyl acetate in hexane to afford the title compound (41) as a pair of diastereomers (0.59 g, 45%). $^1$H NMR (CDCl$_3$, 400 MHz): δ 1.02 (m, 6H), 2.10 (m, 1H), 2.63 (m, 1H), 2.74 (m, 1H), 3.32 (m, 2H), 3.49 (m, 1H), 4.79 (t, 1H), 4.98 (d, 2H), 6.78 (t, 1H), 7.07 (d, 2H), 7.18 (m, 4H), 7.27 (m, 3H), 7.40 (m, 2H), 7.56 (m, 1H), 8.01 (t, 2H).

Example 38

Sodium 4-[(1-Benzoyloxyisobutoxy)carbonylamino]-(3R)-(4-chlorophenyl)-butanoate (42)

Following the procedure of Example 6 and replacing compound (9) with compound (41), the product in its protonated acid form was obtained as a pair of diasteromers in 59% yield. $^1$H NMR (CDCl$_3$, 400 MHz): δ 8.02 (d, 2H), 7.56 (t, 1H), 7.43 (t, 3H), 7.21 (d, 2H), 7.11 (d, 2H), 6.77 (d, 1H), 4.71 (m, 1H), 3.54 (m, 1H), 3.31 (m. 2H), 2.72 (m, 1H), 2.60 (m, 1H), 0.2.11 (m, 1H), 1.00 (m, 6H). MS (ESI) m/z 432.25 (M-H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (42).

Example 39

Sodium 4-[(1-Pivaloyloxyisobutoxy)carbonylamino]-(3R)-(4-chlorophenyl)-butanoate Step A: O-(1-Chloroisobutoxy)S-Ethyl Thiocarbonate (44)

To a stirred solution of ethanethiol (1.23 mL, 16.7 mmol) and triethylamine (2.93 mL, 21.1 mmol) in CH$_2$Cl$_2$ at 0° C. was added 1-chloro-2-methylpropyl chloroformate (3.0 g, 17.5 mmol). The resulting mixture was stirred for 10 min. at 0° C., and then the reaction mixture was diluted with CH$_2$Cl$_2$, washed successively with dilute HCl and brine, then dried over anhydrous Na$_2$SO$_4$. After concentration in vacuo the crude O-(1-chloroisobutoxy) S-ethyl thiocarbonate (44) was obtained, and used directly in the next step without further purification. $^1$H NMR (CDCl$_3$, 400 MHz): δ 1.05 (t, 6H), 1.35 (t, 3H), 2.17 (m, 1H), 2.90 (q, 2H), 6.33 (d, 1H).

Step B: O-(1-Pivaloyloxyisobutoxy)S-Ethyl Thiocarbonate (45)

A mixture of (44) (936 mg, 4.76 mmol), pivalic acid (2.43 g, 23.8 mmol) and N,N-diisopropylethylamine (2.40 g, 23.8 mmol) was stirred at 75° C. for four days, and the reaction was judged complete by $^1$H-NMR. The reaction mixture was cooled to room temperature and portioned between water and ether, the ether phase was washed successively with water, aqueous NaHCO$_3$, and brine, then dried over anhydrous Na$_2$SO$_4$. After rotary evaporation, the crude O-(1-pivaloyloxyisobutoxy) S-ethyl thiocarbonate (45) was obtained in quantitative yield, and used in the next step without further purification. $^1$H NMR (CDCl$_3$, 400 MHz): δ 0.96 (d, 6H), 1.21 (d, 9H), 1.30 (t, 3H), 2.03 (m, 1H), 6.65 (d, 1H).

Step C: (1-Pivaloyloxyisobutoxy)Chloroformate (46)

A solution of (45) (4.76 mmol) in CH$_2$Cl$_2$ at 0° C. was treated with sulfuryl chloride (11 mmol) under N$_2$ for 10 min, then the reaction mixture was concentrated to dryness in vacuo to afford the crude chloroformate (46) in quantitative yield, which used in the next step without further purification. $^1$H NMR (CDCl$_3$, 400 MHz): δ 1.00 (d, 6H), 1.20 (d, 9H), 2.143 (m, 1H), 6.54 (d, 1H).

Step D: [(1-Pivaloyloxyisobutoxy)carbonyloxy]Succinimide (47)

To a solution of N-hydroxysuccinimide (1.2 eq.) and pyridine (2.4 eq.) in CH$_2$Cl$_2$ at 0° C. was added an equimolar solution of the above chloroformate (46) in CH$_2$Cl$_2$. The resulting reaction mixture was stirred at 0° C. for 1 h, then was washed successively with water, dilute HCl and brine, then dried over Na$_2$SO$_4$. After removal of the solvent in vacuo, the crude N-hydroxysuccinimidyl carbonate (47) was obtained in quantitative yield, and was used in the next step without further purification.

Step E: Sodium 4-[(1-Pivaloyloxyisobutoxy)carbonylamino]-(3R)-(4-chlorophenyl)-butanoate (43)

To a stirred solution of R-baclofen (1 g, 4.69 mmol) and NaHCO$_3$ (394 mg, 4.69 mmol) in water was added a solution of (47) (4.69 mmol) in acetonitrile. The resulting reaction mixture was stirred at room temperature for 1 h, then acidified to pH 5 with 10% HCl, extracted with ethyl acetate, washed with brine, and dried over anhydrous Na$_2$SO$_4$. The solvent was removed in vacuo to afford the crude product, which was purified by preparative LC/MS to afford 146 mg of the product in its acid form. $^1$H NMR (CDCl$_3$, 400 MHz): δ 0.88 (m, 6H), 1.15 (d, 9H), 1.92 (m, 1H), 2.54 (m, 1H), 2.67 (m, 1H), 3.27 (m, 2H), 3.42 (m, 1H), 4.83 (t, 1H), 7.08 (d, 2H), 7.21 (d, 2H). MS (ESI) m/z 412.30 (M–H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (43).

Example 40

Sodium 4-[(1-Propanoyloxyisobutoxy)carbonylamino]-(3R)-(4-chlorophenyl)-butanoate (48)

Following the procedures of Example 39 and replacing pivalic acid with propionic acid in Step B afforded the title compound in its acid form. $^1$H NMR (CDCl$_3$, 400 MHz): δ 0.90 (m, 6H), 1.14 (t, 3H), 1.96 (m, 1H), 2.33 (m, 2H), 2.64 (m, 1H), 2.72 (m, 1H), 3.52-3.28 (m, 3H), 4.69 (m, 1H), 6.51 (d, 1H), 7.12 (m, 2H), 7.27 (m, 2H). MS (ESI) m/z 384.10 (M–H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (48).

Example 41

Sodium 4-[(1-Cyclopentylcarbonyloxyisobutoxy) carbonylamino]-(3R)-(4-chlorophenyl)-butanoate (49)

Following the procedures of Example 39 and replacing pivalic acid with cyclopentanecarboxylic acid in Step B afforded the title compound in its acid form. $^1$H NMR (CDCl$_3$, 400 MHz): δ 0.91 (m, 6H), 1.53-1.98 (m, 9H), 2.56-2.74 (m, 3H), 3.31 (m, 2H), 3.45 (m, 1H), 4.71 (m, 1H), 6.49 (d, 1H), 7.10 (q, 2H), 7.24 (m, 2H). MS (ESI) m/z 424.11 (M–H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (49).

Example 42

Sodium 4-[(1-Cyclohexylcarbonyloxyisobutoxy) carbonylamino]-(3R)-(4-chlorophenyl)-butanoate (50)

Following the procedures of Example 39 and replacing pivalic acid with cyclohexanecarboxylic acid in Step B afforded the title compound in its acid form. $^1$H NMR (CDCl$_3$, 400 MHz): δ 0.89 (m, 6H), 1.22 (m, 3H), 1.40 (m, 2H), 1.61 (m, 1H), 1.70 (m, 2H), 1.89 (m, 3H), 2.27 (m, 1H), 2.58 (m, 1H), 2.70 (m, 1H), 3.29 (m, 2H), 3.23 (m, 1H), 4.73 (br.s, 1H), 6.48 (m, 1H), 7.10 (dd, 2H), 7.24 (dd, 2H). MS (ESI) m/z 438.14 (M–H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (50).

Example 43

Sodium 4-[(2,2-Diethoxypropanoyloxymethoxy) carbonylamino]-(3R)-(4-chlorophenyl)-butanoate (51)

Step A: Benzyl 4-[(2,2-Diethoxypropanoyloxymethoxy)-carbonylamino]-(3R)-(4-chlorophenyl)-butanoate (52)

A suspension of compound (8) (230 mg, 0.528 mmol) and cesium 2,2-diethoxypropionate (233 mg, 0.792 mmol) in DMF was stirred at 40° C. for 1 h then cooled to room temperature. The reaction mixture was partitioned between ice-water and ethyl acetate, and the organic phase was washed with brine, dried over anhydrous Na$_2$SO$_4$, and concentrated in vacuo to afford the crude product, which was purified by chromatography on silica gel, eluting with a mixture of 20% ethyl acetate in hexane to give the title compound (52). $^1$H NMR (CDCl$_3$, 400 MHz): δ 1.18-1.27

(m, 6H), 2.68 (m, 1H), 2.80 (m, 1H), 3.33-3.58 (m, 7H), 4.99 (m, 3H), 5.75 (s, 2H), 7.08-7.29 (m, 9H).

Step B: Sodium 4-[(2,2-Diethoxypropanoyloxymethoxy)-carbonylamino]-(3R)-(4-chlorophenyl)-butanoate (51)

Following the procedure of Example 6 and replacing compound (9) with (52) afforded the title compound in its acid form. $^1$H NMR (CDCl$_3$, 400 MHz): δ 1.20 (t, 6H), 2.59 (dd, 1H), 2.69 (dd, 1H), 3.31-3.61 (m, 7H), 5.15 (m, 1H), 5.76 (s, 2H), 7.11 (d, 2H), 7.26 (d, 2H). MS (ESI) m/z 430.14 (M−H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (51).

Example 44

Sodium 4-[(4-Methoxybenzoyloxymethoxy)carbonylamino]-(3R)-(4-chlorophenyl)-butanoate (53)

Following the same procedures of Example 39 but replacing 1-chloro-2-methylpropyl chloroformate with chloromethyl chloroformate in Step A and replacing pivalic acid with p-anisic acid in Step B afforded the title compound in its acid form. $^1$H NMR (CDCl$_3$, 400 MHz): δ 2.60 (dd, 1H), 2.70 (dd, 1H), 3.33 (m, 2H), 3.50 (m, 1H), 3.83 (s, 3H), 5.24 (m, 1H), 5.87 (s, 2H), 6.88 (d, 2H), 7.09 (d, 2H), 7.20 (d, 2H), 7.96 (d, 2H). MS (ESI) m/z 420.11 (M−H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (53).

Example 45

Sodium 4-[(Nicotinoyloxymethoxy)carbonylamino]-(3R)-(4-chlorophenyl)-butanoate (54)

Following the same procedures of Example 39 but replacing 1-chloro-2-methylpropyl chloroformate with chloromethyl chloroformate in Step A and replacing pivalic acid with nicotinic acid in Step B afforded the title compound in its acid form. $^1$H NMR (CD$_3$OD 400 MHz): δ 2.55 (dd, 1H), 2.70 (dd, 1H), 3.29 (m, 3H), 5.90 (s, 2H), 7.19 (m, 5H), 7.55 (dd, 1H), 8.35 (d, 1H), 8.74 (dd, 1H), 9.09 (s, 1H). MS (ESI) m/z 393.11 (M+H)$^+$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (54).

Example 46

Sodium 4-[(Cyclopentylcarbonyloxymethoxy)carbonylamino]-(3R)-(4-chlorophenyl)-butanoate (55)

Following the same procedures of Example 39 but replacing 1-chloro-2-methylpropyl chloroformate with chloromethyl chloroformate in Step A and replacing pivalic acid with cyclopentanecarboxylic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (55). $^1$H NMR (CD$_3$OD 400 MHz): δ 1.57-1.88 (m. 8H), 2.54 (m, 1H), 2.72 (m, 2H), 3.29 (m, 3H), 5.61 (q, 2H), 7.23 (m, 4H). MS (ESI) m/z 381.91 (M−H)$^-$.

Example 47

Sodium 4-[(2-Furoyloxymethoxy)carbonylamino]-(3R)-(4-chlorophenyl)-butanoate (56)

Following the same procedures of Example 39 but replacing 1-chloro-2-methylpropyl chloroformate with chloromethyl chloroformate in Step A and replacing pivalic acid with 2-furoic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (56). $^1$H NMR (CD$_3$OD 400 MHz): δ 2.37 (dd, 1H), 2.52 (dd, 1H), 3.29 (m, 3H), 5.77 (q, 2H), 6.61 (d, 1H), 7.20 (m, 4H), 7.23 (d, 1H), 7.76 (d, 1H). MS (ESI) m/z 379.99 (M−H)$^-$.

Example 48

Sodium 4-[(2-Thienylcarbonyloxymethoxy)carbonylamino]-(3R)-(4-chlorophenyl)-butanoate (57)

Following the same procedures of Example 39 but replacing 1-chloro-2-methylpropyl chloroformate with chloromethyl chloroformate in Step A and replacing pivalic acid with thiophene-2-carboxylic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (57). $^1$H NMR (CD$_3$OD 400 MHz): δ 2.39 (dd, 1H), 2.52 (dd, 1H), 3.30 (m, 3H), 5.80 (AB q, 2H), 7.16 (m, 5H), 7.80 (m, 2H). MS (ESI) m/z 419.77 (M+Na)$^+$.

Example 49

Sodium 4-[(Phenylacetoxymethoxy)carbonylamino]-(3R)-(4-chlorophenyl)-butanoate (58)

Following the same procedures of Example 39 but replacing 1-chloro-2-methylpropyl chloroformate with chloromethyl chloroformate in Step A and replacing pivalic acid with phenylacetic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (58). $^1$H NMR (CD$_3$OD 400 MHz): δ 2.38 (dd, 1H), 2.51 (dd, 1H), 3.29 (m, 3H), 5.61 (AB q, 2H), 7.24 (m, 9H). MS (ESI) m/z 403.91 (M−H)$^-$.

Example 50

Sodium 4-[(3-Methylbutanoyloxymethoxy)carbonylamino]-(3R)-(4-chlorophenyl)-butanoate (59)

Following the same procedures of Example 39 but replacing 1-chloro-2-methylpropyl chloroformate with chloromethyl chloroformate in Step A and replacing pivalic acid with isovaleric acid in Step B afforded the title compound in its acid form.

The carboxylic acid was converted to the sodium salt by dissolution in MeCN (0.5 mL) and then addition of aqueous NaHCO$_3$. (1 eq.) with sonication for 10 min. The solvent was removed by lyophilization to afford the title compound (59). $^1$H NMR (CD$_3$OD 400 MHz): δ 0.94 (d, 6H), 2.03 (m, 1H), 2.19 (d, 2H), 2.53 (m, 1H), 2.70 (m, 1H), 3.29 (m, 3H), 5.62 (AB q, 2H), 7.23 (m, 4H). MS (ESI) m/z 394.03 (M+Na)$^+$.

Example 51

Sodium 4-[(Pentanoyloxymethoxy)carbonylamino]-(3R)-(4-chlorophenyl)-butanoate (60)

Following the same procedures of Example 39 but replacing 1-chloro-2-methylpropyl chloroformate with chloromethyl chloroformate in Step A and replacing pivalic acid with valeric acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (60). $^1$H NMR (CD$_3$OD 400 MHz): δ 0.91 (t, 3H), 1.33 (m, 2H), 1.56 (p, 2H), 2.31 (t, 2H) 2.42 (m, 1H), 2.56 (m, 1H), 3.30 (m, 3H), 5.59 (AB q, 2H), 7.22 (m, 4H). MS (ESI) m/z 394.15 (M+Na)$^+$.

Example 52

Sodium 4-[(Cinnamoyloxymethoxy)carbonylamino]-(3R)-(4-chlorophenyl)-butanoate (61)

Following the same procedures of Example 39 but replacing 1-chloro-2-methylpropyl chloroformate with chloromethyl chloroformate in Step A and replacing pivalic acid with cinnamic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (61). $^1$H NMR (CD$_3$OD 400 MHz): δ 2.39 (dd, 1H), 2.53 (d, 1H), 3.29 (m, 3H), 5.72 (AB q, 2H), 6.49 (d, 1H), 7.21 (m, 4H), 7.31 (m, 3H), 7.61 (m, 2H), 7.72 (d, 1H). MS (ESI) m/z 440.14 (M+Na)$^+$.

Example 53

Sodium 4-[(3-Phenylpropionoyloxymethoxy)carbonylamino]-(3R)-(4-chlorophenyl)-butanoate (62)

Following the same procedures of Example 39 but replacing 1-chloro-2-methylpropyl chloroformate with chloromethyl chloroformate in Step A and replacing pivalic acid with dihydrocinnamic acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (62). $^1$H NMR (CD$_3$OD 400 MHz): δ 2.39 (dd, 1H), 2.52 (dd, 1H), 2.61 (t, 2H), 2.88 (t, 2H), 3.29 (m, 3H), 5.58 (s, 2H), 7.21 (m, 9H). MS (ESI) m/z 442.14 (M+Na)$^+$.

Example 54

Sodium 4-[(2-Methylbutanoyloxymethoxy)carbonylamino]-(3R)-(4-chlorophenyl)-butanoate (63)

Following the same procedures of Example 39 but replacing 1-chloro-2-methylpropyl chloroformate with chloromethyl chloroformate in Step A and replacing pivalic acid with 2-methylbutyric acid in Step B afforded the title compound in its acid form.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (63) as a pair of diasteromers. $^1$H NMR (CD$_3$OD 400 MHz): δ 0.87 (dt, 3H), 1.08 (dd, 3H), 1.44 (m, 1H), 1.60 (m, 1H), 2.36 (m, 2H), 2.50 (m, 1H), 3.29 (m, 3H), 5360 (AB q, 2H), 7.21 (m, 4H). MS (ESI) m/z 394.04 (M+Na)$^+$.

Example 55

Sodium 4-[1 (1-Cyclopentanecarbonyloxybutoxy)carbonylamino]-(3R)-(4-chlorophenyl)-butanoate (64)

Step A: 1-Chlorobutyl Chloroformate (65)

To a solution of triphosgene (4.94 g, 16.6 mmol) and n-butyraldehyde (3.0 g, 41.6 mmol) in anhydrous ether (30 mL) at 0° C. was added pyridine (0.67 mL, 8.32 mmol) dropwise. The resulting suspension was stirred at 0° C. for 30 min. The reaction mixture was filtered through a pad of Celite and the supernatant was concentrated on a rotary evaporator, affording the title chloroformate (4.38 g, 62%), which was used in the next step without further purification. $^1$H NMR (CDCl$_3$, 400 MHz): δ 0.95 (t, 3H), 1.51 (m, 2H), 2.04 (m, 2H), 6.30 (t, 1H).

Step B: O-(1-Chlorobutoxy)S-Ethyl Thiocarbonate (66)

To a solution of ethanethiol (1.8 mL, 24.3 mmol) and triethylamine (4.3 mL, 30.7 mmol) in CH$_2$Cl$_2$ at 0° C. was added chloroformate (65) (4.38 g, 25.6 mmol) in CH$_2$Cl$_2$. The resulting reaction mixture was stirred for 10 min at 0° C., then was washed successively with water, dilute HCl and brine. The organic phase was dried over anhydrous Na$_2$SO$_4$. After concentration in vacuo the crude O-(1-chlorobutoxy) S-ethyl thiocarbonate (66) (3.99 g) was obtained, and used directly in the next step without further purification. $^1$H NMR (CDCl$_3$, 400 MHz): δ 0.96 (t, 3H), 1.34 (t, 3H), 1.50 (m, 2H), 2.00 (m, 2H), 2.90 (m, 2H), 6.47 (t, 2H).

Step C: O-(1-Cyclopentanecarbonyloxybutoxy)S-Ethyl Thiocarbonate (67)

A mixture of (66) (1.33 g, 6.76 mmol) and cyclopentancarboxylic acid (1.30 g, 10.1 mmol) was stirred at 75° C. for five days. The reaction was then cooled to room temperature and partitioned between water and ether. The ether layer was washed with brine, dried over anhydrous Na$_2$SO$_4$. Filtration then removal of the solvent by rotary evaporation gave the title thiocarbonate (67) (1.62 g, 86%). $^1$H NMR (CDCl$_3$, 400 MHz): δ 0.95 (t, 3H), 1.20-1.85 (m, 15H), 2.68 (m, 1H), 2.82 (m, 2H). 6.84 (t, 1H).

Step D: [(1-Cyclopentanecarbonyloxybutoxy)carbonyloxy]Succinimide (68)

A solution of (67) (1.83 g, 6.34 mmol) in CH$_2$Cl$_2$ at 0° C. was treated with sulfuryl chloride (0.62 mL, 7.61 mmol) under N$_2$ for 10 min, then the reaction mixture was concentrated to dryness in vacuo to afford crude (1-cyclopentanecarbonyloxy-butoxy) chloroformate in quantitative yield. The chloroformate was dissolved in CH$_2$Cl$_2$, and was added to a mixture of N-hydroxysuccinimide (1.09 g, 9.51 mmol) and pyridine (1.28 mL, 15.8 mmol) in CH$_2$Cl$_2$ at 0° C. The reaction mixture was stirred at 0° C. for 1 h, then was washed with water, dilute HCl and brine and dried over Na$_2$SO$_4$. After removal of solvent in vacuo the title N-hydroxysuccinimidyl carbonate (68) was obtained in quantitative yield, and was used in the subsequent step without further purification.

Step E: Sodium 4-[(1-Cyclopentanecarbonyloxybutoxy)-carbonylamino]-(3R)-(4-chlorophenyl)-butanoate (64)

To a solution of R-baclofen (644 mg, 3.02 mmol) and NaHCO$_3$ (323 mg, 3.848 mmol) in water at room temperature was added a solution of (68) (900 mg, 2.749 mmol) in acetonitrile. The resulting reaction mixture was stirred for 1 h at that temperature, then was acidified to pH 4 with 10% HCl, and extracted with ethyl acetate. The combined organic phase was washed with brine and dried over anhydrous Na$_2$SO$_4$. Filtration and removal of the solvent in vacuo gave the crude product, which was purified by preparative LC/MS to afford the acid form of the title compound as a pair of diastereomers (636 mg, 75%).

The carboxylic acid was converted to the sodium salt by dissolution in MeCN (1 mL) and then addition of aqueous NaHCO$_3$ (1 eq.) with sonication for 10 mm. The solvent was removed by lyophilization to afford the title compound (64). $^1$H NMR (CD$_3$OD, 400 MHz): δ 0.92 (m, 3H), 1.36 (m, 2H), 1.56-1.87 (m, 10H), 2.41 (m, 1H), 2.52 (m, 1H), 2.70 (m, 1H), 3.29 (m, 3H), 6.59 (q, 1H), 7.22 (m, 4H). MS (ESI) m/z 448.7 (M+Na)$^+$.

Example 56

Sodium 4-[(1-Cyclohexanecarbonyloxybutoxy)carbonylamino]-(3R)-(4-chlorophenyl)-butanoate (69)

Following the same procedures of Example 55 but replacing cyclopentanecarboxylic acid with cyclohexanecarboxylic acid afforded the title compound (69) as a pair of diastereomers (596 mg). $^1$H NMR (CD$_3$OD, 400 MHz): δ 0.94 (m, 3H), 1.33 (m, 7H), 1.61-1.83 (m, 7H), 2.26 (m, 1H), 2.41 (m, 1H), 2.51 (m, 1H), 3.30 (m, 3H), 6.59 (m, 1H), 7.21 (m, 4H). MS (ESI) m/z 462.76 (M+Na)$^+$.

Example 57

Sodium 4-[(1-Hexanoyloxybutoxy)carbonylamino]-(3R)-(4-chlorophenyl)-butanoate (70)

Following the same procedures of Example 55 but replacing cyclopentanecarboxylic acid with hexanoic acid afforded the title compound (70) as a pair of diastereomers (894 mg). $^1$H NMR (CD$_3$OD, 400 MHz): δ 0.92 (m, 6H), 1.31 (m, 6H), 1.55-1.70 (m, 4H), 2.64 (m, 2H), 2.40 (m, 1H), 2.53 (m, 1H), 3.30 (m, 3H), 6.61 (m, 1H), 7.22 (s, 4H). MS (ESI) m/z 450.76 (M+Na)$^+$.

Example 58

Sodium 4-[(1-Benzoyloxybutoxy)carbonylamino]-(3R)-(4-chlorophenyl)-butanoate (71)

Following the same procedures of Example 55 but replacing cyclopentanecarboxylic acid with benzoic acid afforded the title compound (71) as a pair of diastereomers (100 mg). $^1$H NMR (CDCl$_3$, 400 MHz): δ 0.71 (m, 3H), 1.14 (m, 2H), 1.48 (m, 2H), 2.72 (m, 2H), 3.35 (m, 2H), 3.50 (m, 1H), 5.32 (br.m, 1H), 6.80 (m, 1H), 7.22 (m, 2H), 7.40 (m, 1H), 7.75 (m, 2H). MS (ESI) m/456.10 (M+Na)$^+$.

Example 59

Sodium 4-[(1-Isobutanoyloxybutoxy)carbonylamino]-(3R)-(4-chlorophenyl)-butanoate (72)

Following the same procedures of Example 55 but replacing cyclopentanecarboxylic acid with isobutyric acid afforded the title compound (72) as a pair of diastereomers (70 mg). $^1$H NMR (CDCl$_3$, 400 MHz): δ 0.92 (m, 3H), 1.14 (m, 6H), 1.35 (m, 2H), 1.68 (m, 2H), 2.48-2.72 (m, 3H), 3.25-3.52 (m, 3H), 4.73 (br. m, 1H), 6.65 (t, 1H), 7.11 (d, 2H), 7.25 (d, 2H). MS (ESI) m/z 422.14 (M+Na)$^+$.

Example 60

Sodium 4-[(1-Butanoyloxybutoxy)carbonylamino]-(3R)-(4-chlorophenyl)-butanoate (73)

Following the same procedures of Example 55 but replacing cyclopentanecarboxylic acid with n-butyric acid afforded the title compound (73) as a pair of diastereomers (122 mg). $^1$H NMR (CDCl$_3$, 400 MHz): δ 0.85 (m, 6H), 1.24 (m, 2H), 1.52 (m, 4H), 2.14 (m, 2H), 2.35 (m, 2H), 3.03-3.23 (2H), 3.35 (m, 1H), 5.40 (br.s, 1H), 6.61 (m, 1H), 6.98 (d, 2H), 7.08 (m, 2H). MS (ESI) m/z 422.14 (M+Na)$^+$.

Example 61

Sodium 4-[(1-Acetoxybutoxy)carbonylamino]-(3R)-(4-chlorophenyl)-butanoate (74)

Following the same procedures of Example 55 but replacing cyclopentanecarboxylic acid with acetic acid afforded the title compound (74) as a pair of diastereomers (600 mg). $^1$H NMR (CD$_3$OD, 400 MHz): δ 0.92 (m, 3H), 1.35 (m, 2H), 1.67 (m, 2H), 1.99 (2s, 3H), 2.55 (m, 1H), 2.70 (m, 1H), 3.29 (m, 3H), 6.60 (q, 1H), 7.25 (m, 4H). MS (ESI) m/z 394.20 (M+Na)$^+$.

Example 62

Sodium 4-[(1-Propionyloxybutoxy)carbonylamino]-(3R)-(4-chlorophenyl)-butanoate (75)

Following the same procedures of Example 55 but replacing cyclopentanecarboxylic acid with propionic acid afforded the title compound (75) as a pair of diastereomers (405 mg). $^1$H NMR (CD$_3$OD, 400 MHz): δ 0.93 (m, 3H), 1.08 (m, 3H), 1.33 (m, 2H), 1.64 (m, 2H), 2.22-2.33 (m, 2H), 2.39 (m, 1H), 2.50 (m, 1H), 2.30 (m, 3H), 6.60 (m, 1H), 7.22 (s, 4H). MS (ESI) m/z 408.11 (M+Na)$^+$.

Example 63

Sodium 4-[(1-Cyclohexanecarbonyloxypropoxy)carbonylamino]-(3R)-(4-chlorophenyl)-butanoate (76)

Following the same procedures of Example 55 but replacing butyraldehyde with propionaldehyde in Step A and replacing cyclopentanecarboxylic acid with cyclohexanecarboxylic acid in Step C afforded the title compound (76) as a pair of diastereomers (700 mg). $^1$H NMR (CD$_3$OD, 400 MHz): δ 0.87 (m, 3H), 1.25-1.39 (m, 5H), 1.62-1.86 (m, 7H), 2.1-2.54 (m, 3H), 3.29 (m, 3H), 6.51 (m, 1H), 7.21 (m, 4H). MS (ESI) m/z 448.20 (M+Na)$^+$.

Example 64

Sodium 4-[(1-Isobutanoyloxypropoxy)carbonylamino]-(3R)-(4-chlorophenyl)-butanoate (77)

Following the same procedures of Example 63 but replacing cyclohexanecarboxylic acid with isobutyric acid afforded the title compound (77) as a pair of diastereomers (140 mg). $^1$H NMR (CD$_3$OD, 400 MHz): δ 0.86-0.92 (m, 3H), 1.06-1.13 (m, 6H), 1.69 (m, 2H), 2.36-2.55 (m, 3H), 3.30 (m, 3H), 6.51 (m, 1H), 7.22 (s, 4H). MS (ESI) m/z 408.11 (M+Na)$^+$.

Example 65

Sodium 4-[(1-Butanoyloxypropoxy)carbonylamino]-(3R)-(4-chlorophenyl)-butanoate (78)

Following the same procedures of Example 63 but replacing cyclohexanecarboxylic acid with n-butyric acid afforded the title compound (78) as a pair of diastereomers (1.09 g). $^1$H NMR (CD$_3$OD, 400 MHz): δ 0.91 (m, 6H), 1.59 (m, 2H), 1.69 (m, 2H), 2.23-2.25 (m, 2H), 2.40 (m, 1H), 2.51 (m, 1H), 3.29 (m, 3H), 6.56 (q, 1H), 7.22 (s, 4H). MS (ESI) m/z 408.73 (M+Na)$^+$.

Example 66

Sodium 4-[(1-Propionoyloxypropoxy)carbonylamino]-(3R)-(4-chlorophenyl)-butanoate (79)

Following the same procedures of Example 63 but replacing cyclohexanecarboxylic acid with propionic acid afforded the title compound (79) as a pair of diastereomers (100 mg). $^1$H NMR (CD$_3$OD, 400 MHz): δ 0.88 (m, 3H), 1.08 (m, 3H), 2.21 (m, 1H), 2.25 (m, 2H), 2.39 (m, 1H), 2.50 (m, 1H), 3.30 (m, 3H), 6.52 (q, 1H), 7.22 (s, 4H). MS (ESI) m/z 394.08 (M+Na)$^+$.

Example 67

Sodium 4-[(1-Pivaloyloxypropoxy)carbonylamino]-(3R)-(4-chlorophenyl)-butanoate (80)

Following the same procedures of Example 63 but replacing cyclohexanecarboxylic acid with pivalic acid afforded the title compound (80) as a pair of diastereomers (420 mg). $^1$H NMR (CD$_3$OD, 400 MHz): δ 0.90 (m, 3H), 1.10 (s, 4.5H), 1.16 (s, 4.5H), 1.70 (m, 2H), 2.47-2.55 (m, 2H), 3.30 (m, 3H), 6.50 (dt, 1H), 7.22 (s, 4H). (ESI) m/z 422.07 (M+Na)$^+$.

Example 68

Sodium 4-[(1-Benzoyloxypropoxy)carbonylamino]-(3R)-(4-chlorophenyl)-butanoate (81)

Following the same procedures of Example 63 but replacing cyclohexanecarboxylic acid with benzoic acid afforded the title compound (81) as a pair of diastereomers (129 mg). $^1$H NMR (CD$_3$OD, 400 MHz): δ 0.98 (m, 3H), 1.85 (m, 2H), 2.39 (m, 1H), 2.52 (m, 1H), 3.30 (m, 3H), 6.78 (m, 1H), 7.18 (m, 4H), 7.48 (m, 2H), 7.60 (m, 1H), 7.95 (m, 2H). MS (ESI) m/z 442.07 (M+Na)$^+$.

Example 69

Sodium 4-[(1-Acetoxy-1-cyclohexylmethoxy)carbonylamino]-(3R)-(4-chlorophenyl)-butanoate (82)

Following the same procedures of Example 55 but replacing butyraldehyde with cyclohexanecarboxaldehyde in Step A and replacing cyclopentanecarboxylic acid with acetic acid in Step C afforded the title compound (82) as a pair of diastereomers (759 mg). $^1$H NMR (CD$_3$OD, 400 MHz): δ 0.94-1.28 (m, 4H), 1.60-1.80 (m, 6H), 1.98 (s, 1.5H), 2.01 (s, 1.5H), 2.39 (m, 1H), 2.51 (m, 1H), 3.30 (m, 3H), 6.40 (M, 1H), 7.22 (s, 4H). MS (ESI) m/z 434.73 (M+Na)$^+$.

Example 70

Sodium 4-[(1-Propionyloxy-1-cyclohexylmethoxy)carbonylamino]-(3R)-(4-chlorophenyl)-butanoate (83)

Following the same procedures of Example 55 but replacing butyraldehyde with cyclohexanecarboxaldehyde in Step A and replacing cyclopentanecarboxylic acid with propionic acid in Step C afforded the title compound (83) as a pair of diastereomers (310 mg). $^1$H NMR (CD$_3$OD, 400 MHz): δ 0.96-1.30 (m, 7H), 1.58-1.80 (m, 6H), 2.24-2.42 (m, 3H), 2.53 (m, 1H), 3.30 (m, 3H), 6.42 (q, 1H), 7.21 (s, 4H). MS (ESI) m/z 448.10 (M+Na)$^+$.

Example 71

Sodium 4-[(1-Isobutanoyloxy-1-cyclohexylmethoxy)carbonylamino]-(3R)-(4-chlorophenyl)-butanoate (84)

Following the same procedures of Example 55 but replacing butyraldehyde with cyclohexanecarboxaldehyde in Step A and replacing cyclopentanecarboxylic acid with isobutyric acid in Step C afforded the title compound (84) as a pair of diastereomers (800 mg). $^1$H NMR (CD$_3$OD, 400 MHz): δ 0.96-1.28 (m, 10H), 1.58-1.79 (m, 6H), 2.36-2.54 (m, 3H), 3.30 (m, 3H), 7.21 (s, 4H). MS (ESI) m/z 462.21 (M+Na)$^+$.

Example 72

Sodium 4-[(1-Butanoyloxy-1-cyclohexylmethoxy)carbonylamino]-(3R)-(4-chlorophenyl)-butanoate (85)

Following the same procedures of Example 55 but replacing butyraldehyde with cyclohexanecarboxaldehyde in Step A and replacing cyclopentanecarboxylic acid with n-butyric acid in Step C afforded the title compound (85) as a pair of diastereomers (520 mg). $^1$H NMR (CD$_3$OD, 400 MHz): δ

0.92 (m, 3H), 0.98-1.28 (m, 4H), 1.54-1.78 (m, 8H), 2.24 (m, 2H), 2.39 (m, 1H), 2.53 (m, 1H), 3.29 (m, 3H), 6.41 (q, 1H). MS (ESI) m/z 462.06 (M+Na)$^+$.

Example 73

Asymmetric Synthesis of Sodium 4-{[(1S)-Butanoyloxybutoxy]carbonylamino}-(3R)-(4-chlorophenyl)-butanoate (86)

Step A: Synthesis of [(1S)-Butanoylbutoxy]-(4-nitrophenyl)-carbonate (87)

To a solution of (5S)-5-hydroxyoctan-4-one (1.10 g, 7.63 mmol) in CH$_2$Cl$_2$ (50 mL) at 0° C. was added p-nitrophenyl chloroformate (1.90 g, 9.14 mmol), pyridine (0.98 mL, 12.1 mmol) and 4-dimethylaminopyridine (186 mg, 1.52 mmol). The resulting mixture was stirred at 0° C. for 1 h then at room temperature overnight. The reaction mixture was diluted in CH$_2$Cl$_2$, washed excessively with water, dilute HCl and brine, and dried over anhydrous Na$_2$SO$_4$. Filtration and removal of the solvent in vacuo afforded the crude carbonate, which was purified by chromatography on silica gel, eluting with 5% ether in hexane to afford the title compound (87) (1.45 g, 65%). $^1$H NMR (CDCl$_3$, 400 MHz): δ 0.94 (t, 3H) 0.99 (t, 3H), 1.51 (hex, 2H), 1.66 (hex, 2H), 1.85 (m, 2H), 2.48 (m, 2H), 5.03 (AB q, 1H), 7.03 (d, 2H), 8.26 (d, 2H).

Step B: Synthesis of 4-{[(1S)-Butanoylbutoxy]carbonylamino}-(3R)-(4-chlorophenyl)-butanoic Acid (88)

To a stirred suspension of R-baclofen (1.0 g, 4.69 mmol) in CH$_2$Cl$_2$ (50 mL) at 0° C. was added triethylamine (2.4 mL, 18.76 mmol) and TMSCl (1.19 mL, 9.38 mmol). The resulting reaction mixture was stirred at 0° C. for 15 min. Then, to the suspension was added a solution of compound (87) (4.7 mmol) in CH$_2$Cl$_2$ (5 mL) and the resulting reaction mixture stirred at room temperature for 5 h. The mixture was diluted with CH$_2$Cl$_2$, washed with ice-cold dilute HCl and brine, and dried over anhydrous Na$_2$SO$_4$. The solvent was removed in vacuo to afford the crude product, which was purified by chromatography on silica gel, eluting first with pure CH$_2$Cl$_2$ to remove p-nitrophenol, and then with 20% ethyl acetate in CH$_2$Cl$_2$ to afford the carbamate compound (88) (1.20 g, 67%). $^1$H NMR (CDCl$_3$, 400 MHz): δ 0.90 (m, 6H), 1.33 (m, 2H), 1.60 (m, 4H), 2.39 (m, 2H), 2.58 (m, 1H), 2.71 (m, 1H), 3.3.25-3.50 (m, 3H), 4.90 (AB q, 1H), 5.06 (t, 1H), 7.13 (d, 2H), 7.26 (d, 2H).

Step C: 4-{[(1S)-Butanoyloxybutoxy]carbonylamino}-(3R)-(4-chlorophenyl)-butanoic Acid (89)

To a stirred suspension of urea-hydrogen peroxide (1.43 g, 15.2 mmol) in CH$_{12}$Cl$_2$ (30 mL) at 0° C. was added carbamate (88) (417 mg, 1.09 mmol) in CH$_2$Cl$_2$ (5 mL), followed by dropwise addition of trifluoroacetic anhydride (1.06 mL, 7.60 mmol). The resulting reaction mixture was stirred at 0° C. and quenched after 5 h. The reaction mixture was washed with water and brine, then dried over anhydrous Na$_2$SO$_4$ to afford the crude product, which was purified by preparative LC/MS to afford the title compound (89) (189 mg, 43.5%) as a single diastereomer (as determined by chiral LC/MS). $^1$H NMR (CDCl$_3$, 400 MHz): δ 0.92 (m, 6H), 1.38 (m, 2H), 1.65 (m, 4H), 2.28 (t, 2H), 2.59 (dd, 1H), 2.70 (dd, 1H), 3.29 (m, 2H), 3.50 (m, 1H), 4.78 (br. m, 1H), 6.67 (t, 1H), 7.11 (d, 2H), 7.26 (d, 2H). MS (ESI) m/z 398.14 (M−H)$^-$.

Step D: Sodium 4-{[(1S)-Butanoyloxybutoxy]carbonylamino}-(3R)-(4-chlorophenyl)-butanoate (86)

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (86).

Example 74

Asymmetric Synthesis of Sodium 4-{[(1R)-Butanoyloxyisobutoxy]carbonylamino}-(3R)-(4-chlorophenyl)-butanoate (90)

Following the procedures of Example 73 but replacing (5S)-5-hydroxyoctan-4-one with (3R)-3-hydroxy-2-methylheptan-4-one, the free acid form of the title compound was obtained as a single diastereomer (158 mg, 23%). $^1$H NMR (CDCl$_3$, 400 MHz): δ 0.91 (m, 9H) 1.63 (hept, 2H), 1.94 (m, 2H), 2.29 (t, 2H), 2.60 (dd, 1H), 2.71 (dd, 1H), 3.30 (m, 2H), 3.51 (m, 1H), 4.70 (t, 1H), 6.51 (d, 1H), 7.12 (d, 2H), 7.26 (d, 2H). MS (ESI) m/z 398.14 (M−H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (90).

Example 75

Asymmetric Synthesis of Sodium 4-{[(1S)-Isobutanoyloxybutoxy]carbonylamino}-(3R)-(4-chlorophenyl)-butanoate (91)

Following the procedures of Example 73 but replacing (5S)-5-hydroxyoctan-4-one with (4S)-4-hydroxy-2-methylheptan-3-one, the free acid form of the title compound was obtained as a single diastereomer (20 mg, 7%). $^1$H NMR (CDCl$_3$, 400 MHz): δ 0.93 (t, 3H), 1.16 (m, 6H), 1.34 (m, 2H), 1.68 (m, 2H), 2.52 (m, 1H), 2.58 (dd, 1H), 2.71 (dd, 1H), 3.30 (m, 2H), 3.52 (m, 1H), 4.70 (t, 1H), 6.67 (t, 1H), 7.12 (d, 2H), 7.26 (d, 2H). MS (ESI) m/z 398.14 (M−H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (91).

Example 76

Asymmetric Synthesis of Sodium 4-{[(1S)-Isobutanoyloxyisobutoxy]carbonylamino}-(3R)-(4-chlorophenyl)-butanoate (92)

Following the procedures of Example 73 but replacing (5S)-5-hydroxyoctan-4-one with (4S)-2,5-dimethyl-4-hydroxyhexan-3-one, the free acid form of the title compound was obtained as a single diastereomer (8.0 mg, 2%). $^1$H NMR (CDCl$_3$, 400 MHz): δ 0.89 (m, 6H), 1.15 (m, 6H), 1.94 (m, 1H), 2.52 (m, 1H), 2.58 (dd, 1H), 2.78 (dd, 1H), 3.28 (m, 2H), 3.49 (m, 1H), 4.68 (t, 1H), 6.48 (d, 1H), 7.10 (d, 2H), 7.24 (d, 2H). MS (ESI) m/z 398.14 (M−H)$^-$.

The carboxylic acid was converted to the sodium salt by dissolution in MeCN (0.5 mL) and then addition of aqueous NaHCO$_3$ (1 eq.) with sonication for 10 min. The solvent was removed by lyophilization to afford the title compound (92).

Example 77

Synthesis of O-(1-Isobutanoyloxyisobutoxy)S-Methyl Thiocarbonate (93)

Step A: O-(1-Chloroisobutoxy)S-Methyl Thiocarbonate (94)

A solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10 and 20° C. during the addition. The aqueous phase was separated and the organic phase was washed with brine (2×2 L) and water (2 L). The organic layer was dried over anhydrous Na$_2$SO$_4$, filtered, and concentrated under reduced pressure to afford the title compound (94) (1050 g, 5.76 mol, 96%) as a colorless liquid. $^1$H NMR (CDCl$_3$, 400 MHz): δ 1.1 (dd, 6H), 2.2 (m, 1H), 2.4 (s, 3H), 6.35 (d, 1H).

Step B: Tetramethylammonium Isobutyrate (95)

To a 20 L round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave the product (95) as an amber liquid, which was used without further purification.

Step C: O-(1-Isobutanoyloxyisobutoxy)S-Methyl Thiocarbonate (93)

To a 3 L three neck round bottom flask equipped with a mechanical stirrer and teflon-coated thermocouple was added (95) (1672 g, 9 mol), isobutyric acid (264 g, 1.5 mol), and (94) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated NaHCO$_3$ (1×2 L) and water (1 L). The organic phase was separated and concentrated under reduced pressure to afford the product (93) (905 g, 3.9 mol, 65%) as a colorless liquid. $^1$H NMR (CDCl$_3$, 400 MHz): δ 1.0 (d, 6H), 1.2 (dd, 6H), 2.05 (m, 1H), 2.35 (s, 3H), 2.6 (m, 1H), 6.7 (d, 1H).

Example 78

Synthesis of (1R)-1-[((3S,4S)-2,5-Dioxo-3,4-dibenzoyloxypyrrolidinyl)-oxycarbonyloxy]-2-methylpropyl2-methylpropanoate (96)

Step A: (3S,4S)-2,5-Dioxo-3,4-dibenzoyloxy-3,4-dihydrofuran (97)

A suspension of 2,3-dibenzoyl-D-tartaric acid (100 g, 279 mmol) in acetic anhydride (300 mL) was stirred at 85° C. for 2 h then the reaction mixture allowed to cool to room temperature. The crystalline product was collected by filtration, washed with a mixture of ether and hexane (1:1) and dried under vacuum to afford the title compound (97) (80 g, 84%). $^1$H NMR (CDCl$_3$, 400 MHz): δ 5.99 (s, 2H), 7.50 (m, 4H), 7.66 (m, 2H), 8.07 (m, 4H).

Step B: 1-Hydroxy-(3S,4S)-2,5-Dioxo-3,4-dibenzoyloxypyrrolidine (98)

To a suspension of (97) (60 g, 176 mmol) in a mixture of acetonitrile and water (8:1, 400 mL) at 0° C. was added a 50% aqueous solution of hydroxylamine (13.0 mL, 211 mmol). The resulting suspension was stirred overnight at room temperature to obtain a clear solution. The bulk of the acetonitrile was removed by rotary evaporation and the residue was portioned between ethyl acetate and water. The organic phase was washed successively with water and brine, dried over anhydrous Na$_2$SO$_4$ and concentrated in vacuo to afford the intermediate, 2,3-dibenzoyloxy D-tartaric acid mono-hydroxamate. This compound was suspended in toluene heated under reflux for 2 h, then cooled to room temperature to form a crystalline solid. The product was collected by filtration, washed with a mixture of ether and hexane (1:1), and dried under vacuum to afford the title compound (98) (58 g, 93%). $^1$H NMR (CDCl$_3$, 400 MHz): δ 6.06 (s, 2H), 7.50 (t, 4H), 7.65 (dt, 2H), 8.06 (m, 4H). MS (ESI) m/z 354.00 (M–H)$^-$.

Step C: (1R)-1-[((3S,4S)-2,5-Dioxo-3,4-dibenzoyloxypyrrolidinyl)-oxycarbonyloxy]-2-methylpropyl 2-methylpropanoate (96)

To a stirred solution of compound (98) (35 g, 98.6 mmol) and thiocarbonate (93) (34.6 g, 148 mmol) in dichloromethane at 0° C. was dropwise added a 32% solution of peracetic acid (300 mmol) in acetic acid over 2 h. The reaction temperature was kept below 35° C. during the addition of peracetic acid. After the addition was complete, the reaction mixture was stirred overnight at room temperature. The resulting white precipitate was filtered and washed successively with water, and a mixture of ether and hexane (1:2), then dried under vacuum to afford the crude title compound. This product was crystallized once from a mixture of ethyl acetate and hexane (1:1) to afford the title compound (96) (13.7 g, 25%). The diastereomeric purity of the product was determined to be 98.4% d.e. by HPLC using a chiral column. $^1$H NMR (CDCl$_3$, 400 MHz): δ 1.06 (d, 6H), 1.22 (d, 3H), 1.22 (d, 3H), 2.20 (m, 1H), 2.64 (hept. 1H), 6.01 (br. s, 2H), 6.64 (d, 1H), 7.47 (m, 4H), 7.63 (m, 2H), 8.07 (m, 4H).

Example 79

Synthesis of 4-{[(1R)-Isobutanoyloxyisobutoxy]carbonylamino}-(3R)-(4-chlorophenyl)-butanoic Acid (99)

To a stirred suspension of (96) (11.7 g, 21.7 mmol) in a mixture of THF and water (10:1) (220 mL) at room temperature was added R-baclofen (4.78 g, 22.5 mmol). The resulting reaction mixture was stirred until the suspension became a clear solution (ca. 2 h) then was concentrated in vacuo to remove most of the solvent. The residue was partitioned between ether and water, the ether layer was washed with water and brine, and dried over anhydrous Na$_2$SO$_4$. After filtration and concentration in vacuo, the crude product was obtained and then purified by flash-chromatography on silica gel, eluting with a gradient of 10-20% acetone in hexane. Crystallization from an acetone/hexane mixture afforded the title compound (99) (8.22 g, 95% yield). The diastereomeric purity of the product was determined to be 99.9% d.e. by HPLC using a chiral column. $^1$H NMR (CDCl$_3$, 400 MHz): δ 0.95 (d, 6H), 1.17 (d, 3H), 1.18 (d, 3H), 1.99 (m, 1H), 2.55 (hept. 1H), 2.64 (dd, 1H), 2.76 (dd, 1H), 3.40 (m, 3H), 4.73 (br. t, 1H), 6.51 (d, 1H), 7.13 (d, 2H), 7.27 (m, 2H). MS (ESI) m/z 398.50 (M−H)$^−$.

Example 80

Synthesis of Sodium 4-{[(1R)-Isobutanoyloxyisobutoxy]carbonylamino}-(3R)-(4-chlorophenyl)-butanoate (100)

The carboxylic acid (99) was converted to the sodium salt by dissolution in MeCN (0.5 mL) and then addition of aqueous NaHCO$_3$ (1 eq.) with sonication for 15 min. The solvent was removed by lyophilization to afford the title compound (100). $^1$H NMR (CD$_3$OD, 400 MHz): δ 0.93 (d, 3H), 0.94 (d, 3H), 1.08 (d, 3H), 1.10 (d, 3H), 1.94 (m, 1H), 2.37-2.54 (m, 3H), 3.31 (m, 3H), 6.43 (d, 1H), 7.23 (s, 4H). MS (ESI) m/z 398.57 (M−Na)$^−$.

Example 81

Synthesis of (1S)-1-[((3,R$^4$R)-2,5-Dioxo-3,4-dibenzoyloxypyrrolidinyl)-oxycarbonyloxy]-2-methylpropyl 2-methylpropanoate (101)

Step A: (3R,4R)-2,5-Dioxo-3,4-dibenzoyloxy-3,4-dihydrofuran (102)

To a 3-necked 5 L round bottom flask fitted with a mechanical stirrer and a teflon coated thermocouple was added (−)-2,3-dibenzoyl-L-tartaric acid (1000 g, 2.79 mol) followed by acetic anhydride (2 L). The suspension was stirred and heated to 85° C. for 2 h during which time the starting material gradually dissolved. A short time thereafter, the product began to crystallize in the reaction mixture and the suspension was then cooled to 25° C. The product was collected by filtration, washed with 10% acetone in hexane (2×1 L), and dried in a vacuum oven at 50° C. overnight to afford the title compound (102) as a white solid. $^1$H NMR (CDCl$_3$, 400 MHz): δ 6.0 (s, 2H), 7.45 (app. t, 4H), 7.65 (app. t, 2H), 8.05 (d, 4H).

Step B: 1-Hydroxy-(3R,4R)-2,5-Dioxo-3,4-dibenzoyloxypyrrolidine (103)

To a 3-neck 5 L round bottom flask fitted with a mechanical stirrer and a teflon coated temperature probe was added (102) (2.79 mol) followed by acetonitrile (2 L). The suspension was cooled in an ice bath to 4° C., followed by the addition of 50% aqueous hydroxylamine (180 mL, 2.93 mol) over 1 h. The starting material gradually dissolved during the addition and the reaction mixture was warmed to 20° C. and stirred for 1 h. The reaction mixture was concentrated in vacuo, diluted with EtOAc (1 L) and washed with 1 N HCl (2×1 L). The organic phase was separated and concentrated in vacuo to afford a viscous red syrup. The syrup was then heated for two hours in toluene (2.5 L) at 100° C. with azeotropic removal of water. The syrup gradually dissolved and then the product crystallized. After cooling to room temperature the solid was collected by filtration, washed with 10% acetone in hexane (2×1 L) and dried in a vacuum oven to afford the title compound (103) (862 g, 2.43 mol, 87%) as a white solid. $^1$H NMR (CDCl$_3$, 400 MHz): δ 5.85 (s, 2H), 7.45 (app. t, 4H), 7.65 (app t, 2H), 8.05 (m, 4H).

Step C: (1S)-1-[((3R,4R)-2,5-Dioxo-3,4-dibenzoyloxypyrrolidinyl)-oxycarbonyloxy]-2-methylpropyl 2-methylpropanoate (101)

A 3 L three necked round bottom flask fitted with a mechanical stirrer, teflon coated temperature probe and an addition funnel was charged with (93) (234 g, 1 mol), (103) (330 g, 0.95 mol), and 1,2-dichloroethane (2200 mL). The reaction mixture was cooled under a nitrogen atmosphere in an ice water bath to 15° C. To the stirred reaction mixture was added a 39% solution of peracetic acid in dilute acetic acid (500 mL, 2.94 mol) over 2 h, maintaining the temperature between 15 and 22° C. This temperature was maintained for an additional 12 h during which time a white precipitate was formed. The reaction mixture was further cooled to 3-4° C., the product collected by filtration, and washed with hexane (2×1 L). The product was dried in vacuo, yielding the title compound (101) (128 g, 0.24 mol, 25%). The diastereomeric purity of the product was determined to be >99% d.e. by HPLC using a chiral column. $^1$H NMR (CDCl$_3$, 400 MHz): δ 1.0 (d, 6H), 1.2 (dd, 6H), 2.1 (m, 1H), 2.65 (m, 1H), 6.0 (br. s, 2H), 6.6 (d, 1H), 7.45 (app. t, 4H), 7.65 (app. t, 2H), 8.05 (d, 4H).

Example 82

Synthesis of 4-{[(1S)-Isobutanoyloxyisobutoxy]carbonylamino}-(3R)-(4-chlorophenyl)-butanoic Acid (104)

To a 3 L three necked round bottom flask fitted with a mechanical stirrer, temperature probe, and nitrogen inlet was added (101) (75 g, 139 mmol), R-baclofen (31.2 g, 146 mmol), THF (1000 mL), and water (100 mL). The suspension was stirred under a nitrogen atmosphere at 18-20° C. for 4 h. The reaction became homogenous in 30 min. The THF was removed in vacuo and the reaction mixture was diluted with methyl tert-butyl ether (250 mL) and washed with 1N HCl (1×500 mL) and water (2×200 mL). The organic phase was separated and concentrated in vacuo to leave a white solid. The solid was purified by flash chromatography (800 g silica gel; eluting with 20% acetone in hexane) to afford the product (50 g, 125 mmol, 90% yield) as a white solid. Crystallization from either an acetone/hexane mixture or ethyl acetate/heptane mixture afforded the title compound (104) (50 g, 125 mmol, 90% yield) as a white solid. The diastereomeric purity of the product was determined to be >99% d.e. by HPLC using a chiral column. $^1$H NMR (CDCl$_3$, 400 MHz): δ 0.89 (m, 6H), 1.15 (m, 6H), 1.94 (m, 1H), 2.52 (m, 1H), 2.58 (dd, 1H), 2.78 (dd, 1H), 3.28 (m, 2H), 3.49 (m, 1H), 4.68 (t, 1H), 6.48 (d, 1H), 7.10 (d, 2H), 7.24 (d, 2H). MS (ESI) m/z 398.14 (M−H)$^−$.

Example 83

Synthesis of Sodium 4-{[(1S)-Isobutanoyloxyisobutoxy]carbonylamino}-(3R)-(4-chlorophenyl)-butanoate (92)

The carboxylic acid (101) was converted to the sodium salt by dissolution in MeCN and then addition of aqueous NaHCO$_3$ (1 eq.) with sonication for 15 min. The solvent was removed by lyophilization. Crystallization from either mixtures of acetone/hexane, ethyl acetate/heptane, THF/heptane or 1,2-dimethoxyethane/hexane afforded the title compound (92) as a white crystalline solid. $^1$H NMR (CD$_3$OD, 400 MHz): δ 0.90 (d, 6H), 1.14 (d, 3H), 1.15 (d, 3H), 1.91 (m, 1H), 2.40 (m, 1H), 2.52 (m, 2H), 3.30 (m, 3H), 6.41 (d, 1H), 7.22 (s, 4H). MS (ESI) m/z 398.08 (M−Na)$^-$.

Example 84

Standard Methods for Determination of Enzymatic Cleavage of Prodrugs In Vitro

The stabilities of prodrugs were evaluated in one or more in vitro systems using a variety of tissue preparations following methods known in the art. The chemical stability of prodrugs in aqueous buffers at pH's of 2.0, 7.4 and 8.0 were also measured. Tissues were obtained from commercial sources (e.g., Pel-Freez Biologicals, Rogers, A R, or GenTest Corporation, Woburn, Mass.). Experimental conditions used for the in vitro studies are described in Table 1 below. Each preparation was incubated with test compound at 37° C. for one hour. Aliquots (50 μL) were removed at 0, 30, and 60 min and quenched with 0.1% trifluoroacetic acid in acetonitrile. Samples were then centrifuged and analyzed by LC/MS/MS (see Example 86 below for method details). Stability of prodrugs towards specific enzymes (e.g., peptidases, etc.) were also assessed in vitro by incubation with the purified enzyme:

Pancreatin Stability. Stability studies were conducted by incubating prodrug (5 μM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used.

For stability studies, prodrug (5 μM) was incubated in Caco-2 homogenate S9 fraction (0.5 mg protein per mL) for 60 min at 37° C. Concentrations of intact prodrug and released baclofen were determined at zero time and 60 minutes using LC/MS/MS. Data from these studies is summarized in Table 2.

TABLE 1

Standard Conditions for Prodrug In Vitro Metabolism Studies

| Preparation | Substrate Concentration | Cofactors |
|---|---|---|
| Rat Plasma | 2.0 μM | None |
| Human Plasma | 2.0 μM | None |
| Rat Liver S9 (0.5 mg/mL) | 2.0 μM | NADPH* |
| Human Liver S9 (0.5 mg/mL) | 2.0 μM | NADPH* |
| Human Intestine S9 (0.5 mg/mL) | 2.0 μM | NADPH* |
| Carboxypeptidase A (10 units/mL) | 2.0 μM | None |
| Caco-2 Homogenate | 5.0 μM | None |
| Pancreatin | 5.0 μM | None |

*NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

TABLE 2

% of Prodrug Remaining/% of Baclofen Released from Baclofen Prodrugs after 60 min. in Various Tissue Preparations

|  | (10) | (12) | (14) | (16) | (18) | (20) | (23) |
|---|---|---|---|---|---|---|---|
| pH 2.0 | 100/1 | 100/0 | 100/1 | 100/0 | 105/0 | 100/0 | 107/0 |
| pH 7.4 | 101/3 | 100/0 | 103/1 | 100/0 | 95/0 | 100/0 | 89/1 |
| pH 8.0 | 98/9 | 105/0 | 102/2 | 100/0 | 102/0 | 103/0 | 90/2 |
| Rat Plasma | 85/15 | 72/14 | 55/48 | 54/40 | 39/60 | 92/8 | 11/93 |
| Human Plasma | 64/26 | 95/5 | 90/10 | 62/20 | 61/27 | 82/9 | 96/3 |
| Rat Liver S9 (0.5 mg/mL) | 0/78 | 3/100 | 2/99 | 1/100 | 1/100 | 25/75 | 3/107 |
| Human Liver S9 (0.5 mg/mL) | 1/80 | 1/100 | 2/102 | 1/100 | 2/100 | 1/100 | 4/105 |
| Caco-2 S9 | 2/96 | 2/100 | 2/101 | 1/84 | 2/91 | 58/36 | 82/24 |

|  | (25) | (27) | (30) | (33) | (34) | (40) | (43) |
|---|---|---|---|---|---|---|---|
| pH 2.0 | 101/0 | 102/0 | 100/0 | 100/0 | 100/0 | 103/0 | 95/0 |
| pH 7.4 | 100/0 | 100/0 | 87/1 | 72/0 | 100/0 | 100/0 | 87/0 |
| pH 8.0 | 100/0 | 101/1 | 81/3 | 101/0 | 100/0 | 107/2 | 92/0 |
| Rat Plasma | 5/96 | 12/88 | 58/42 | 73/30 | 78/18 | 72/17 | 71/29 |
| Human Plasma | 93/4 | 82/12 | 85/8 | 96/4 | 90/2 | 101/2 | 100/2 |
| Rat Liver S9 (0.5 mg/mL) | 1/98 | 0/89 | 1/85 | 4/101 | 1/100 | 8/96 | 3/97 |
| Human Liver S9 (0.5 mg/mL) | 4/91 | 8/79 | 7/87 | 3/101 | 3/100 | 1/105 | 61/39 |

TABLE 2-continued

% of Prodrug Remaining/% of Baclofen Released from Baclofen Prodrugs after 60 min. in Various Tissue Preparations

| Caco-2 S9 | 2/95 | 27/67 | 24/70 | 3/95 | 2/100 | 15/85 | 51/49 |
|---|---|---|---|---|---|---|---|
| Pancreatin | 22/84 | 71/9 | 90/9 | 46/52 | 81/18 | 43/58 | 82/4 |

| | (51) | (57) | (59) | (62) | (84) | (85) | (86) |
|---|---|---|---|---|---|---|---|
| pH 2.0 | 100/0 | 100/0 | 103/0 | 105/0 | 85/0 | 82/0 | 101/0 |
| pH 7.4 | 97/2 | 100/0 | 103/1 | 94/2 | 84/0 | 92/0 | 99/1 |
| pH 8.0 | 91/9 | 100/0 | 97/2 | 88/8 | 94/1 | 93/0 | 94/2 |
| Rat Plasma | 31/72 | 82/10 | 2/85 | 5/95 | 91/11 | 82/12 | 1/83 |
| Human Plasma | 53/50 | 73/14 | 77/11 | 84/2 | 89/4 | 95/4 | 73/13 |
| Rat Liver S9 (0.5 mg/mL) | 2/103 | 2/78 | 2/85 | 2/80 | 4/91 | 2/91 | 2/92 |
| Human Liver S9 (0.5 mg/mL) | 6/91 | 1/86 | 1/82 | 0/69 | 2/82 | 2/84 | 2/87 |
| Caco-2 S9 | 3/100 | 2/104 | 3/104 | 1/89 | 13/76 | 4/82 | 2/95 |
| Pancreatin | 44/50 | 12/75 | 46/50 | 1/79 | 47/40 | 15/64 | 4/76 |

| | (90) | (91) | (92) | (100) | (104) |
|---|---|---|---|---|---|
| pH 2.0 | 97/0 | 100/0 | 97/0 | 101/0 | 100/0 |
| pH 7.4 | 93/0 | 97/0 | 95/0 | 98/0 | 100/0 |
| pH 8.0 | 93/1 | 94/1 | 96/1 | 95/0 | 100/0 |
| Rat Plasma | 5/77 | 80/10 | 12/73 | 9/64 | 14/85 |
| Human Plasma | 81/2 | 83/2 | 86/1 | 89/3 | 98/2 |
| Rat Liver S9 (0.5 mg/mL) | 3/85 | 22/70 | 6/88 | 3/85 | 3/97 |
| Human Liver S9 (0.5 mg/mL) | 1/78 | 1/78 | 4/80 | 1/83 | 3/97 |
| Caco-2 S9 | 5/90 | 6/107 | 55/53 | 7/90 | 17/83 |
| Pancreatin | 9/68 | 11/78 | 85/7 | 68/27 | 90/6 |

Example 85

In Vitro Determination of Caco-2 Cellular Permeability of Prodrugs

The trans-epithelial cellular permeability of prodrugs of baclofen and baclofen analogs may be assessed in vitro using standard methods well known in the art (see, e.g., Stewart, et al., *Pharm. Res.*, 1995, 12, 693). For example, cellular permeability may be evaluated by examining the flux of a prodrug across a cultured polarized cell monolayer (e.g., Caco-2 cells). Caco-2 cells obtained from continuous culture (passage less than 28) were seeded at high density onto Transwell polycarbonate filters. Cells were maintained with DMEM/10% fetal calf serum+0.1 mM nonessential amino acids+2 mM L-Gln, 5% $CO_2$/95% $O_2$, 37° C. until the day of the experiment. Permeability studies were conducted at pH 6.5 apically (in 50 mM MES buffer containing 1 mM $CaCl_2$, 1 mM $MgCl_2$, 150 mM NaCl, 3 mM KCl, 1 mM $NaH_2PO_4$, 5 mM glucose) and pH 7.4 basolaterally (in Hanks' balanced salt solution containing 10 mM HEPES) in the presence of efflux pump inhibitors (250 μM MK-571, 250 μM Verapamil, 1 mM Ofloxacin). Inserts were placed in 12 or 24 well plates containing buffer and incubated for 30 min at 37C.°. Prodrug (200 μM) was added to the apical or basolateral compartment (donor) and concentrations of prodrug and/or released parent drug in the opposite compartment (receiver) were determined at intervals over 1 hour using LC/MS/MS. Values of apparent permeability ($P_{app}$) were calculated using the equation:

$P_{app} = V_r(dC/dt)/(AC_o)$

Here $V_r$ is the volume of the receiver compartment in mL; dC/dt is the total flux of prodrug and parent drug (μM/s), determined from the slope of the plot of concentration in the receiver compartment versus time; $C_o$ is the initial concentration of prodrug in μM; A is the surface area of the membrane in $cm^2$. Preferably, prodrugs with significant transcellular permeability demonstrate a value of $P_{app}$ of $\geq 1 \times 10^{-6}$ cm/s and more preferably, a value of $P_{app}$ of $\geq 1 \times 10^{-5}$ cm/s, and still more preferably a value of $P_{app}$ of $\geq 5 \times 10^{-5}$ cm/s. Typical values of $P_{app}$ obtained for baclofen prodrugs are shown in the following table:

| Compound | $P_{app}$ (apical to basolateral) (cm/s) | $P_{app}$ (basolateral to apical) (cm/s) | Ratio A − B/B − A |
|---|---|---|---|
| (10) | $1.1 \times 10^{-6}$ | $9.2 \times 10^{-7}$ | 1.2 |
| (12) | $1.0 \times 10^{-4}$ | $1.7 \times 10^{-5}$ | 5.9 |
| (14) | $2.2 \times 10^{-5}$ | $5.3 \times 10^{-6}$ | 4.1 |
| (16) | $6.1 \times 10^{-6}$ | $1.2 \times 10^{-6}$ | 5.1 |
| (18) | $6.4 \times 10^{-6}$ | $5.6 \times 10^{-6}$ | 1.1 |
| (20) | $9.1 \times 10^{-5}$ | $7.7 \times 10^{-6}$ | 11.8 |
| (25) | $5.8 \times 10^{-5}$ | $1.4 \times 10^{-5}$ | 4.1 |
| (27) | $6.5 \times 10^{-5}$ | $9.4 \times 10^{-6}$ | 6.9 |
| (30) | $8.7 \times 10^{-6}$ | $2.3 \times 10^{-6}$ | 3.8 |
| (32) | $3.7 \times 10^{-5}$ | $4.9 \times 10^{-6}$ | 7.6 |
| (36) | $2.9 \times 10^{-5}$ | $1.9 \times 10^{-5}$ | 1.5 |
| (38) | $1.5 \times 10^{-5}$ | $1.4 \times 10^{-5}$ | 1.1 |
| (40) | $6.9 \times 10^{-5}$ | $3.0 \times 10^{-5}$ | 2.3 |
| (43) | $4.2 \times 10^{-5}$ | $1.8 \times 10^{-5}$ | 2.3 |
| (48) | $1.1 \times 10^{-5}$ | $1.7 \times 10^{-6}$ | 6.5 |
| (50) | $2.5 \times 10^{-5}$ | $1.4 \times 10^{-5}$ | 1.8 |
| (51) | $2.9 \times 10^{-5}$ | $9.6 \times 10^{-6}$ | 3.0 |
| (53) | $8.5 \times 10^{-5}$ | $3.6 \times 10^{-5}$ | 2.4 |
| (71) | $9.2 \times 10^{-5}$ | $1.3 \times 10^{-5}$ | 7.1 |
| (72) | $2.8 \times 10^{-5}$ | $8.0 \times 10^{-6}$ | 3.5 |
| (73) | $2.2 \times 10^{-5}$ | $6.8 \times 10^{-6}$ | 3.2 |
| (74) | $1.0 \times 10^{-5}$ | $8.9 \times 10^{-7}$ | 11.2 |
| (78) | $1.5 \times 10^{-5}$ | $1.9 \times 10^{-6}$ | 7.9 |

The data in this table shows that several of the prodrugs disclosed herein have high cellular permeability and should be well absorbed from the intestine. With the exception of compound (10), the apical-to-basolateral permeabilities of these prodrugs significantly exceed their basolateral-to-apical permeabilities, suggesting that these compounds may be substrates for active transport mechanisms present in the apical membrane of Caco cells (though some component of this transcellular permeability may also be mediated by passive diffusion).

Example 86

Uptake of R-Baclofen Following Administration of R-Baclofen or R-Baclofen Prodrugs Intracolonically in Rats Sustained release oral dosage forms, which release drug slowly over periods of 6-24 hours, generally release a significant proportion of the dose within the colon. Thus, drugs suitable for use in such dosage forms preferably exhibit good colonic absorption. This experiment was conducted to assess the suitability of baclofen prodrugs for use in an oral sustained release dosage form.

Step A: Administration Protocol

Rats were obtained commercially and were pre-cannulated in the both the ascending colon and the jugular vein. Animals were conscious at the time of the experiment. All animals were fasted overnight and until 4 hours post-dosing. R-Baclofen or baclofen prodrugs (10), (12), (23), (25), (27), (32), (33), (40), (51), (92), (100) and (104) were administered as a solution (in water or PEG 400) directly into the colon via the cannula at a dose equivalent to 10 mg of baclofen equivalents per kg body weight. Blood samples (0.5 mL) were obtained from the jugular cannula at intervals over 8 hours and were quenched immediately by addition of methanol to prevent further conversion of the prodrug. Blood samples were analyzed as described below.

Step B: Sample Preparation for Colonic Absorbed Drug

1. Rat blood was collected at different time points and 100 µL of blood was added into an eppendorf tube containing 300 µL of methanol and vortexed to mix immediately.
2. 20 µL of p-chlorophenylalanine was added as an internal standard.
3. 300 µL of methanol was added into each tube followed by 20 µL of p-chlorophenylalanine. 90 µL of blank rat-blood was added to each tube and mix. Then 10 µL of a baclofen standard solution (0.04, 0.2, 1, 5, 25, 100 µg/mL) was added to make up a final calibration standard (0.004, 0.02, 0.1, 0.5, 2.5, 10 µg/mL).
4. Samples were vortexed and centrifuged at 14,000 rpm for 10 min.
5. Supernatant was taken for LC/MS/MS analysis.

Step C: LC/MS/MS Analysis

An API 2000 LC/MS/MS spectrometer equipped with Shidmadzu 10ADVp binary pumps and a CTC HTS-PAL autosampler were used in the analysis. A Phenomenex hydro-RP 4.6×50 mm column was used during the analysis. The mobile phase was water with 0.1% formic acid (A) and acetonitrile with 0.1% formic acid (B). The gradient condition was: 10% B for 0.5 min, then to 95% B in 2.5 mm, then maintained at 95% B for 1.5 min. The mobile phase was returned to 10% B for 2 min. A TurboIonSpray source was used on the API 2000. The analysis was done in positive ion mode and an MRM transition of m/z 214/151 was used in the analysis of baclofen (MRM transitions m/z 330/240 for (10), m/z 392/240 for (12), m/z 372/240 for (23), m/z 400/240 for (25), m/z 400/240 for (27), m/z 372/240 for (32), m/z 372/240 for (33), 406/240 for (40), 454/61 for (51), 400/240 for (92), 400/240 for (100) and 400/240 for (104) were used). 10 µL of the samples were injected. The peaks were integrated using Analyst 1.2 quantitation software. Following colonic administration of prodrugs (12), (23), (25), (27), (32), (33), (40), (51), (92), (100) and (104) the maximum plasma concentrations of R-baclofen ($C_{max}$), as well as the area under the baclofen plasma concentration vs. time curves (AUC) were significantly greater (>2-fold) than that produced from colonic administration of R-baclofen itself. This data demonstrates that these compounds may be formulated as compositions suitable for enhanced absorption and/or effective sustained release of baclofen analogs to minimize dosing frequency due to rapid systemic clearance of these baclofen analogs.

Example 87

Pharmacokinetics of R-Baclofen Following Intravenous Administration to Cynomolgus Monkeys R-Baclofen hydrochloride salt was administered to four male cynomolgus monkeys as an aqueous solution by intravenous bolus injection into the saphenous vein at a dose of 1.2 mg/kg. Blood samples were obtained from all animals at intervals over 24 hours post-dosing. Blood was processed immediately for plasma at 4° C. All plasma samples were subsequently analyzed for R-baclofen using the LC/MS/MS assay described above. The mean R-baclofen exposure $AUC_{inf}$=3.6 h.µg/mL.

Example 88

Uptake of R-Baclofen Following Administration of R-Baclofen or R-Baclofen Prodrugs Intracolonically in Cynomolgus Monkeys R-Baclofen hydrochloride salt and R-baclofen prodrugs (5 mg baclofen-eq/kg) were administered to groups of four male cynomolgus monkeys as either aqueous solutions or suspensions in 0.5% methyl cellulose/0.1% Tween-80 via bolus injection directly into the colon via an indwelling cannula. For colonic delivery a flexible French catheter was inserted into the rectum of each monkey and extended to the proximal colon (approx. 16 inches) using fluoroscopy. Monkeys were lightly sedated by administration of Telazol/ketamine during dosing. A washout period of at least 5 to 7 days was allowed between treatments. Following dosing, blood samples were obtained at intervals over 24 hours and were immediately quenched and processed for plasma at 4° C. All plasma samples were subsequently analyzed for R-baclofen and intact prodrug using the LC/MS/MS assay described above. Following colonic administration of prodrugs (12), (27), (25), (40) and (51), the maximum plasma concentrations of baclofen ($C_{max}$), as well as the area under the baclofen plasma concentration vs. time curves (AUC) were significantly greater (>2-fold) than that produced from colonic administration of R-baclofen itself, while colonic administration of (92), (100) and (104) produced R-baclofen exposures that were greater than 10-fold that produced from colonic administration of R-baclofen itself. This data demonstrates that these compounds may be formulated as compositions suitable for enhanced absorption and/or effective sustained release of baclofen analogs to minimize dosing frequency due to rapid systemic clearance of these baclofen analogs.

Example 89

Uptake of R-Baclofen Following Oral Administration of R-Baclofen Prodrugs to Cynomolgus Monkeys The R-baclofen prodrugs (92) and (104) (5 mg baclofen-eq/kg) were administered by oral gavage to groups of four male cynomolgus monkeys as either an aqueous solution or suspension in 0.5% methyl cellulose/0.1% Tween-80 respectively. Following dosing, blood samples were obtained at intervals over 24 hours and were immediately quenched and processed for plasma at 4° C. All plasma samples were subsequently analyzed for R-baclofen and intact prodrug using the LC/MS/MS assay described above. The oral bioavailability of both prodrugs (92) and (104) as R-baclofen was determined to be greater than 80%.

Finally, it should be noted that there are alternative ways of implementing the disclosures contained herein. Accordingly, the present embodiments are to be considered as illustrative and not restrictive, and the claims are not to be limited to the details given herein, but may be modified within the scope and equivalents thereof. All publications and patents disclosed herein are incorporated herein by reference in their entirety.

What is claimed is:

1. A compound of Formula (I):

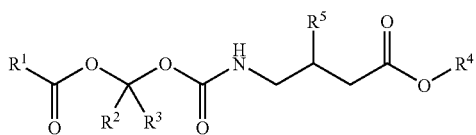

(I)

or pharmaceutically acceptable salts, hydrates or solvates thereof, wherein:

$R^1$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^2$ and $R^3$ are independently selected from the group consisting of hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl and substituted heteroarylalkyl or optionally, $R^2$ and $R^3$ together with the carbon atom to which they are bonded form a cycloalkyl, substituted cycloalkyl, cycloheteroalkyl or substituted cycloheteroalkyl ring;

$R^4$ is selected from the group consisting of hydrogen, alkyl, substituted alkyl, aryl, substituted aryl, arylalkyl, substituted arylalkyl, aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or trialkylsilyl; and $R^5$ is selected from the group consisting of substituted aryl, heteroaryl and substituted heteroaryl.

2. A pharmaceutical composition comprising a compound of claim 1 and a pharmaceutically acceptable vehicle.

3. The composition of claim 2, comprising an oral dosage form.

4. The composition of claim 3, wherein the oral dosage form is a sustained release oral dosage form.

5. The composition of claim 4, wherein the dosage form is adapted to be swallowed by a patient in order to introduce the dosage form into an intestinal lumen of the patient; the dosage form further being adapted to release the compound of claim 1 gradually into the intestinal lumen of the patient over a period of hours after said swallowing, the gradual release causing the compound of claim 1 to be cleaved after said swallowing to provide a therapeutic concentration the compound of claim 1 in the plasma of the patient.

6. The composition of claim 5 wherein the period of hours comprises at least about 6 hours.

7. The composition of claim 5, wherein the period of hours comprises at least about 8 hours.

8. The composition of claim 5, wherein the period of hours comprises at least about 12 hours.

* * * * *